US012187786B2

(12) United States Patent
Sampei et al.

(10) Patent No.: US 12,187,786 B2
(45) Date of Patent: Jan. 7, 2025

(54) ANTI-DENGUE VIRUS ANTIBODIES, POLYPEPTIDES CONTAINING VARIANT Fc REGIONS, AND METHODS OF USE

(71) Applicants: Chugai Seiyaku Kabushiki Kaisha, Tokyo (JP); Agency for Science, Technology and Research, Singapore (SG)

(72) Inventors: Zenjiro Sampei, Shizuoka (JP); Xing'er Christine Koo, Singapore (SG); Katja Fink, Singapore (SG); Roland Zuest, Singapore (SG)

(73) Assignees: Chugai Seiyaku Kabushiki Kaisha, Tokyo (JP); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 18/453,418

(22) Filed: Aug. 22, 2023

(65) Prior Publication Data

US 2024/0018219 A1    Jan. 18, 2024

Related U.S. Application Data

(60) Continuation of application No. 17/066,092, filed on Oct. 8, 2020, now Pat. No. 11,780,908, which is a division of application No. 16/435,979, filed on Jun. 10, 2019, now Pat. No. 10,844,113, which is a continuation of application No. 16/333,736, filed as application No. PCT/SG2017/050465 on Sep. 15, 2017, now Pat. No. 10,604,561.

(30) Foreign Application Priority Data

Sep. 16, 2016 (SG) .......................... 10201607778X

(51) Int. Cl.
| | | |
|---|---|---|
| *C07K 16/10* | (2006.01) | |
| *A61K 39/12* | (2006.01) | |
| *A61K 39/395* | (2006.01) | |
| *A61P 31/12* | (2006.01) | |
| *C07K 14/005* | (2006.01) | |
| *C07K 16/00* | (2006.01) | |
| *A61K 39/00* | (2006.01) | |

(52) U.S. Cl.
CPC .......... *C07K 16/1081* (2013.01); *A61P 31/12* (2018.01); *A61K 2039/505* (2013.01); *C07K 2317/52* (2013.01); *C07K 2317/56* (2013.01); *C07K 2317/734* (2013.01); *C07K 2317/92* (2013.01); *C07K 2317/94* (2013.01); *Y02A 50/30* (2018.01)

(58) Field of Classification Search
CPC ........ A61K 2039/505; A61K 2039/507; A61P 31/12; A61P 31/14; C07K 2317/56
See application file for complete search history.

(56) References Cited

U.S. PATENT DOCUMENTS

| | | |
|---|---|---|
| 4,676,980 A | 6/1987 | Segal et al. |
| 4,737,456 A | 4/1988 | Weng et al. |
| 4,816,567 A | 3/1989 | Cabilly et al. |
| 5,126,250 A | 6/1992 | McDonough et al. |
| 5,208,020 A | 5/1993 | Chari et al. |
| 5,416,064 A | 5/1995 | Chari et al. |
| 5,500,362 A | 3/1996 | Robinson et al. |
| 5,571,894 A | 11/1996 | Wels et al. |
| 5,587,458 A | 12/1996 | King et al. |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,670,373 A | 9/1997 | Kishimoto |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,750,373 A | 5/1998 | Garrard et al. |
| 5,767,285 A | 6/1998 | Hamann et al. |
| 5,770,429 A | 6/1998 | Lonberg et al. |

(Continued)

FOREIGN PATENT DOCUMENTS

| | | |
|---|---|---|
| AU | 2010206050 A1 | 8/2010 |
| CA | 2203182 A1 | 5/1996 |

(Continued)

OTHER PUBLICATIONS

U.S. Appl. No. 12/680,082, filed Jun. 25, 2010, Igawa et al.

(Continued)

*Primary Examiner* — Barry A Chestnut

(74) *Attorney, Agent, or Firm* — Nixon & Vanderhye P.C.

(57) ABSTRACT

The disclosure provides anti-DENV antibodies and methods of making and using the same. Nucleic acids encoding the anti-DENV antibodies and host cells comprising the nucleic acids are also provided. The anti-DENV antibodies have uses that include treating DENV infection. The disclosure also provided polypeptides containing a variant Fc region and methods of making and using the same. Nucleic acids encoding the polypeptides and host cells comprising the nucleic acids are also provided. The polypeptides have uses that include treating a viral infection. Also claimed is a polypeptide comprising a Fc variant comprising at least one amino acid alteration in a parent Fc region, wherein the variant Fc region has a substantially decreased FcγR-binding activity and does not have a substantially decreased C1q-binding activity when compared to the parent Fc region.

1 Claim, 18 Drawing Sheets

Specification includes a Sequence Listing.

(56) References Cited

U.S. PATENT DOCUMENTS

| | | |
|---|---|---|
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,877,296 A | 3/1999 | Hamann et al. |
| 5,959,177 A | 9/1999 | Hein et al. |
| 5,994,524 A | 11/1999 | Matsushima et al. |
| 6,024,956 A | 2/2000 | Matsushima et al. |
| 6,025,158 A | 2/2000 | Gonzalez et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,245,894 B1 | 6/2001 | Matsushima et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,458,355 B1 | 10/2002 | Hsei et al. |
| 6,602,684 B1 | 8/2003 | Umana et al. |
| 6,630,579 B2 | 10/2003 | Chari et al. |
| 6,723,319 B1 | 4/2004 | Ito et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,122,637 B2 | 10/2006 | Presta |
| 7,125,978 B1 | 10/2006 | Vezina et al. |
| 7,189,826 B2 | 3/2007 | Rodman |
| 7,217,797 B2 | 5/2007 | Hinton et al. |
| 7,282,568 B2 | 10/2007 | Teeling et al. |
| 7,332,581 B2 | 2/2008 | Presta |
| 7,358,054 B2 | 4/2008 | Lyne et al. |
| 7,371,826 B2 | 5/2008 | Presta |
| 7,479,543 B2 | 1/2009 | Tsuchiya et al. |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 7,632,497 B2 | 12/2009 | Stavenhagen |
| 7,655,232 B2 | 2/2010 | Pons et al. |
| 7,670,600 B2 | 3/2010 | Dall'Acqua et al. |
| 7,785,791 B2 | 8/2010 | Presta |
| 7,824,674 B2 | 11/2010 | Ito et al. |
| 7,928,205 B2 | 4/2011 | Dillon et al. |
| 7,955,590 B2 | 6/2011 | Gillies et al. |
| 8,017,121 B2 | 9/2011 | Kishimoto et al. |
| 8,048,421 B2 | 11/2011 | Kai et al. |
| 8,147,829 B2 | 4/2012 | Hariharan et al. |
| 8,217,147 B2 | 7/2012 | Stavenhagen et al. |
| 8,323,962 B2 | 12/2012 | Dall'Acqua et al. |
| 8,604,174 B2 | 12/2013 | Babcook et al. |
| 8,637,641 B2 | 1/2014 | Dahiyat et al. |
| 9,228,017 B2 | 1/2016 | Igawa et al. |
| 9,260,516 B2 | 2/2016 | Nishimoto et al. |
| 9,605,061 B2 | 3/2017 | Lazar et al. |
| 9,688,762 B2 | 6/2017 | Igawa et al. |
| 9,701,759 B2 | 7/2017 | Desjarlais et al. |
| 9,969,800 B2 | 5/2018 | Igawa et al. |
| 10,066,018 B2 | 9/2018 | Igawa et al. |
| 10,150,808 B2 | 12/2018 | Kuramochi et al. |
| 10,253,091 B2 | 4/2019 | Igawa et al. |
| 10,421,804 B2 | 9/2019 | Kyratsous et al. |
| 10,604,561 B2 | 3/2020 | Sampei et al. |
| 11,332,533 B2 | 5/2022 | Igawa et al. |
| 2001/0001663 A1 | 5/2001 | Kishimoto et al. |
| 2002/0082396 A1 | 6/2002 | Matsushima et al. |
| 2002/0164328 A1 | 11/2002 | Shinkawa et al. |
| 2002/0187150 A1 | 12/2002 | Mihara et al. |
| 2003/0077283 A1 | 4/2003 | Ye |
| 2003/0115614 A1 | 6/2003 | Kanda et al. |
| 2003/0157108 A1 | 8/2003 | Presta |
| 2004/0071706 A1 | 4/2004 | Kishimoto et al. |
| 2004/0081651 A1 | 4/2004 | Karpusas et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0191244 A1 | 9/2004 | Presta |
| 2004/0208873 A1 | 10/2004 | Teeling et al. |
| 2005/0014934 A1 | 1/2005 | Hinton et al. |
| 2005/0032114 A1 | 2/2005 | Hinton et al. |
| 2005/0079574 A1 | 4/2005 | Bond |
| 2005/0119455 A1 | 6/2005 | Fuh et al. |
| 2005/0123546 A1 | 6/2005 | Umana et al. |
| 2005/0142133 A1 | 6/2005 | Lazar et al. |
| 2005/0142635 A1 | 6/2005 | Tsuchiya et al. |
| 2005/0158825 A1 | 7/2005 | Power et al. |
| 2005/0260186 A1 | 11/2005 | Bookbinder et al. |
| 2005/0261229 A1 | 11/2005 | Gillies et al. |
| 2005/0266000 A1 | 12/2005 | Bond et al. |
| 2006/0025576 A1 | 2/2006 | Miller et al. |
| 2006/0104968 A1 | 5/2006 | Bookbinder et al. |
| 2006/0134709 A1 | 6/2006 | Stavenhagen et al. |
| 2006/0194280 A1 | 8/2006 | Dillon et al. |
| 2006/0194291 A1 | 8/2006 | Presta |
| 2006/0198840 A1 | 9/2006 | Dall'Acqua et al. |
| 2006/0275282 A1 | 12/2006 | Moore et al. |
| 2006/0292147 A1 | 12/2006 | Yoshizaki et al. |
| 2007/0036799 A1 | 2/2007 | Stavenhagen et al. |
| 2007/0061900 A1 | 3/2007 | Murphy et al. |
| 2007/0117126 A1 | 5/2007 | Sidhu et al. |
| 2007/0134234 A1 | 6/2007 | Smith et al. |
| 2007/0148167 A1 | 6/2007 | Strohl |
| 2007/0160598 A1 | 7/2007 | Dennis et al. |
| 2007/0212357 A1 | 9/2007 | Pons et al. |
| 2007/0237764 A1 | 10/2007 | Birtalan et al. |
| 2007/0292936 A1 | 12/2007 | Barthelemy et al. |
| 2008/0050370 A1 | 2/2008 | Glaser et al. |
| 2008/0069820 A1 | 3/2008 | Fuh et al. |
| 2008/0274506 A1 | 11/2008 | Presta |
| 2009/0002360 A1 | 1/2009 | Chen et al. |
| 2009/0130110 A1 | 5/2009 | Babcook et al. |
| 2009/0324589 A1 | 12/2009 | Igawa et al. |
| 2010/0004429 A1 | 1/2010 | Kai et al. |
| 2010/0008907 A1 | 1/2010 | Nishimoto et al. |
| 2010/0098710 A1 | 4/2010 | Hariharan et al. |
| 2010/0099147 A1 | 4/2010 | Hariharan et al. |
| 2010/0298542 A1 | 11/2010 | Igawa et al. |
| 2011/0245473 A1 | 10/2011 | Igawa et al. |
| 2011/0311454 A1 | 12/2011 | Dall'Acqua et al. |
| 2012/0028304 A1 | 2/2012 | Dahiyat et al. |
| 2012/0065379 A1 | 3/2012 | Igawa et al. |
| 2012/0071634 A1 | 3/2012 | Igawa et al. |
| 2012/0238729 A1 | 9/2012 | Kuramochi et al. |
| 2013/0085074 A1 | 4/2013 | Walker et al. |
| 2013/0101581 A1 | 4/2013 | Kuramochi et al. |
| 2014/0249297 A1 | 9/2014 | Lazar et al. |
| 2014/0294833 A1 | 10/2014 | Desjarlais et al. |
| 2014/0363426 A1 | 12/2014 | Moore et al. |
| 2015/0274809 A1 | 10/2015 | Igawa et al. |
| 2016/0039912 A1 | 2/2016 | Mimoto et al. |
| 2016/0159915 A1 | 6/2016 | Igawa et al. |
| 2016/0229908 A1 | 8/2016 | Igawa et al. |
| 2017/0181987 A1 | 6/2017 | Svensson et al. |
| 2017/0342154 A1 | 11/2017 | Igawa et al. |
| 2018/0258163 A1 | 9/2018 | Igawa et al. |
| 2019/0169286 A1 | 6/2019 | Kakiuchi et al. |
| 2019/0211081 A1 | 7/2019 | Igawa et al. |
| 2019/0218277 A1 | 7/2019 | Sampei et al. |
| 2021/0095008 A1 | 4/2021 | Sampei et al. |
| 2022/0064264 A1 | 3/2022 | Igawa et al. |
| 2022/0251225 A1 | 8/2022 | Igawa et al. |

FOREIGN PATENT DOCUMENTS

| | | |
|---|---|---|
| CA | 2443294 A1 | 10/2002 |
| CA | 2523577 A1 | 11/2004 |
| CA | 2531482 A1 | 1/2005 |

(56) References Cited

FOREIGN PATENT DOCUMENTS

| | | |
|---|---|---|
| CA | 2549467 A1 | 7/2005 |
| CA | 2560953 A1 | 9/2005 |
| CA | 2625773 A1 | 4/2007 |
| CA | 2626688 A1 | 4/2007 |
| CA | 2203182 C | 11/2009 |
| CA | 2549467 C | 12/2012 |
| CA | 2443294 C | 9/2013 |
| CN | 1156460 A | 8/1997 |
| CN | 100455598 C | 1/2009 |
| CN | 102918057 A | 2/2013 |
| CN | 103975060 A | 8/2014 |
| EP | 0404097 A2 | 12/1990 |
| EP | 0425235 B1 | 9/1996 |
| EP | 0770628 A1 | 5/1997 |
| EP | 1509770 A1 | 3/2005 |
| EP | 0770628 B1 | 9/2006 |
| EP | 1701979 A2 | 9/2006 |
| EP | 1752471 A1 | 2/2007 |
| EP | 1772465 A1 | 4/2007 |
| EP | 1847602 A1 | 10/2007 |
| EP | 2031064 A1 | 3/2009 |
| EP | 2194066 A1 | 6/2010 |
| EP | 2202245 A1 | 6/2010 |
| EP | 2206775 A1 | 7/2010 |
| EP | 2236604 A1 | 10/2010 |
| EP | 2275443 A1 | 1/2011 |
| EP | 2409991 A1 | 1/2012 |
| EP | 2471813 A1 | 7/2012 |
| EP | 1847602 B1 | 4/2014 |
| EP | 2762564 A1 | 8/2014 |
| EP | 3059246 A1 | 8/2016 |
| JP | H08217799 A | 8/1996 |
| JP | 3865418 B2 | 1/2007 |
| JP | 2009541352 A | 11/2009 |
| JP | 2013518606 A | 5/2013 |
| JP | 5421105 B2 | 2/2014 |
| JP | 2014055145 A | 3/2014 |
| JP | 5484060 B2 | 5/2014 |
| JP | 5717624 B2 | 5/2015 |
| JP | 5787446 B2 | 9/2015 |
| JP | 2016026190 A | 2/2016 |
| JP | 6082447 B2 | 2/2017 |
| KR | 20100074221 A | 7/2010 |
| KR | 20120035192 A | 4/2012 |
| KR | 101282320 B1 | 7/2013 |
| KR | 101680906 B1 | 11/2016 |
| RU | 2232773 C2 | 7/2004 |
| RU | 2009112723 A | 10/2010 |
| TW | 416960 B | 1/2001 |
| TW | 201643190 A | 12/2016 |
| TW | 201712032 A | 4/2017 |
| TW | I621628 B | 4/2018 |
| WO | WO-9301161 A1 | 1/1993 |
| WO | WO-9308829 A1 | 5/1993 |
| WO | WO-9316185 A2 | 8/1993 |
| WO | WO-9411026 A2 | 5/1994 |
| WO | WO-9429351 A2 | 12/1994 |
| WO | WO-9602576 A1 | 2/1996 |
| WO | WO-9709351 A1 | 3/1997 |
| WO | WO-9730087 A1 | 8/1997 |
| WO | WO-9805787 A1 | 2/1998 |
| WO | WO-9858964 A1 | 12/1998 |
| WO | WO-9922764 A1 | 5/1999 |
| WO | WO-9951642 A1 | 10/1999 |
| WO | WO-9958572 A1 | 11/1999 |
| WO | WO-0042072 A2 | 7/2000 |
| WO | WO-0061739 A1 | 10/2000 |
| WO | WO-0129246 A1 | 4/2001 |
| WO | WO-0231140 A1 | 4/2002 |
| WO | WO-02060919 A2 | 8/2002 |
| WO | WO-02072605 A2 | 9/2002 |
| WO | WO-03011878 A2 | 2/2003 |
| WO | WO-03074679 A2 | 9/2003 |
| WO | WO-03084570 A1 | 10/2003 |
| WO | WO-03085107 A1 | 10/2003 |
| WO | WO-03085119 A1 | 10/2003 |
| WO | WO-2004029207 A2 | 4/2004 |
| WO | WO-2004035752 A2 | 4/2004 |
| WO | WO-2004056312 A2 | 7/2004 |
| WO | WO-2004058797 A2 | 7/2004 |
| WO | WO-2004092219 A2 | 10/2004 |
| WO | WO-2004096273 A1 | 11/2004 |
| WO | WO-2004099249 A1 | 11/2004 |
| WO | WO-2004113387 A2 | 12/2004 |
| WO | WO-2005005604 A2 | 1/2005 |
| WO | WO-2005035586 A1 | 4/2005 |
| WO | WO-2005035778 A1 | 4/2005 |
| WO | WO-2005037867 A1 | 4/2005 |
| WO | WO-2005047307 A2 | 5/2005 |
| WO | WO-2005047327 A2 | 5/2005 |
| WO | WO-2005053742 A1 | 6/2005 |
| WO | WO-2005056606 A2 | 6/2005 |
| WO | WO-2005056759 A2 | 6/2005 |
| WO | WO-2005077981 A2 | 8/2005 |
| WO | WO-2005092925 A2 | 10/2005 |
| WO | WO-2005100402 A1 | 10/2005 |
| WO | WO-2005123780 A2 | 12/2005 |
| WO | WO-2006004663 A2 | 1/2006 |
| WO | WO-2006019447 A1 | 2/2006 |
| WO | WO-2006020114 A2 | 2/2006 |
| WO | WO-2006029879 A2 | 3/2006 |
| WO | WO-2006031370 A2 | 3/2006 |
| WO | WO-2006044908 A2 | 4/2006 |
| WO | WO-2006047340 A2 | 5/2006 |
| WO | WO-2006047350 A2 | 5/2006 |
| WO | WO-2006050166 A2 | 5/2006 |
| WO | WO-2006053301 A2 | 5/2006 |
| WO | WO-2006071877 A2 | 7/2006 |
| WO | WO-2006075668 A1 | 7/2006 |
| WO | WO-2006085967 A2 | 8/2006 |
| WO | WO-2006105338 A2 | 10/2006 |
| WO | WO-2006113643 A2 | 10/2006 |
| WO | WO-2006130834 A2 | 12/2006 |
| WO | WO-2007008943 A2 | 1/2007 |
| WO | WO-2007041635 A2 | 4/2007 |
| WO | WO-2007044616 A2 | 4/2007 |
| WO | WO-2007092772 A2 | 8/2007 |
| WO | WO-2007108559 A1 | 9/2007 |
| WO | WO-2007114319 A1 | 10/2007 |
| WO | WO-2007114325 A1 | 10/2007 |
| WO | WO-2007150015 A2 | 12/2007 |
| WO | WO-2007150016 A2 | 12/2007 |
| WO | WO-2008017963 A2 | 2/2008 |
| WO | WO-2008022152 A2 | 2/2008 |
| WO | WO-2008031056 A2 | 3/2008 |
| WO | WO-2008036688 A2 | 3/2008 |
| WO | WO-2008077546 A1 | 7/2008 |
| WO | WO-2008091798 A2 | 7/2008 |
| WO | WO-2008091954 A2 | 7/2008 |
| WO | WO-2008092117 A2 | 7/2008 |
| WO | WO-2008098115 A2 | 8/2008 |
| WO | WO-2008121160 A2 | 10/2008 |
| WO | WO-2008130969 A2 | 10/2008 |
| WO | WO-2008145141 A1 | 12/2008 |
| WO | WO-2008150494 A1 | 12/2008 |
| WO | WO-2009000098 A2 | 12/2008 |
| WO | WO-2009000099 A2 | 12/2008 |
| WO | WO-2009011941 A2 | 1/2009 |
| WO | WO-2009026117 A2 | 2/2009 |
| WO | WO-2009032145 A1 | 3/2009 |
| WO | WO-2009032782 A2 | 3/2009 |
| WO | WO-2009036209 A2 | 3/2009 |
| WO | WO-2009041613 A1 | 4/2009 |
| WO | WO-2009041621 A1 | 4/2009 |
| WO | WO-2009041643 A1 | 4/2009 |
| WO | WO-2009052439 A2 | 4/2009 |
| WO | WO-2009058492 A2 | 5/2009 |
| WO | WO-2009072604 A1 | 6/2009 |
| WO | WO-2009086320 A1 | 7/2009 |
| WO | WO-2009089004 A1 | 7/2009 |
| WO | WO-2009100309 A2 | 8/2009 |
| WO | WO-2009125825 A1 | 10/2009 |
| WO | WO-2010033736 A1 | 3/2010 |
| WO | WO-2010043977 A2 | 4/2010 |

(56) References Cited

FOREIGN PATENT DOCUMENTS

| | | |
|---|---|---|
| WO | WO-2010045193 A1 | 4/2010 |
| WO | WO-2010106180 A2 | 9/2010 |
| WO | WO-2010107109 A1 | 9/2010 |
| WO | WO-2010107110 A1 | 9/2010 |
| WO | WO-2011021009 A1 | 2/2011 |
| WO | WO-2011091078 A2 | 7/2011 |
| WO | WO-2011100271 A2 | 8/2011 |
| WO | WO-2011122011 A2 | 10/2011 |
| WO | WO-2012016227 A2 | 2/2012 |
| WO | WO-2012073992 A1 | 6/2012 |
| WO | WO-2012082073 A1 | 6/2012 |
| WO | WO-2012093704 A1 | 7/2012 |
| WO | WO-2012115241 A1 | 8/2012 |
| WO | WO-2012132067 A1 | 10/2012 |
| WO | WO-2012151481 A1 | 11/2012 |
| WO | WO-2013012733 A1 | 1/2013 |
| WO | WO-2013046704 A2 | 4/2013 |
| WO | WO-2013046722 A1 | 4/2013 |
| WO | WO-2013047752 A1 | 4/2013 |
| WO | WO-2013081143 A1 | 6/2013 |
| WO | WO-2013089647 A1 | 6/2013 |
| WO | WO-2013125667 A1 | 8/2013 |
| WO | WO-2013151764 A1 | 10/2013 |
| WO | WO-2013166099 A1 | 11/2013 |
| WO | WO-2013173348 A1 | 11/2013 |
| WO | WO-2013180200 A1 | 12/2013 |
| WO | WO-2013180201 A1 | 12/2013 |
| WO | WO-2014006217 A1 | 1/2014 |
| WO | WO-2014025546 A2 | 2/2014 |
| WO | WO-2014030728 A1 | 2/2014 |
| WO | WO-2014114651 A1 | 7/2014 |
| WO | WO-2014145159 A2 | 9/2014 |
| WO | WO-2014145806 A2 | 9/2014 |
| WO | WO-2014163101 A1 | 10/2014 |
| WO | WO-2014184384 A1 | 11/2014 |
| WO | WO-2014190441 A1 | 12/2014 |
| WO | WO-2015089492 A2 | 6/2015 |
| WO | WO-2015122995 A1 | 8/2015 |
| WO | WO-2015123362 A1 | 8/2015 |
| WO | WO-2016012800 A1 | 1/2016 |
| WO | WO-2016098357 A1 | 6/2016 |
| WO | WO-2016125495 A1 | 8/2016 |
| WO | WO2016130516 A1 | 8/2016 |
| WO | WO-2016148653 A1 | 9/2016 |
| WO | WO-2017046994 A1 | 3/2017 |
| WO | WO-2017212291 A1 | 12/2017 |
| WO | WO-2018025982 A1 | 2/2018 |

OTHER PUBLICATIONS

U.S. Appl. No. 13/257,112, filed Nov. 22, 2011, Igawa et al.
U.S. Appl. No. 13/257,145, filed Nov. 22, 2011, Igawa et al.
U.S. Appl. No. 14/680,250, filed Apr. 7, 2015, Igawa et al.
U.S. Appl. No. 14/962,293, filed Dec. 8, 2015, Igawa et al.
U.S. Appl. No. 15/015,287, filed Feb. 4, 2016, Igawa et al.
U.S. Appl. No. 15/614,842, filed Jun. 6, 2017, Igawa et al.
U.S. Appl. No. 15/976,288, filed May 10, 2018, Igawa et al.
U.S. Appl. No. 16/298,032, filed Mar. 11, 2019, Igawa et al.
U.S. Appl. No. 16/323,142, filed Feb. 4, 2019, Kakiuchi et al.
U.S. Appl. No. 17/530,542, filed Nov. 19, 2021, Igawa et al.
U.S. Appl. No. 17/720,937, filed Apr. 14, 2022, Igawa et al.
U.S. Appl. No. 16/333,736, filed Mar. 15, 2019, Sampei et al.
U.S. Appl. No. 16/435,979, filed Jun. 10, 2019, Sampei et al.
U.S. Appl. No. 16/697,310, filed Nov. 27, 2019, Igawa et al.
U.S. Appl. No. 16/980,611, filed Sep. 14, 2020, Fink et al.
U.S. Appl. No. 17/333,256, filed May 28, 2021, Kakiuchi et al.
U.S. Appl. No. 17/494,199, filed Oct. 5, 2021, Igawa et al.
Allen, M.J., et al., "Interchain Disulfide Bonding in Human IgG2 Antibodies Probed by Site-Directed Mutagenesis," Biochemistry 48(17):3755-3766, American Chemical Society, United States (May 2009).
Almagro, J.C. and Fransson, J., "Humanization of Antibodies," Frontiers in BioScience 13:1619-1633, Frontiers In Bioscience Publications, United States (Jan. 2008).

*Amgen vs Sanofi and Regeneron*; Case:17-1480 Document:178 filed Feb. 6, 2018.
Armour, K.L., et al., "Recombinant Human IgG Molecules Lacking Fcgamma Receptor I Binding and Monocyte Triggering Activities," European Journal of Immunology, 29(8):2613-2624, Wiley-VCH, Germany (Aug. 1999).
Ausubel, F.M., et al., "Current Protocols in Molecular Biology," John Wiley & Sons Inc., Dec. 4, 2003, 4648 pages.
Baca, M., et al., "Antibody Humanization Using Monovalent Phage Display," The Journal of Biological Chemistry 272(16):10678-10684, American Society for Biochemistry and Molecular Biology, United States (Apr. 1997).
Becker, J.M., et al., "Prevention of Postoperative Abdominal Adhesions by a Sodium Hyaluronate-based Bioresorbable Membrane: a Prospective, Randomized, Double-blind Multicenter Study," Journal of the American College of Surgeons 183(4):297-306, Elsevier, United States (Oct. 1996).
Bian, H., et al., "Discovery of Promiscuous HLA-II-Restricted T Cell Epitopes With TEPITOPE," Methods 34(4):468-475, Academic Press, United States (Dec. 2004).
Boerner, P., et al., "Production of Antigen-specific Human Monoclonal Antibodies From in Vitro-Primed Human Splenocytes," Journal of Immunology 147(1):86-95, American Association of Immunologists, United States (Jul. 1991), Abstract.
Borrok, M.J., et al., "pH-Dependent Binding Engineering Reveals an FcRn Affinity Threshold That Governs IgG Recycling," The Journal of Biological Chemistry 290(7):4282-4290, American Society for Biochemistry and Molecular Biology, United States (Feb. 2015).
Brenner, S.E., "Errors in Genome Annotation," Trends in Genetics 15(4):132-133, Elsevier Trends Journals, England (Apr. 1999).
Brooks, D.G., et al., "Structure and Expression of Human IgG FcRII(CD32). Functional Heterogeneity is Encoded by the Alternatively Spliced Products of Multiple Genes," The Journal of Experimental Medicine 170(4):1369-1385, Rockefeller University Press, United States (Oct. 1989).
Bruggemann, M., et al., "Comparison of the Effector Functions of Human Immunoglobulins Using a Matched Set of Chimeric Antibodies," The Journal of Experimental Medicine 166(5):1351-1361, Rockefeller University Press, United States (Nov. 1987).
Bulun, S.E., "Endometriosis," The New England Journal of Medicine 360(3):268-279, Massachusetts Medical Society, United States (Jan. 2009).
Canfield, S.M. and Morrison, S.L., "The Binding Affinity of Human IgG for Its High Affinity Fc Receptor is Determined by Multiple Amino Acids in the CH2 Domain and is Modulated by the Hinge Region," The Journal of Experimental Medicine 173(6):1483-1491, Rockefeller University Press, United States (Jun. 1991).
Carter, P., et al., "Humanization of an Anti-P185HER2 Antibody for Human Cancer Therapy," Proceedings of the National Academy of Sciences of the United States of America 89(10):4285-4289, National Academy of Sciences, United States (May 1992).
Chan, K.R., et al., "Therapeutic Antibodies as a Treatment Option for Dengue Fever," Expert Review of Anti-infective Therapy 11(11):1147-1157, Oxford, London (Nov. 2013), Abstract.
Chappel, M.S., et al., "Identification of a Secondary Fc Gamma RI Binding Site Within a Genetically Engineered Human IgG Antibody," The Journal of Biological Chemistry 268(33):25124-25131, American Society for Biochemistry and Molecular Biology, United States (Nov. 1993).
Chappel, M.S., et al., "Identification of the Fc Gamma Receptor Class I Binding Site in Human IgG Through the Use of Recombinant IgG1/IgG2 Hybrid and Point-Mutated Antibodies," Proceedings of the National Academy of Sciences of the United States of America 88(20):9036-9040, National Academy of Sciences, United States (Oct. 1991).
Chari, R.V., et al., "Immunoconjugates Containing Novel Maytansinoids: Promising AntiCancer Drugs," Cancer Research 52(1):127-131, American Association for Cancer Research, United States (Jan. 1992).
Chau, L.A., et al., "HuM291 (Nuvion), a Humanized Fc Receptor-Nonbinding Antibody Against CD3, Anergizes Peripheral Blood T

(56) References Cited

OTHER PUBLICATIONS

Cells as Partial Agonist of the T Cell Receptor," Transplantation 71(7):941-950, Lippincott Williams & Wilkins, United States (Apr. 2001).

Chen, C., et al., "Enhancement and destruction of antibody function by somatic mutation: unequal occurrence is controlled by V gene combinatorial associations," The EMBO Journal 14(12):2784-2794 (1995).

Chen, Y., et al., "Selection and Analysis of an Optimized Anti-VEGF Antibody: Crystal Structure of an Affinity-Matured Fab in Complex With Antigen," Journal of Molecular Biology 293(4):865-881, Elsevier, England (Nov. 1999).

Chothia, C. and Lesk A.M., "Canonical Structures for the Hypervariable Regions of Immunoglobulins," Journal of Molecular Biology 196(4):901-917, Academic Press, England (Aug. 1987).

Chu, G.C., et al., "Accumulation of Succinimide in a Recombinant Monoclonal Antibody in Mildly Acidic Buffers Under Elevated Temperatures," Pharmaceutical Research 24(6):1145-1156, Kluwer Academic/Plenum Publishers, United States (Jun. 2007).

Clackson, T., et al., "Making Antibody Fragments Using Phage Display Libraries," Nature 352(6336):624-628, Nature Publishing Group, England (Aug. 1991).

Clynes, R., et al., "Fc Receptors Are Required in Passive and Active Immunity to Melanoma," Proceedings of the National Academy of Sciences of the United States of America 95(2):652-656, National Academy of Sciences, United States (Jan. 1998).

Clynes, R.A., et al., "Inhibitory Fc Receptors Modulate in Vivo Cytotoxicity Against Tumor Targets," Nature Medicine 6(4):443-446, Nature Publishing Company, United States (Apr. 2000).

Cole, M.S., et al., "Human IgG2 Variants of Chimeric Anti-CD3 are Nonmitogenic to T Cells," Journal of Immunology 159(7):3613-3621, American Association of Immunologists, United States (Oct. 1997).

Coligan, J.E., et al., "Current Protocols in Immunology," John Wiley and Sons, 1991.

Collins, F.S., et al., "Generation and Initial Analysis of More Than 15,000 Full-length Human and Mouse cDNA Sequences," Proceedings of the National Academy of Sciences of the United States of America 99(26):16899-16903, National Academy of Sciences, United States (Dec. 2002).

Cordoba, A.J., et al., "Non-Enzymatic Hinge Region Fragmentation of Antibodies in Solution," Journal of Chromatography B 818(2):115-121, Elsevier, Netherlands (Apr. 2005).

Cragg, M.S. and Glennie, M.J., "Antibody Specificity Controls in Vivo Effector Mechanisms of Anti-CD20 Reagents," Blood 103(7):2738-2743, American Society of Hematology, United States (Apr. 2004).

Cragg, M.S., et al., "Complement-mediated Lysis by Anti-CD20 mAb Correlates With Segregation Into Lipid Rafts," Blood 101(3):1045-1052, American Society of Hematology, United States (Feb. 2003).

Dall'acqua, W.F., et al., "Antibody Humanization by Framework Shuffling," Methods 36(1):43-60, Academic Press, United States (May 2005).

Dall'acqua, W.F., et al., "Increasing the Affinity of a Human IgG1 for the Neonatal Fc Receptor: Biological Consequences," Journal of Immunology 169(9):5171-5180, American Association of Immunologists, United States (Nov. 2002).

Dall'acqua, W.F., et al., "Modulation of the Effector Functions of a Human IgG1 Through Engineering of Its Hinge Region," Journal of Immunology, 177(2):1129-1138, American Association of Immunologists, United States (Jul. 2006).

Dall'acqua, W.F., et al., "Properties of Human IgG1s Engineered for Enhanced Binding to the Neonatal Fc Receptor (FcRn)," The Journal of Biological Chemistry 281(33):23514-23524, American Society for Biochemistry and Molecular Biology, United States (Aug. 2006).

Daëron, M., "Fc Receptor Biology," Annual Review of Immunology 15:203-234, Annual Reviews Inc., United States (1997), Abstract.

Datta-Mannan, A., et al., "Monoclonal Antibody Clearance. Impact of Modulating the Interaction of IgG With the Neonatal Fc Receptor," The Journal of Biological Chemistry 282(3):1709-1717, American Society for Biochemistry and Molecular Biology, United States (Jan. 2007).

De Groot, A.S. and Martin W., et al., "Reducing Risk, Improving Outcomes: Bioengineering Less Immunogenic Protein Therapeutics," Clinical Immunology 131(2):189-201, Academic Press, United States (May 2009).

Deng, R., et al., "Pharmacokinetics of Humanized Monoclonal Anti-tumor Necrosis Factor-{alpha} Antibody and Its Neonatal Fc Receptor Variants in Mice and Cynomolgus Monkeys," Drug Metabolism and Disposition 38(4):600-605, American Society for Pharmacology and Experimental, United States (Apr. 2010).

Desai, D.D., et al., "Fc Gamma Receptor IIB on Dendritic Cells Enforces Peripheral Tolerance by Inhibiting Effector T Cell Responses," Journal of Immunology 178(10):6217-6226, American Association of Immunologists, United States (May 2007).

Devita, V.T., et al., "Cancer: Principles and Practice of Oncology," J.B. Lippincott Company, 1993.

Dhiman, N., et al., "Gene Expression Microarrays: A 21st Century Tool for Directed Vaccine Design," Vaccine 20(1-2):22-30, Elsevier Science, Netherlands (Oct. 2001).

Dillon, T. M., et al., "Structural and Functional Characterization of Disulfide Isoforms of the Human IgG2 Subclass," The Journal of Biological Chemistry, 283(23):16206-16215, American Society for Biochemistry and Molecular Biology, United States (Jun. 2008).

Donnez, J., et al., "Current thinking on the pathogenesis of endometriosis," Gynecologic and Obstetric Investigation 54 Suppl 1:52-58, discussion 59-62, Karger, Switzerland (2002).

Duncan, A.R. and Winter, G., "The Binding Site for C1q on IgG," Nature 332(6166):738-740, Nature Publishing Group, England (Apr. 1988), Abstract.

Ejima, D., et al., "Effects of Acid Exposure on the Conformation, Stability, and Aggregation of Monoclonal Antibodies," Proteins 66(4):954-962, Wiley-Liss, United States (Mar. 2007).

Fellouse, F.A., et al., "Synthetic Antibodies From a Four-Amino-Acid Code: a Dominant Role for Tyrosine in Antigen Recognition," Proceedings of the National Academy of Sciences of the United States of America 101(34):12467-12472, National Academy of Sciences, United States (Aug. 2004).

Flatman, S., et al., "Process Analytics for Purification of Monoclonal Antibodies," Journal of Chromatography B 848(1):79-87, Elsevier, Netherlands (Mar. 2007), Abstract.

Gazzano-Santoro H., et al., "A Non-Radioactive Complement-Dependent Cytotoxicity Assay for Anti-CD20 Monoclonal Antibody," Journal of Immunological Methods 202(2):163-171, Elsevier, Netherlands (Mar. 1997).

GenBank Accession No. AAG00910.2, Recombinant IgG2 Heavy Chain, Partial [*Homo Sapiens*], May 14, 2001.

Geneseq Accession No. AEM45140, Light Chain Constant Region of Therapeutic Human IgG Antibody, Feb. 22, 2007.

Geneseq Accession No. ARZ17615, Human Antibody IgG2 Heavy Chain Constant Region, Seq Id No. 36, Aug. 21, 2008.

Gerngross, T.U., "Advances in the Production of Human Therapeutic Proteins in Yeasts and Filamentous Fungi," Nature Biotechnology 22(11):1409-1414, Nature America Publishing, United States (Nov. 2004).

Gessner, J.E., et al., "The IgG Fc Receptor Family," Annals of Hematology 76(6):231-248, Springer Verlag, Germany (Jun. 1998).

Ghetie, V. and Ward, E.S., "Fcrn: the Mhc Class I-related Receptor That is More Than an IgG Transporter," Immunology Today 18(12):592-598, Elsevier Science Publishers, England (Dec. 1997).

Ghetie, V., et al., "Increasing the Serum Persistence of an IgG Fragment by Random Mutagenesis," Nature Biotechnology 15(7):637-640, Nature America Publishing, United States (Jul. 1997).

Giudice, L.C., et al., "Endometriosis," Lancet 364(9447):1789-1799, Elsevier, London (Nov. 2004).

Graham, F.L., et al., "Characteristics of a Human Cell Line Transformed by Dna From Human Adenovirus Type 5," The Journal of General virology 36(1):59-72, Microbiology Society, England (Jul. 1977).

Griffiths, A.D., et al., "Human Anti-Self Antibodies With High Specificity From Phage Display Libraries," The EMBO Journal 12(2):725-734, Wiley Blackwell, England (Feb. 1993).

(56) References Cited

OTHER PUBLICATIONS

Gruber, M., et al., "Efficient Tumor Cell Lysis Mediated by a Bispecific Single Chain Antibody Expressed in *Escherichia coli*," Journal of Immunology 152(11):5368-5374, American Association of Immunologists, United States (Jun. 1994).

Guo, S.W., "Recurrence of Endometriosis and Its Control," Human Reproduction Update 15(4):441-461, Published for the European Society of Human Reproduction and Embryology by Oxford University Press, England (Jul.-Aug. 2009).

Guyre, P.M., et al., "Increased Potency of Fc-Receptor-Targeted Antigens," Cancer Immunology 45(3-4):146-148, Springer Verlag, Germany (Nov.-Dec. 1997).

Hashimoto-Gotoh, T., et al., "An Oligodeoxyribonucleotide-directed Dual Amber Method for Site-directed Mutagenesis," Gene 152(2):271-275, Elsevier/North-Holland, Netherlands (Jan. 1995), Abstract.

Hellstrom, I., et al., "Antitumor Effects of L6, an IgG2a Antibody That Reacts With Most Human Carcinomas," Proceedings of the National Academy of Sciences of the United States of America 83(18):7059-7063, National Academy of Sciences, United States (Sep. 1986).

Hellstrom, I., et al., "Strong Antitumor Activities of lgG3 Antibodies to a Human Melanoma-associated Ganglioside," Proceedings of the National Academy of Sciences of the United States of America 82(5):1499-1502, National Academy of Sciences, United States (Mar. 1985).

Hinman, L.M., et al., "Preparation and Characterization of Monoclonal Antibody Conjugates of the Calicheamicins: a Novel and Potent Family of Antitumor Antibiotics," Cancer Research 53(14):3336-3342, American Association for Cancer Research, United States (Jul. 1993).

Hinton, P.R., et al., "An Engineered Human IgG1 Antibody With Longer Serum Half-life," Journal of Immunology, 176(1):346-356, American Association of Immunologists, United States (Jan. 2006).

Hinton, P.R., et al., "Engineered Human IgG Antibodies With Longer Serum Half-lives in Primates," The Journal of Biological Chemistry 279(8):6213-6216, American Society for Biochemistry and Molecular Biology, United States (Feb. 2004).

Holash, J., et al., "Vegf-Trap: A Vegf Blocker With Potent Antitumor Effects," Proceedings of the National Academy of Sciences of the United States of America 99(7):11393-11398, National Academy of Sciences, United States (Aug. 2002).

Hollinger, P., et al., ""Diabodies": Small Bivalent and Bispecific Antibody Fragments," Proceedings of the National Academy of Sciences of the United States of America 90(14):6444-6448, National Academy of Sciences, United States (Jul. 1993).

Hudson, P.J., et al., "Engineered Antibodies," Nature Medicine 9(1):129-134, Nature Publishing Company, United States (Jan. 2003).

Idusogie, E.E., et al., "Mapping of the C1q Binding Site on Rituxan, a Chimeric Antibody With a Human IgG1 Fc," Journal of Immunology 164(8):4178-4184, American Association of Immunologists, United States (Apr. 2000).

Igawa, T., et al., "Antibody Recycling by Engineered pH-Dependent Antigen Binding Improves the Duration of Antigen Neutralization," Nature Biotechnology 28(11):1203-1207, Nature America Publishing, United States (Nov. 2010).

Iwabe, T., et al., "Pathogenetic Significance of Increased Levels of Interleukin-8 in the Peritoneal Fluid of Patients With Endometriosis," Fertility and Sterility 69(5):924-930, Elsevier for the American Society for Reproductive Medicine, New York (May 1998).

Jefferis, R and Lund, J., "Interaction Sites on Human IgG-Fc for FcgammaR: Current Models," Immunology Letters, 82(1-2):57-65, Elsevier/North-Holland Biomedical Press, Netherlands (Jun. 2002).

Johnson, K.A., et al., "Cation Exchange-HPLC and Mass Spectrometry Reveal C-Terminal Amidation of an IgG1 Heavy Chain," Analytical Biochemistry 360(1):75-83, Academic Press, United States (Jan. 2007).

Kabat, E.A., et al., "Sequences of Proteins of Immunological Interest," National Institute of Health, Publ'n No. 91-3242, 5th ed. 1991, vol. 1, pp. 647-660.

Kam, N.W., et al., "Carbon Nanotubes as Multifunctional Biological Transporters and Near-Infrared Agents for Selective Cancer Cell Destruction," Proceedings of the National Academy of Sciences of the United States of America 102(33):11600-11605, National Academy of Sciences, United States (Aug. 2005).

Kanda, Y., et al., "Comparison of Cell Lines for Stable Production of Fucose-Negative Antibodies With Enhanced ADCC," Biotechnology and Bioengineering 94(4):680-688, Wiley, United States (Jul. 2006), Abstract.

Kashmiri, S.V., et al., "SDR Grafting—a New Approach to Antibody Humanization," Methods 36(1):25-34, Academic Press, United States (May 2005), Abstract.

Kim, S.J., et al., "Antibody Engineering for the Development of Therapeutic Antibodies," Molecules and Cells 20(1):17-29, Korean Society for Molecular and Cellular Biology, Korea (Aug. 2005).

King, H.D., et al., "Monoclonal Antibody Conjugates of Doxorubicin Prepared With Branched Peptide Linkers: Inhibition of Aggregation by Methoxytriethyleneglycol Chains," Journal of Medicinal Chemistry 45(19):4336-4343, American Chemical Society, United States (Sep. 2002), Abstract.

Klimka, A., et al., "Human Anti-CD30 Recombinant Antibodies by Guided Phage Antibody Selection Using Cell Panning," British Journal of Cancer 83(2):252-260, Nature Publishing Group on behalf of Cancer Research UK, England (Jul. 2000).

Kohler, G. and Milstein, C., "Continuous Cultures of Fused Cells Secreting Antibody of Predefined Specificity," Nature 256(5517):495-497, Nature Publishing Group, England (Aug. 1975).

Kono, H., et al., "FcgammaRIIB Ile232Thr Transmembrane Polymorphism Associated With Human Systemic Lupus Erythematosus Decreases Affinity to Lipid Rafts and Attenuates Inhibitory Effects on B Cell Receptor Signaling," Human Molecular genetics 14(19):2881-2892, IRL Press at Oxford University Press, England (Oct. 2005).

Kostelny, S.A., et al., "Formation of a Bispecific Antibody by the Use of Leucine Zippers," Journal of Immunology 148(5):1547-1553, American Association of Immunologists, United States (Mar. 1992), Abstract.

Kozbor, D., "A Human Hybrid Myeloma for Production of Human Monoclonal Antibodies," Journal of Immunology 133(6):3001-3005, American Association of Immunologists, United States (Dec. 1984), Abstract.

Kramer, W., et al., "The Gapped Duplex Dna Approach to Oligonucleotide-directed Mutation Construction," Nucleic Acids Research 12(24):9441-9456, Oxford University Press, England (Dec. 1984), Abstract.

Kunkel, T.A., "Rapid and Efficient Site-specific Mutagenesis Without Phenotypic Selection," Proceedings of the National Academy of Sciences of the United States of America 82(2):488-492, National Academy of Sciences, United States (Jan. 1985).

Kyogoku, C., et al., "Fcgamma Receptor Gene Polymorphisms in Japanese Patients With Systemic Lupus Erythematosus: Contribution of Fcgr2b to Genetic Susceptibility," Arthritis and Rheumatism 46(5):1242-1254, Wiley-Blackwell, United States (May 2002).

Lazar, G.A., et al., "Engineered Antibody Fc Variants With Enhanced Effector Function," Proceedings of the National Academy of Sciences of the United States of America, 103(11):4005-4010, National Academy of Sciences, United States (Mar. 2006).

Lee, C.V., et al., "High-Affinity Human Antibodies From Phage-displayed Synthetic Fab Libraries With a Single Framework Scaffold," Journal of Molecular Biology 340(5):1073-1093, Elsevier, England (Jul. 2004).

Li, F. and Ravetch, J.V., "Apoptotic and Antitumor Activity of Death Receptor Antibodies Require Inhibitory Fcγ Receptor Engagement," Proceedings of the National Academy of Sciences of the United States of America 109(27):10966-10971, National Academy of Sciences, United States (Jul. 2012).

Li, H., et al., "Optimization of Humanized IgGs in Glycoengineered Pichia Pastoris," Nature Biotechnology 24(2):210-215, Nature America Publishing, United States (Feb. 2006), Abstract.

Li, J., et al., "Human Antibodies for Immunotherapy Development Generated via a Human B Cell Hybridoma Technology," Proceed-

(56) References Cited

OTHER PUBLICATIONS ings of the National Academy of Sciences of the United States of America 103(10):3557-3562, National Academy of Sciences, United States (Feb.-Mar. 2006).
Li, X., et al., "A Novel Polymorphism in the Fcgamma Receptor IIB (CD32B) Transmembrane Region Alters Receptor Signaling," Arthritis and Rheumatism 48(11):3242-3252, Wiley-Blackwell, United States (Nov. 2003).
Lode, H.N., et al., "Targeted Therapy with a Novel Enediyene Antibiotic Calicheamicin Theta(I)1 Effectively Suppresses Growth and Dissemination of Liver Metastases in a Syngeneic Model of Murine Neuroblastoma," Cancer Research 58(14):2925-2928, American Association for Cancer Research, Chicago (Jul. 1998).
Lonberg, N., "Fully Human Antibodies From Transgenic Mouse and Phage Display Platforms," Current Opinion in Immunology 20(4):450-459, Elsevier, England (Aug. 2008).
Lonberg, N., "Human Antibodies From Transgenic Animals," Nature Biotechnology 23(9):1117-1125, Nature America Publishing, United States (Sep. 2005).
Lund, J., et al., "Expression and Characterization of Truncated Forms of Humanized L243 IgG1. Architectural Features Can Influence Synthesis of Its Oligosaccharide Chains and Affect Superoxide Production TrIgGered Through Human Fcgamma Receptor I," European Journal of Biochemistry 267(24): 7246-7257, Blackwell Science Ltd. on behalf of the Federation of European Biochemical Societies, England (Dec. 2000).
MacCallum, R.M., et al., "Antibody-antigen Interactions: Contact Analysis and Binding Site Topography," Journal of Molecular Biology 262(5):732-745, Academic Press, England (Oct. 1996).
Marks, J.D., et al., "By-Passing Immunization. Human Antibodies From V-Gene Libraries Displayed on Phage," Journal of Molecular Biology 222(3):581-597, Elsevier, England (Dec. 1991).
Martinez, T., et al., "Disulfide Connectivity of Human Immunoglobulin G2 Structural Isoforms," Biochemistry 47(28):7496-7508, American Chemical Society, United States (Jul. 2008).
Mather. J.P., "Establishment and Characterization of Two Distinct Mouse Testicular Epithelial Cell Lines," Biology of Reproduction 23(1):243-252, Oxford University Press, United States (Aug. 1980).
McCafferty, J., et al., "Phage Antibodies: Filamentous Phage Displaying Antibody Variable Domains," Nature 348(6301):552-554, Nature Publishing Group, England (Dec. 1990).
Milstein, C. and Cuello, A.C., "Hybrid Hybridomas and Their Use In Immunohistochemistry," Nature 305:537-540, Nature Publishing Group, England (Oct. 1983).
Morrison, S.L., et al., "Chimeric Human Antibody Molecules: Mouse Antigen-binding Domains With Human Constant Region Domains," Proceedings of the National Academy of Sciences of the United States of America 81(21):6851-6855, National Academy of Sciences, United States (Nov. 1984).
Munson, P.J. and Rodbard, D., "Ligand: a Versatile Computerized Approach for Characterization of Ligand-binding Systems," Analytical Biochemistry 107(1):220-239, Elsevier, United States (Sep. 1980), Abstract.
Nagy, A., et al., "Stability of Cytotoxic Luteinizing Hormone-releasing Hormone Conjugate (AN-152) Containing Doxorubicin 14-O-hemiglutarate in Mouse and Human Serum in Vitro: Implications for the Design of Preclinical Studies," Proceedings of the National Academy of Sciences of the United States of America 97(2):829-834, National Academy of Sciences, United States (Jan. 2000).
Newman, R., et al., "Modification of the Fc Region of a Primatized IgG Antibody to Human Cd4 Retains Its Ability to Modulate Cd4 Receptors but Does Not Deplete Cd4(+) T Cells in Chimpanzees," Clinical Immunology 98(2):164-174, Academic Press, United States (Feb. 2001).
Okazaki, A., et al., "Fucose Depletion From Human IgG1 Oligosaccharide Enhances Binding Enthalpy and Association Rate Between IgG1 and FcgammaRIIIa," Journal of Molecular biology 336(5):1239-1249, Elsevier, England (Mar. 2004), Abstract.
Ory, P.A., et al., "Sequences of Complementary DNAs That Encode the NA1 and NA2 Forms of Fc Receptor III on Human Neutrophils," Journal of Clinical Investigation 84(5):1688-1691, American Society for Clinical Investigation, United States (Nov. 1989).
Pace, C.N., et al., "How to Measure and Predict the Molar Absorption Coefficient of a Protein," Protein Science 4(11):2411-2423, Cold Spring Harbor Laboratory Press, United States (Nov. 1995).
Padlan, E.A., "A Possible Procedure for Reducing the Immunogenicity of Antibody Variable Domains While Preserving Their Ligand-Binding Properties," Molecular Immunology 28(4-5):489-498, Pergamon Press, England (Apr.-May 1991), Abstract.
Pakula, A. A. and Sauer, R. T., "Genetic Analysis of Protein Stability and Function," Annu Rev Genet 23:289-310 (1989).
Pavlou, A.K. and Belsey, M.J., "The Therapeutic Antibodies Market to 2008," European Journal of Pharmaceutics and Biopharmaceutics, 59(3):389-396, Elsevier Science, Netherlands (Apr. 2005).
Petkova, S.B., et al., "Enhanced Half-life of Genetically Engineered Human IgG1 Antibodies in a Humanized Forn Mouse Model: Potential Application in Humorally Mediated Autoimmune Disease," International Immunology 18(12):1759-1769, Oxford University Press, England (Dec. 2006).
Portolano, S., et al., "Lack of Promiscuity in Autoantigen-specific H and L Chain Combinations as Revealed by Human H and L Chain "Roulette".," Journal of Immunology 150(3):880-887, American Association of Immunologists, United States (Feb. 1993).
Presta, L.G., "Molecular Engineering and Design of Therapeutic Antibodies," Current Opinion in Immunology, 20(4):460-470, Elsevier, England (Aug. 2008).
Presta, L.G., "Engineering of Therapeutic Antibodies to Minimize Immunogenicity and Optimize Function," Advanced drug delivery Reviews 58(5-6) :640-656, Elsevier Science Publishers, Netherlands (Aug. 2006).
Presta, L.G., et al., "Humanization of an Antibody Directed Against IgE," Journal of Immunology 151(5):2623-2632, American Association of Immunologists, United States (Sep. 1993), Abstract.
Presta, L.G., et al., "Humanization of an Anti-Vascular Endothelial Growth Factor Monoclonal Antibody for the Therapy of Solid Tumors and Other Disorders," Cancer Research 57(20):4593-4599, American Association for Cancer Research, United States (Oct. 1997).
Queen, C., et al., "A Humanized Antibody That Binds to the Interleukin 2 Receptor," Proceedings of the National Academy of Sciences of the United States of America, 86(24):10029-10033, National Academy of Sciences, United States (Dec. 1989).
Rajpal, A., et al., "A General Method for Greatly Improving the Affinity of Antibodies by Using Combinatorial Libraries," Proceedings of the National Academy of Sciences of the United States of America 102(24):8466-8471, National Academy of Sciences, United States (Jun. 2005).
Ravetch, J.V. and Kinet, J.P., "Fc Receptors," Annual Review of Immunology 9:457-492, Annual Reviews Inc, United States (1991).
Reddy, M.P., et al., "Elimination of Fc Receptor-dependent Effector Functions of a Modified IgG4 Monoclonal Antibody to Human Cd4," Journal of Immunology 164(4):1925-1933, American Association of Immunologists, United States (Feb. 2000).
Reichert, J.M., et al., "Monoclonal Antibody Successes in the Clinic," Nature Biotechnology, 23(9):1073-1078, Nature America Publishing, United States (Sep. 2005).
Reist, C.J., et al., "Human IgG2 Constant Region Enhances in Vivo Stability of Anti-tenascin Antibody 81c6 Compared With Its Murine Parent," Clinical Cancer Research 4(10):2495-2502, The Association, United States (Oct. 1998).
Riechmann, L., et al., "Reshaping Human Antibodies for Therapy," Nature 332(6162):323-329, Nature Publishing Group, England (Mar. 1988).
Rosok, M.J., et al., "A Combinatorial Library Strategy for the Rapid Humanization of Anticarcinoma BR96 Fab," The Journal of Biological Chemistry 271(37):22611-22618, American Society for Biochemistry and Molecular Biology, United States (Sep. 1996).
Rudikoff, S., et al. "Single amino acid substitution altering antigen-binding specificity," Proc Natl Acad Sci 79:1979-1983 (1982).

(56) References Cited

OTHER PUBLICATIONS

Russo, R.C., et al., "The Cxcl8/il-8 Chemokine Family and Its Receptors in Inflammatory Diseases," Expert Review of clinical Immunology 10(5):593-619, Oxford, London (May 2014).
Salfeld, J. G., "Isotype Selection in Antibody Engineering," Nature Biotechnology, 25(12):1369-1372, Nature America Publishing, United States (Dec. 2007).
Scappaticci, F.A., et al., "Arterial Thromboembolic Events in Patients With Metastatic Carcinoma Treated With Chemotherapy and Bevacizumab," Journal of the National Cancer Institute 99(16):1232-1239, Oxford University Press, United States (Aug. 2007).
Shields, R. L., et al., "High Resolution Mapping of the Binding Site on Human IgG1 for Fc Gamma RI, Fc Gamma RIII, Fc Gamma RIII, and FcRn and Design of Igg1 Variants With Improved Binding to the Fc Gamma R," The Journal of Biological Chemistry, 276(9):6591-6604, American Society for Biochemistry and Molecular Biology, United States (Mar. 2001).
Shinkawa, T., et al., "The Absence of Fucose but Not the Presence of Galactose or Bisecting N-acetylglucosamine of Human IgG1 Complex-type Oligosaccharides Shows the Critical Role of Enhancing Antibody-dependent Cellular Cytotoxicity," The Journal of Biological Chemistry 278(5):3466-3473, American Society for Biochemistry and Molecular Biology, United States (Jan. 2003).
Shire, S.J., et al., "Challenges in the Development of High Protein Concentration Formulations," Journal of Pharmaceutical Sciences 93(6):1390-1402, American Pharmaceutical Assn, United States (Jun. 2004).
Sidhu, S.S., et al., "Phage-Displayed Antibody Libraries of Synthetic Heavy Chain Complementarity Determining Regions," Journal of Molecular biology 338(2):299-310, Elsevier, England (Apr. 2004).
Smith, T.F., et al., "The Challenges of Genome Sequence Annotation or "the Devil is in the Details"," Nature Biotechnology 15(12):1222-1223, Nature America Publishing, New York (Nov. 1997).
Smolen, U.S., et al., "Interleukin-6: a New Therapeutic Target," Arthritis Research & therapy 8 Suppl 2:S5, BioMed Central, England (Jul. 2006).
Story, C.M., et al., "A Major Histocompatibility Complex Class I-like Fc Receptor Cloned From Human Placenta: Possible Role in Transfer of Immunoglobulin G From Mother to Fetus," Journal of Experimental Medicine 180(6):2377-2381, Rockefeller University Press, United States (Dec. 1994).
Strand, V., et al., "Biologic Therapies in Rheumatology: Lessons Learned, Future Directions," Nature Reviews. Drug discovery 6(1):75-92, Nature Pub. Group, England (Jan. 2007).
Tan, G.K., et al., "A Non Mouse-adapted Dengue Virus Strain as a New Model of Severe Dengue Infection in AG129 Mice," PLOS Neglected Tropical Diseases 4(4):e672, Public Library of Science, United States (Apr. 2010).
Tarantul, V. Z., "Explanatory Biotechnological Dictionary. Russian-English," Languages of Slavic Cultures, p. 72 (2009).
Thies, M.J., et al., "The Alternatively Folded State of the Antibody C(H)3 Domain," Journal of Molecular biology 309(5):1077-1085, Academic Press, England (Jun. 2001).
Torgov, M.Y., et al., "Generation of an Intensely Potent Anthracycline by a Monoclonal Antibody-beta-galactosidase Conjugate," Bioconjugate Chemistry 16(3):717-721, American Chemical Society, United States (May 2005), Abstract.
Traunecker, A., et al., "Bispecific Single Chain Molecules (Janusins) Target Cytotoxic Lymphocytes on Hiv Infected Cells," The EMBO Journal 10(12):3655-3659, Wiley Blackwell, England (Dec. 1991).
Tsubaki, M., et al., "C-terminal Modification of Monoclonal Antibody Drugs: Amidated Species as a General Product-related Substance," International Journal of Biological MacroMolecules 52:139-147, IPC Science and Technology Press, Netherlands (Jan. 2013).
Tutt, A., et al., "Trispecific F(Ab')3 Derivatives That Use Cooperative Signaling via the TCR/CD3 Complex and CD2 to Activate and Redirect Resting Cytotoxic T Cells," Journal of Immunology 147(1):60-69, American Association of Immunologists, United States (Jul. 1991), Abstract.

Urlaub G. and Chasin, L.A., "Isolation of Chinese Hamster Cell Mutants Deficient in Dihydrofolate Reductase Activity," Proceedings of the National Academy of Sciences of the United States of America 77(7):4216-4220, National Academy of Sciences, United States (Jul. 1980).
Vaccaro, C., et al., "Divergent Activities of an Engineered Antibody in Murine and Human Systems Have Implications for Therapeutic Antibodies," Proceedings of the National Academy of Sciences of the United States of America 103(49):18709-18714, National Academy of Sciences, United States (Dec. 2006).
Vercellini, et al., "Postoperative Oral Contraceptive Exposure and Risk of Endometrioma Recurrence," American Journal of Obstetrics and Gynecology 198(5):504, Elsevier, United States (May 2008).
Vincent, K. J. and Zurini, M., "Current strategies in antibody engineering: Fc engineering and pH-dependent antigen binding, bispecific antibodies and antibody drug conjugates," Biotechnol J., 7:1444-1450 (2012).
Vollmers, H.P. and Brandlein, S., "The "Early Birds": Natural IgM Antibodies and Immune Surveillance," Histology and Histopathology 20(3):927-937, Histology and Histopathology, Spain (Jul. 2005).
Wally, J., et al., "Identification of a Novel Substitution in the Constant Region of a Gene Coding for an Amyloidogenic Kappa$_1$ Light Chain," Biochimica et Biophysica Acta 1454(1):49- 56, Elsevier Pub. Co., Netherlands (May 1999).
Wang, Q.C., et al., "Polyethylene Glycol-modified Chimeric Toxin Composed of Transforming Growth Factor Alpha and Pseudomonas Exotoxin," Cancer Research 53(19):4588-4594, American Association for Cancer Research, Chicago (Oct. 1993).
Warmerdam, P.A., et al., "Molecular Basis for a Polymorphism of Human Fc Gamma Receptor II (CD32)," Journal of Experimental Medicine 172(1):19-25, Rockefeller University Press, United States (Jul. 1990).
Winter, G., et al., "Making Antibodies by Phage Display Technology," Annual Review of Immunology 12:433-455, Annual Reviews Inc., United States (1994), Abstract.
Wright, A., et al., "Effect of Glycosylation on Antibody Function: Implications for Genetic Engineering," Trends in Biotechnology 15(1):26-32, Elsevier Science Publishers, England (Jan. 1997), Abstract.
Wu, J., et al., "A Novel Polymorphism of FcgammaRIIIa (CS16) Alters Receptor Function and Predisposes to Autoimmune Disease," Journal of Clinical Investigation 100(5):1059-1070, American Society for Clinical Investigation, United States (Sep. 1997).
Wu, S.J., et al., "Structure-Based Engineering of a Monoclonal Antibody for Improved Solubility," Protein Engineering 23(8):643-651, Oxford University, England (Aug. 2010).
Wu, H., et al., "Detory Syncytial Virus Infection in the Upper and Lower Respiratory Tractvelopment of Motavizumab, an Ultra-potent Antibody for the Prevention of Respira," Journal of Molecular biology 368(3):652-665, Academic Press, England (May 2007).
Wypych, J., et al., "Human IgG2 Antibodies Display Disulfide-mediated Structural Isoforms," The Journal of Biological Chemistry 283(23):16194-16205, American Society for Biochemistry and Molecular Biology, United States (Jun. 2008).
Yamane-Ohnuki, N., et al., "Establishment of FUT8 Knockout Chinese Hamster Ovary Cells: an Ideal Host Cell Line for Producing Completely Defucosylated Antibodies With Enhanced Antibody-dependent Cellular Cytotoxicity," Biotechnology and bioengineering 87(5):614-622, Wiley, United States (Sep. 2004).
Yarilin, A., "Osnovy Immunologii," M.: Meditsina, 1999: pp. 169-172, 354-358/Fundamentals of Immunology. M: Medicina, 1999: pp. 169-172, 354-358.
Yarilin, A., "Osnovy Immunologii," M.: Meditsina, 1999: pp. 172-174/Fundamentals of Immunology. M: Medicina, 1999: pp. 172-174.
Yeung, Y.A., et al., "Engineering Human IgG1 Affinity to Human Neonatal Fc Receptor: Impact of Affinity Improvement on Pharmacokinetics in Primates," Journal of Immunology 182(12):7663-7671, American Association of Immunologists, United States (Jun. 2009).
Zalevsky, J., et al., "Enhanced Antibody Half-life Improves in Vivo Activity," Nature Biotechnology 28(2):157-159, Nature America Publishing, United States (Feb. 2010).

(56) References Cited

OTHER PUBLICATIONS

Zheng, Y., et al., "Translational Pharmcokinetics and Pharmacodynamics of an FcRn-Variant Anti-CD4 Monoclonal Antibody From Preclinical Model to Phase I Study," Clin Pharmacol Therapeut., 89(2):283-290 (2011).
Zoller, M.J. and Smith M., "Oligonucleotide-directed mutagenesis of DNA fragments cloned into M13 vectors," Methods in enzymology 100:468-500, Academic Press, United States (1983), Abstract.
Zust, R., et al., "Type I Interferon Signals in Macrophages and Dendritic Cells Control Dengue Virus Infection: Implications for a New Mouse Model to Test Dengue Vaccines," Journal of Virology 88(13):7276-7285, American Society For Microbiology, United States ( Jul. 2014).
Capel, P. J. A., et al., "Heterogeneity of Human IgG Fc Receptors," Immunomethods, 4:25-34 (1994).
Dubowchik, G. M., et al., "Doxorubicin Immunoconjugates Containing Bivalent Lysosomally-Cleavable Dipeptide Linkages," Bioorganic & Medicinal Chemistry Letters, 12:1529-1532 (2002).
Guyer, R. L., et al., "Immunoglobulin Binding by Mouse Intestinal Epithelial Cell Receptors," J Immunol., 117(2):587-593 (1976).
Jeffrey, S. C., et al. "Dipeptide-based highly potent doxorubicin antibody conjugates," Bioorganic & Medicinal Chemistry Letters, 16:358-362 (2006).
Kramer, W. and Fritz, H.-J., "Oligonucleotide-Directed Construction of Mutations via Gapped Duplex DNA," Methods in Enzymology, 154:350-367 (1987).
Lee, C. V., et al., "Bivalent antibody phage display mimics natural immunoglobulin," J Immunol Meth., 284:119-132 (2004).
Osbourn, J., et al., "From rodent reagents to human therapeutics using antibody guided selection," Methods, 36:61-68 (2005).
Ripka, J., et al., "Two Chinese Hamster Ovary Glycosylation Mutants Affected in the Conversion of GDP-Mannose to GDP-Fucose," Archives Biochem Biophys., 249(2):533-545 (1986).
Van Dijk, M. A. and Van De Winkel, J. G. J., "Human antibodies as next generation therapeutics," Curr Opin Chem Biol., 5:368-374 (2001).
Clarkson, T., et al., "Making antibody fragments using phage display libraries," Nature, 352:624-628 (1991).
Arduin, E., et al., "Highly reduced binding to high and low affinity mouse Fc gamma receptors by L234A/L235A and N297A Fc mutations engineered into mouse IgG2a," Mol Immunol., 63:456-463 (2015).
Datta-Mannan, A., et al., "FcRn Affinity-Pharmacokinetic Relationship of Five Human IgG4 Antibodies Engineered For Improved In Vitro FcRn Binding Properties In Cynomolgus Monkeys," Drug Metab Dispos., 40(8):1545-1555 (2012).
De Alwis, R., et al., "Identification of human neutralizing antibodies that bind to complex epitopes on dengue virions," PNAS, 109(19):7439-7444 (2012).
Derer, S., et al., "A Complement-Optimized EGFR Antibody Improves Cytotoxic Functions of Polymorphonuclear Cells against Tumor Cells," J Immunol., 195:5077-5087 (2015).
Idusogie, E. E., et al., "Engineered Antibodies with Increased Activity to Recruit Complement," J Immunol., 166:2571-2575 (2001).
International Search Report mailed Jan. 24, 2018 in International Patent Application No. PCT/SG2017/050465.
Moore, G. L., et al., "Engineered Fc variant antibodies with enhanced ability to recruit complement and mediate effector functions," mAbs 2(2):181-189 (2010).
Xu, M., et al., "Plasmablasts Generated during Repeated Dengue Infection Are Virus Glycoprotein-Specific and Bind to Multiple Virus Serotypes," J Immunol., 189:5877-5885 (2012).
U.S. Appl. No. 07/364,056, filed Jun. 9, 1989, McDonough et al.
U.S. Appl. No. 08/357,080, filed Dec. 15, 1994, Kishimoto.
U.S. Appl. No. 08/765,783, filed Mar. 7, 1997, Matsushima et al.
U.S. Appl. No. 08/921,100, filed Aug. 29, 1997, Matsushima et al.
U.S. Appl. No. 09/416,557, filed Oct. 12, 1999, Matsushima et al.
U.S. Appl. No. 09/646,188, filed Sep. 14, 2000, Ito et al.
U.S. Appl. No. 09/756,125, filed Jan. 9, 2001, Kishimoto et al.
U.S. Appl. No. 10/141,766, filed May 10, 2002, Mihara et al.
U.S. Appl. No. 10/474,832, filed Oct. 14, 2003, Lyne et al.
U.S. Appl. No. 10/677,227, filed Oct. 3, 2003, Ito et al.
U.S. Appl. No. 10/687,118, filed Oct. 15, 2003, Hinton et al.
U.S. Appl. No. 10/738,120, filed Dec. 16, 2003, Teeling et al.
U.S. Appl. No. 10/835,642, filed Apr. 30, 2004, Presta.
U.S. Appl. No. 10/837,904, filed May 4, 2004, Tsuchiya et al.
U.S. Appl. No. 11/004,054, filed Dec. 3, 2004, Lazar et al.
U.S. Appl. No. 11/089,426, filed Mar. 24, 2005, Gillies et al.
U.S. Appl. No. 11/255,528, filed Oct. 21, 2005, Dillon et al.
U.S. Appl. No. 11/271,140, filed Nov. 10, 2005, Stavenhagen.
U.S. Appl. No. 11/332,619, filed Jan. 12, 2006, Moore et al.
U.S. Appl. No. 11/397,328, filed Apr. 3, 2006, Dall'acqua et al.
U.S. Appl. No. 11/429,793, filed May 8, 2006, Presta.
U.S. Appl. No. 11/502,820, filed Aug. 10, 2006, Stavenhagen et al.
U.S. Appl. No. 11/514,217, filed Sep. 1, 2006, Yoshizaki et al.
U.S. Appl. No. 11/541,449, filed Sep. 29, 2006, Smith et al.
U.S. Appl. No. 11/653,206, filed Jan. 12, 2007, Pons et al.
U.S. Appl. No. 11/911,940, filed Apr. 16, 2008, Babcook et al.
U.S. Appl. No. 12/033,642, filed Feb. 19, 2008, Presta.
U.S. Appl. No. 12/294,171, filed Sep. 23, 2008, Kai et al.
U.S. Appl. No. 12/295,039, filed Jan. 20, 2009, Igawa et al.
U.S. Appl. No. 12/296,193, filed Apr. 15, 2009, Nishimoto et al.
U.S. Appl. No. 12/559,411, filed Sep. 14, 2009, Hariharan et al.
U.S. Appl. No. 12/559,415, filed Sep. 14, 2009, Hariharan et al.
U.S. Appl. No. 12/680,082, filed Jun. 25, 2010, Igawa et al., related application.
U.S. Appl. No. 12/680,112, filed Jun. 23, 2010, Igawa et al.
U.S. Appl. No. 13/192,429, filed Jul. 27, 2011, Dall'acqua et al.
U.S. Appl. No. 13/194,904, filed Jul. 29, 2011, Dahiyat et al.
U.S. Appl. No. 13/257,112, filed Nov. 22, 2011, Igawa et al., related application.
U.S. Appl. No. 13/257,145, filed Nov. 22, 2011, Igawa et al., related application.
U.S. Appl. No. 13/497,269, filed Jun. 1, 2012, Kuramochi et al.
U.S. Appl. No. 13/582,073, filed Dec. 20, 2012, Kuramochi et al.
U.S. Appl. No. 14/155,344, filed Jan. 14, 2014, Desjarlais et al.
U.S. Appl. No. 14/165,487, filed Jan. 27, 2014, Lazar et al.
U.S. Appl. No. 14/216,705, filed Mar. 17, 2014, Moore et al.
U.S. Appl. No. 14/680,250, filed Apr. 7, 2015, Igawa et al., related application.
U.S. Appl. No. 14/962,293, filed Dec. 8, 2015, Igawa et al., related application.
U.S. Appl. No. 15/015,287, filed Feb. 4, 2016, Igawa et al., related application.
U.S. Appl. No. 15/393,380, filed Dec. 29, 2016, Svensson et al.
U.S. Appl. No. 15/614,842, filed Jun. 6, 2017, Igawa et al., related application.
U.S. Appl. No. 15/976,288, filed May 10, 2018, Igawa et al., related application.
U.S. Appl. No. 16/298,032, filed Mar. 11, 2019, Igawa et al., related application.
U.S. Appl. No. 16/323,142, filed Feb. 4, 2019, Kakiuchi et al., related application.
Aikawa, E., Immunohistochemistry, Comprehensive Materials, Editor: Paul Ducheyne, Affinity section of chapter 3.316, p. 278 (2011).
Bournazos, S., et al., "The role of IgG Fc receptors in antibody-dependent enhancement," Nat Rev Immunol., 20:633-643 (2020).
Korean Office Action in Korean Application No. 10-2021-7028717 dated Nov. 29, 2021.
Lee, C.-H., et al., "IgG Fc domains that bind C1q but not effector Fcγ receptors delineate the importance of complement-mediated effector functions," Nat Immunol., 18(8):889-898 (2017).
Park, H. I., et al., "The Highly Evolvable Antibody Fc Domain," Trends in Biotechnology, 34(11):895-908 (2016).
Stettler, K., et al., "Specificity cross-reactivity, and function of antibodies elicited by Zika virus infection," Science, 353(6301):823-826 (2016).
U.S. Appl. No. 17/530,542, filed Nov. 19, 2021, Igawa et al., related application.
U.S. Appl. No. 17/720,937, filed Apr. 14, 2022, Igawa et al., related application.

(56) References Cited

OTHER PUBLICATIONS

Barba-Spaeth, G., et al., "Structural Basis of Potent Zika-dengue Virus Antibody Cross-neutralization," Nature, 4:536(7614):48-53 (2016).

Dejnirattisai, W., et al., "Dengue Virus Sero-cross-reactivity Drives Antibody-dependent Enhancement of Infection With Zika Virus," Nature Immunology, 17(9):1102-1108 (2016).

Devanaboyina, S., et al., "The Effect of Ph Dependence of Antibody-Antigen Interactions on Subcellular Trafficking Dynamics," MAbs, 5(6):851-859 (2013).

Di Stefano, A., et al., "Role of Interleukin-8 in the Pathogenesis and Treatment of COPD," Chest, 126(3):676-678 (2004).

Dondelinger, M., et al., "Understanding the Significance and Implications of Antibody Numbering and Antigen-binding Surface/residue Definition," Frontiers in Immunology, 16(9):2278 (2018).

Fernandez, E., et al., "Human Antibodies to the Dengue Virus E-dimer Epitope Have Therapeutic Activity Against Zika Virus Infection," Nature Immunology, 18(11):1261-1269 (2017).

Hezareh, M. et al., "Effector function activities of a panel of mutants of a broadly neutralizing antibody against human immunodeficiency virus type 1," J Virol. 75(24):12161-8 (2001).

Igawa, T., et al., "pH-dependent Antigen-binding Antibodies as a Novel Therapeutic Modality," Biochimica Et Biophysica Acta, 1844(11):1943-1950 (2014).

Kam, Y.W., et al., "Cross-Reactive Dengue Human Monoclonal Antibody Prevents Severe Pathologies and Death From Zika Virus Infections," JCI Insight, 2(8):e92428 (2017).

Marchalonis, J., et al., "Antigenic Mapping of a Human Lambda Light Chain: Correlation With Three Dimensional Structure," Journal of Protein Chemistry, 11(2):129-137 (1992).

Priyamvada, L., et al., "Human Antibody Responses After Dengue Virus Infection are Highly Cross-Reactive to Zika Virus," PNAS, 113(28):7852-7857 (2016).

Raghavan, M., et al., "Analysis of the pH Dependence of the Neonatal Fc Receptor/Immunoglobulin G Interaction Using Antibody and Receptor Variants," Biochemistry, 34(45):14649-14657 (1995).

Stavenhagen, J. B., et al., "Enhancing the Potency of Therapeutic Monoclonal Antibodies via Fc Optimization," Advances in Enzyme Regulation, 48:152-164 (2008).

Stryer, L., Biochemistry $4^{th}$ Edition, WH Freeman and Company, pp. 18-23, New York (1995).

U.S. Appl. No. 16/333,736, filed Mar. 15, 2019, Sampei et al., related application.

U.S. Appl. No. 16/435,979, filed Jun. 10, 2019, Sampei et al., related application.

U.S. Appl. No. 16/697,310, filed Nov. 27, 2019, Igawa et al., related application.

U.S. Appl. No. 16/980,611, filed Sep. 14, 2020, Fink et al., related application.

U.S. Appl. No. 17/333,256, filed May 28, 2021, Kakiuchi et al., related application.

U.S. Appl. No. 17/494, 199, filed Oct. 5, 2021, Igawa et al., related application.

Vaccaro, C., et al., "Engineering the Fc Region of Immunoglobulin G to Modulate in Vivo Antibody Levels," Nature Biotechnology, 23(10):1283-1288 (2005).

Wang, W., et al., "Monoclonal Antibodies With Identical Fc Sequences Can Bind to FcRn Differentially With Pharmacokinetic Consequences," Drug Metabolism and Disposition, 39(9):1469-1477 (2011).

Xu, M., et al., "A Potent Neutralizing Antibody With Therapeutic Potential Against All Four Serotypes of Dengue Virus," NPJ Vaccines, 2:2 (2017).

SEQUENCE LISTING

```
Sequence total quantity: 109
SEQ ID NO: 1           moltype = AA  length = 132
FEATURE                Location/Qualifiers
source                 1..132
                       mol_type = protein
                       organism = Homo sapiens
SEQUENCE: 1
QVQLVQSGPD VEKPGASVKV SCKASGYTFT SNYIHWVRQA PGQGLEWMGV INPRGGSTAS   60
AQKFQGRITM TRDTSTSTVY MELSSLRSDD TAVYYCARGG RALFYDSYTT PRDGGSWWFD  120
```

```
PWGQGSLVTV SS                                                                        132

SEQ ID NO: 2                moltype = AA  length = 132
FEATURE                     Location/Qualifiers
REGION                      1..132
                            note = VH
source                      1..132
                            mol_type = protein
                            organism = synthetic construct
SEQUENCE: 2
QVQLVQSGPD VEKPGASVKV SCKASGYTFT SNYIHWVRQA PGQGLEWMGV INPRGGSRAS     60
AQKFQGRITM TRDTSTSTVY MELSSLRSED TAVYYCARGG RALFYDSYTT PFDGGSWWFD    120
PWGQGSLVTV SS                                                       132

SEQ ID NO: 3                moltype = AA  length = 132
FEATURE                     Location/Qualifiers
REGION                      1..132
                            note = VH
source                      1..132
                            mol_type = protein
                            organism = synthetic construct
SEQUENCE: 3
QVQLVQSGPD VEKPGASVKV SCKASGYTFT SNYIHWVRQA PGQGLEWMGV INPRGGSRRS     60
AQKFQGRITM TRDTSTSTVY MELSSLRSED TAVYYCARGG RALFYDSYTT PFDGGSWWFD    120
PWGQGSLVTV SS                                                       132

SEQ ID NO: 4                moltype = AA  length = 132
FEATURE                     Location/Qualifiers
REGION                      1..132
                            note = VH
source                      1..132
                            mol_type = protein
                            organism = synthetic construct
SEQUENCE: 4
QVQLVQSGPD VEKPGASVKV SCKASGYTFT SNYIHWVRQA PGQGLEWMGV INPRGGSRRS     60
AQKFQGRITM TRDTSTSTVY MELSSLRSED TAVYYCARGG RALFYDSYTT PRDGGSWWFD    120
PWGQGSLVTV SS                                                       132

SEQ ID NO: 5                moltype = AA  length = 132
FEATURE                     Location/Qualifiers
REGION                      1..132
                            note = VH
source                      1..132
                            mol_type = protein
                            organism = synthetic construct
SEQUENCE: 5
QVQLVQSGPD VEKPGASVKV SCKASGYTFT SNYIHWVRQA PGQGLEWMGV INPRGGSRRS     60
AQKFQGRITM TRDTSTSTVY MELSSLRSED TAVYYCARGG RALFYDSYTT PRDLGSWWFD    120
PWGQGSLVTV SS                                                       132

SEQ ID NO: 6                moltype = AA  length = 132
FEATURE                     Location/Qualifiers
REGION                      1..132
                            note = VH
source                      1..132
                            mol_type = protein
                            organism = synthetic construct
SEQUENCE: 6
QVQLVQSGPD VEKPGASVKV SCKASGYTFT SYYMHWVRQA PGQGLEWMGV INPRGGSRRS     60
AQKFQGRITM TRDTSTSTVY MELSSLRSED TAVYYCARGG EALFYDSYTT PFDGGSWWFD    120
PWGQGSLVTV SS                                                       132

SEQ ID NO: 7                moltype = AA  length = 107
FEATURE                     Location/Qualifiers
source                      1..107
                            mol_type = protein
                            organism = Homo sapiens
SEQUENCE: 7
DIQLTQSPSS LSASVGDRVT FTCQASQDIR KYLNWYQQKP GKAPKLLIYD ASNLKTGVPS     60
RFSGSGSGTD FTFTISSLQP EDVATYYCQQ FDDLPITFGQ GTRLQIK                  107

SEQ ID NO: 8                moltype = AA  length = 107
FEATURE                     Location/Qualifiers
REGION                      1..107
                            note = VL
source                      1..107
                            mol_type = protein
                            organism = synthetic construct
SEQUENCE: 8
```

```
DIQLTQSPSS LSASVGDRVT FTCQASQDIR KYLNWYQQKP GKAPKLLIYD ASNLKFGVPS    60
RFSGSGSGTD FTFTISSLQP EDVATYYCQQ FDALPITFGQ GTRLQIK                 107

SEQ ID NO: 9            moltype = AA  length = 107
FEATURE                 Location/Qualifiers
REGION                  1..107
                        note = VL
source                  1..107
                        mol_type = protein
                        organism = synthetic construct
SEQUENCE: 9
DIQLTQSPSS LSASVGDRVT FTCQASQDIR QYLNWYQQKP GKAPKLLIYD ASNLKFGVPS    60
RFSGSGSGTD FTFTISSLQP EDVATYYCQQ FSALPITFGQ GTRLQIK                 107

SEQ ID NO: 10           moltype = AA  length = 107
FEATURE                 Location/Qualifiers
REGION                  1..107
                        note = VL
source                  1..107
                        mol_type = protein
                        organism = synthetic construct
SEQUENCE: 10
DIQLTQSPSS LSASVGDRVT FTCQASQEIR KYLNWYQQKP GKAPKLLIYD ASELKTGVPS    60
RFSGSGSGTD FTFTISSLQP EDVATYYCQQ FEDLPITFGQ GTRLQIK                 107

SEQ ID NO: 11           moltype = AA  length = 5
FEATURE                 Location/Qualifiers
source                  1..5
                        mol_type = protein
                        organism = Homo sapiens
SEQUENCE: 11
SNYIH                                                                 5

SEQ ID NO: 12           moltype = AA  length = 5
FEATURE                 Location/Qualifiers
REGION                  1..5
                        note = HVR-H1
source                  1..5
                        mol_type = protein
                        organism = synthetic construct
SEQUENCE: 12
SYYMH                                                                 5

SEQ ID NO: 13           moltype = AA  length = 17
FEATURE                 Location/Qualifiers
source                  1..17
                        mol_type = protein
                        organism = Homo sapiens
SEQUENCE: 13
VINPRGGSTA SAQKFQG                                                   17

SEQ ID NO: 14           moltype = AA  length = 17
FEATURE                 Location/Qualifiers
REGION                  1..17
                        note = HVR-H2
source                  1..17
                        mol_type = protein
                        organism = synthetic construct
SEQUENCE: 14
VINPRGGSRA SAQKFQG                                                   17

SEQ ID NO: 15           moltype = AA  length = 17
FEATURE                 Location/Qualifiers
REGION                  1..17
                        note = HVR-H2
source                  1..17
                        mol_type = protein
                        organism = synthetic construct
SEQUENCE: 15
VINPRGGSRR SAQKFQG                                                   17

SEQ ID NO: 16           moltype = AA  length = 23
FEATURE                 Location/Qualifiers
source                  1..23
                        mol_type = protein
                        organism = Homo sapiens
SEQUENCE: 16
GGRALFYDSY TTPRDGGSWW FDP                                            23
```

```
SEQ ID NO: 17              moltype = AA   length = 23
FEATURE                    Location/Qualifiers
REGION                     1..23
                           note = HVR-H3
source                     1..23
                           mol_type = protein
                           organism = synthetic construct
SEQUENCE: 17
GGRALFYDSY TTPFDGGSWW FDP                                              23

SEQ ID NO: 18              moltype = AA   length = 23
FEATURE                    Location/Qualifiers
REGION                     1..23
                           note = HVR-H3
source                     1..23
                           mol_type = protein
                           organism = synthetic construct
SEQUENCE: 18
GGRALFYDSY TTPRDDGSWW FDP                                              23

SEQ ID NO: 19              moltype = AA   length = 23
FEATURE                    Location/Qualifiers
REGION                     1..23
                           note = HVR-H3
source                     1..23
                           mol_type = protein
                           organism = synthetic construct
SEQUENCE: 19
GGRALFYDSY TTPRDLGSWW FDP                                              23

SEQ ID NO: 20              moltype = AA   length = 23
FEATURE                    Location/Qualifiers
REGION                     1..23
                           note = HVR-H3
source                     1..23
                           mol_type = protein
                           organism = synthetic construct
SEQUENCE: 20
GGEALFYDSY TTPFDGGSWW FDP                                              23

SEQ ID NO: 21              moltype = AA   length = 11
FEATURE                    Location/Qualifiers
source                     1..11
                           mol_type = protein
                           organism = Homo sapiens
SEQUENCE: 21
QASQDIRKYL N                                                           11

SEQ ID NO: 22              moltype = AA   length = 11
FEATURE                    Location/Qualifiers
REGION                     1..11
                           note = HVR-L1
source                     1..11
                           mol_type = protein
                           organism = synthetic construct
SEQUENCE: 22
QASQDIRQYL N                                                           11

SEQ ID NO: 23              moltype = AA   length = 11
FEATURE                    Location/Qualifiers
REGION                     1..11
                           note = HVR-L1
source                     1..11
                           mol_type = protein
                           organism = synthetic construct
SEQUENCE: 23
QASQEIRKYL N                                                           11

SEQ ID NO: 24              moltype = AA   length = 7
FEATURE                    Location/Qualifiers
source                     1..7
                           mol_type = protein
                           organism = Homo sapiens
SEQUENCE: 24
DASNLKT                                                                7

SEQ ID NO: 25              moltype = AA   length = 7
FEATURE                    Location/Qualifiers
REGION                     1..7
```

-continued

```
                        note = HVR-L2
source                  1..7
                        mol_type = protein
                        organism = synthetic construct
SEQUENCE: 25
DASNLKF                                                                  7

SEQ ID NO: 26           moltype = AA  length = 7
FEATURE                 Location/Qualifiers
REGION                  1..7
                        note = HVR-L2
source                  1..7
                        mol_type = protein
                        organism = synthetic construct
SEQUENCE: 26
DASELKT                                                                  7

SEQ ID NO: 27           moltype = AA  length = 9
FEATURE                 Location/Qualifiers
source                  1..9
                        mol_type = protein
                        organism = Homo sapiens
SEQUENCE: 27
QQFDDLPIT                                                                9

SEQ ID NO: 28           moltype = AA  length = 9
FEATURE                 Location/Qualifiers
REGION                  1..9
                        note = HVR-L3
source                  1..9
                        mol_type = protein
                        organism = synthetic construct
SEQUENCE: 28
QQFDALPIT                                                                9

SEQ ID NO: 29           moltype = AA  length = 9
FEATURE                 Location/Qualifiers
REGION                  1..9
                        note = HVR-L3
source                  1..9
                        mol_type = protein
                        organism = synthetic construct
SEQUENCE: 29
QQFSALPIT                                                                9

SEQ ID NO: 30           moltype = AA  length = 9
FEATURE                 Location/Qualifiers
REGION                  1..9
                        note = HVR-L3
source                  1..9
                        mol_type = protein
                        organism = synthetic construct
SEQUENCE: 30
QQFEDLPIT                                                                9

SEQ ID NO: 31           moltype = AA  length = 30
FEATURE                 Location/Qualifiers
source                  1..30
                        mol_type = protein
                        organism = Homo sapiens
SEQUENCE: 31
QVQLVQSGPD VEKPGASVKV SCKASGYTFT                                        30

SEQ ID NO: 32           moltype = AA  length = 14
FEATURE                 Location/Qualifiers
source                  1..14
                        mol_type = protein
                        organism = Homo sapiens
SEQUENCE: 32
WVRQAPGQGL EWMG                                                         14

SEQ ID NO: 33           moltype = AA  length = 32
FEATURE                 Location/Qualifiers
source                  1..32
                        mol_type = protein
                        organism = Homo sapiens
SEQUENCE: 33
RITMTRDTST STVYMELSSL RSDDTAVYYC AR                                     32
```

```
SEQ ID NO: 34            moltype = AA   length = 32
FEATURE                  Location/Qualifiers
REGION                   1..32
                         note = FR-H3
source                   1..32
                         mol_type = protein
                         organism = synthetic construct
SEQUENCE: 34
RITMTRDTST STVYMELSSL RSEDTAVYYC AR                                      32

SEQ ID NO: 35            moltype = AA   length = 11
FEATURE                  Location/Qualifiers
source                   1..11
                         mol_type = protein
                         organism = Homo sapiens
SEQUENCE: 35
WGQGSLVTVS S                                                             11

SEQ ID NO: 36            moltype = AA   length = 23
FEATURE                  Location/Qualifiers
source                   1..23
                         mol_type = protein
                         organism = Homo sapiens
SEQUENCE: 36
DIQLTQSPSS LSASVGDRVT FTC                                                23

SEQ ID NO: 37            moltype = AA   length = 15
FEATURE                  Location/Qualifiers
source                   1..15
                         mol_type = protein
                         organism = Homo sapiens
SEQUENCE: 37
WYQQKPGKAP KLLIY                                                         15

SEQ ID NO: 38            moltype = AA   length = 32
FEATURE                  Location/Qualifiers
source                   1..32
                         mol_type = protein
                         organism = Homo sapiens
SEQUENCE: 38
GVPSRFSGSG SGTDFTFTIS SLQPEDVATY YC                                      32

SEQ ID NO: 39            moltype = AA   length = 10
FEATURE                  Location/Qualifiers
source                   1..10
                         mol_type = protein
                         organism = Homo sapiens
SEQUENCE: 39
FGQGTRLQIK                                                               10

SEQ ID NO: 40            moltype =      length =
SEQUENCE: 40
000

SEQ ID NO: 41            moltype = AA   length = 17
FEATURE                  Location/Qualifiers
REGION                   1..17
                         note = HVR-H2
SITE                     9
                         note = MISC_FEATURE - Xaa is Thr or Arg
SITE                     10
                         note = MISC_FEATURE - Xaa is Ala or Arg
source                   1..17
                         mol_type = protein
                         organism = synthetic construct
SEQUENCE: 41
VINPRGGSXX SAQKFQG                                                       17

SEQ ID NO: 42            moltype = AA   length = 23
FEATURE                  Location/Qualifiers
REGION                   1..23
                         note = HVR-H3
SITE                     3
                         note = MISC_FEATURE - Xaa is Arg or Glu
SITE                     14
                         note = MISC_FEATURE - Xaa is Arg or Phe
SITE                     16
                         note = MISC_FEATURE - Xaa is Gly, Asp or Leu
source                   1..23
```

```
                              mol_type = protein
                              organism = synthetic construct
SEQUENCE: 42
GGXALFYDSY TTPXDXGSWW FDP                                          23

SEQ ID NO: 43             moltype = AA    length = 11
FEATURE                   Location/Qualifiers
REGION                    1..11
                          note = HVR-L1
SITE                      5
                          note = MISC_FEATURE - Xaa is Asp or Glu
SITE                      8
                          note = MISC_FEATURE - Xaa is Lys or Gln
source                    1..11
                          mol_type = protein
                          organism = synthetic construct
SEQUENCE: 43
QASQXIRXYL N                                                       11

SEQ ID NO: 44             moltype = AA    length = 7
FEATURE                   Location/Qualifiers
REGION                    1..7
                          note = HVR-L2
SITE                      4
                          note = MISC_FEATURE - Xaa is Asn or Glu
SITE                      7
                          note = MISC_FEATURE - Xaa is Thr or Phe
source                    1..7
                          mol_type = protein
                          organism = synthetic construct
SEQUENCE: 44
DASXLKX                                                            7

SEQ ID NO: 45             moltype = AA    length = 9
FEATURE                   Location/Qualifiers
REGION                    1..9
                          note = HVR-L3
SITE                      4
                          note = MISC_FEATURE - Xaa is Asp, Ser or Glu
SITE                      5
                          note = MISC_FEATURE - Xaa is Asp or Ala
source                    1..9
                          mol_type = protein
                          organism = synthetic construct
SEQUENCE: 45
QQFXXLPIT                                                          9

SEQ ID NO: 46             moltype = AA    length = 328
FEATURE                   Location/Qualifiers
REGION                    1..328
                          note = CH
source                    1..328
                          mol_type = protein
                          organism = synthetic construct
SEQUENCE: 46
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSP                                    328

SEQ ID NO: 47             moltype = AA    length = 328
FEATURE                   Location/Qualifiers
REGION                    1..328
                          note = CH
source                    1..328
                          mol_type = protein
                          organism = synthetic construct
SEQUENCE: 47
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSP                                    328

SEQ ID NO: 48             moltype = AA    length = 328
FEATURE                   Location/Qualifiers
```

```
REGION                  1..328
                        note = CH
source                  1..328
                        mol_type = protein
                        organism = synthetic construct
SEQUENCE: 48
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNWA LPAPISKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 49           moltype = AA  length = 328
FEATURE                 Location/Qualifiers
REGION                  1..328
                        note = CH
source                  1..328
                        mol_type = protein
                        organism = synthetic construct
SEQUENCE: 49
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLAG   120
PSVFLFPPKP KDTLMISRTP EVTCVVVDVE FEDPEVKFNW YVDGVEVHNA KTKPREEQYN   180
STYRVVSVLT VLHQDWLNGK EYKCKVTNKA LPAPEEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 50           moltype = AA  length = 328
FEATURE                 Location/Qualifiers
REGION                  1..328
                        note = CH
source                  1..328
                        mol_type = protein
                        organism = synthetic construct
SEQUENCE: 50
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVE FEDPEVKFNW YVDGVEVHNA KTKPREEQYN   180
STYRVVSVLT VLHQDWLNGK EYKCKVTNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 51           moltype = AA  length = 328
FEATURE                 Location/Qualifiers
REGION                  1..328
                        note = CH
source                  1..328
                        mol_type = protein
                        organism = synthetic construct
SEQUENCE: 51
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNWA LPAPISKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 52           moltype = AA  length = 328
FEATURE                 Location/Qualifiers
REGION                  1..328
                        note = CH
source                  1..328
                        mol_type = protein
                        organism = synthetic construct
SEQUENCE: 52
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEAAAG   120
PSVFLFPPKP KDTLMISRTP EVTCVVVDVE FEDPEVKFNW YVDGVEVHNA KTKPREEQYN   180
STYRVVSVLT VLHQDWLNGK EYKCKVTNKA LPAPEEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 53           moltype = AA  length = 328
FEATURE                 Location/Qualifiers
REGION                  1..328
                        note = CH
source                  1..328
                        mol_type = protein
```

```
                        organism = synthetic construct
SEQUENCE: 53
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEAAGG   120
PSVFLFPPKP KDTLMISRTP EVTCVVVDVE FEDPEVKFNW YVDGVEVHNA KTKPREEQYN   180
STYRVVSVLT VLHQDWLNGK EYKCKVTNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 54          moltype = AA  length = 328
FEATURE                Location/Qualifiers
REGION                 1..328
                       note = CH
source                 1..328
                       mol_type = protein
                       organism = synthetic construct
SEQUENCE: 54
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNAA LPAPISKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 55          moltype = AA  length = 328
FEATURE                Location/Qualifiers
REGION                 1..328
                       note = CH
source                 1..328
                       mol_type = protein
                       organism = synthetic construct
SEQUENCE: 55
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNDA LPAPISKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 56          moltype = AA  length = 328
FEATURE                Location/Qualifiers
REGION                 1..328
                       note = CH
source                 1..328
                       mol_type = protein
                       organism = synthetic construct
SEQUENCE: 56
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNEA LPAPISKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 57          moltype = AA  length = 328
FEATURE                Location/Qualifiers
REGION                 1..328
                       note = CH
source                 1..328
                       mol_type = protein
                       organism = synthetic construct
SEQUENCE: 57
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNMA LPAPISKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                     328

SEQ ID NO: 58          moltype = AA  length = 328
FEATURE                Location/Qualifiers
REGION                 1..328
                       note = CH
source                 1..328
                       mol_type = protein
                       organism = synthetic construct
SEQUENCE: 58
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEAAGG   120
```

```
PSVFLFPPKP KDTLMISRTP EVTCVVVDVS HEDPEVKFNW YVDGVEVHNA KTKPREEQYN    180
STYRVVSVLT VLHQDWLNGK EYKCKVSNAA LPAPISKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV LHEALHAHTT RKELSLSP                                      328

SEQ ID NO: 59           moltype = AA   length = 328
FEATURE                 Location/Qualifiers
REGION                  1..328
                        note = CH
source                  1..328
                        mol_type = protein
                        organism = synthetic construct
SEQUENCE: 59
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNAA LPAPISKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV LHEALHAHYT RKELSLSP                                      328

SEQ ID NO: 60           moltype = AA   length = 107
FEATURE                 Location/Qualifiers
REGION                  1..107
                        note = CL
source                  1..107
                        mol_type = protein
                        organism = synthetic construct
SEQUENCE: 60
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                 107

SEQ ID NO: 61           moltype = AA   length = 585
FEATURE                 Location/Qualifiers
REGION                  1..585
                        note = DENV
source                  1..585
                        mol_type = protein
                        organism = synthetic construct
SEQUENCE: 61
MKCLLYLAFL FIGVNCFHLT TRGGEPHMIV SKQERGKSLL FKTSAGVNMC TLIAMDLGEL     60
CEDTMTYKCP RITEAEPDDV DCWCNATDTW VTYGTCSQTG EHRRDKRSVA LAPHVGLGLE    120
TRTETWMSSE GAWKQIQKVE TWALRHPGFT VIALFLAHAI GTSITQKGII FILLMLVTPS    180
MAMRCVGIGN RDFVEGLSGA TWVDVVLEHG SCVTTMAKNK PTLDIELLKT EVTNPAVLRK    240
LCIEAKISNT TTDSRCPTQG EATLVEEQDA NFVCRRTVVD RGWGNGCGLF GKGSLLTCAK    300
FKCVTKLEGK IVQYENLKYS VIVTVHTGDQ HQVGNETTEH GTIATITPQA PTSEIQLTDY    360
GTLTLDCSPR TGLDFNEMVL LTMKEKSWLV HKQWFLDLPL PWTSGASTSQ ETWNRQDLLV    420
TFKTAHAKKQ EVVVLGSQEG AMHTALTGAT EIQTSGTTTI FAGHLKCRLK MDKLTLKGMS    480
YVMCTGSFKL EKEVAETQHG TVLVQVKYEG TDAPCKIPFS TQDEKGVTQN GRLITANPIV    540
TDKEKPVNIE TEPPFGESYI IVGAGEKALK LSWFKKGHHH HHHHH                   585

SEQ ID NO: 62           moltype = AA   length = 585
FEATURE                 Location/Qualifiers
REGION                  1..585
                        note = DENV
source                  1..585
                        mol_type = protein
                        organism = synthetic construct
SEQUENCE: 62
MKCLLYLAFL FIGVNCFHLT TRNGEPHMIV SRQEKGKSLL FKTEDGVNMC TLMAMDLGEL     60
CEDTITYKCP FLRQNEPEDI DCWCNSTSTW VTYGTCTTTG EHRREKRSVA LVPHVGMGLE    120
TRTETWMSSE GAWKHAQRIE TWILRHPGFT IMAAILAYTI GTTHFQRALI FILLTAVAPS    180
MTMRCIGISN RDFVEGVSGG SWVDIVLEHG SCVTTMAKNK PTLDFELIKT EAKQPATLRK    240
YCIEAKLTNT TTDSRCPTQG EPSLNEEQDK RFVCKHSMVD RGWGNGCGLF GKGGIVTCAM    300
FTCKKNMKGK VVQPENLEYT IVITPHSGEE HAVGNDTGKH GKEIKITPQS SITEAELTGY    360
GTVTMECSPR TGLDFNEMVL LQMENKAWLV HRQWFLDLPL PWLPGADTQG SNWIQKETLV    420
TFKNPHAKKQ DVVVLGSQEG AMHTALTGAT EIQMSSGNLL FTGHLKCRLR MDKLQLKGMS    480
YSMCTGKFKV VKEIAETQHG TIVIRVQYEG DGSPCKIPFE IMDLEKRHVL GRLITVNPIV    540
TEKDSPVNIE AEPPFGDSYI IIGVEPGQLK LNWFKKGHHH HHHHH                   585

SEQ ID NO: 63           moltype = AA   length = 583
FEATURE                 Location/Qualifiers
REGION                  1..583
                        note = DENV
source                  1..583
                        mol_type = protein
                        organism = synthetic construct
SEQUENCE: 63
MKCLLYLAFL FIGVNCFHLT SRDGEPRMIV GKNERGKSLL FKTASGINMC TLIAMDLGEM     60
CDDTVTYKCP HITEVEPEDI DCWCNLTSTW VTYGTCNQAG EHRRDKRSVA LAPHVGMGLD    120
```

-continued

```
TRTQTWMSAE GAWRQVEKVE TWALRHPGFT ILALFLAHYI GTSLTQKVVI FILLMLVTPS 180
MTMRCVGVGN RDFVEGLSGA TWVDVVLEHG GCVTTMAKNK PTLDIELQKT EATQLATLRK 240
LCIEGKITNI TTDSRCPTQG EAILPEEQDQ NYVCKHTYVD RGWGNGCGLF GKGSLVTCAK 300
FQCLESIEGK VVQHENLKYT VIITVHTGDQ HQVGNETQGV TAEITSQAST AEEAILPEYGT 360
LGLECSPRTG LDFNEMILLT MKNKAWMVHR QWFFDLPLPW TSGATTKTPT WNRKELLVTF 420
KNAHAKKQEV VVLGSQEGAM HTALTGATEI QTSGGTSIFA GHLKCRLKMD KLKLKGMSYA 480
MCLNTFVLKK EVSETQHGTI LIKVEYKGED APCKIPFSTE DGQGKAHNGR LITANPVVTK 540
KEEPVNIEAE PPFGESNIVI GIGDKALKIN WYRKGHHHHH HHH 583

SEQ ID NO: 64         moltype = AA  length = 585
FEATURE               Location/Qualifiers
REGION                1..585
                      note = DENV
source                1..585
                      mol_type = protein
                      organism = synthetic construct
SEQUENCE: 64
MKCLLYLAFL FIGVNCFSLS TRDGEPLMIV AKHERGRPLL FKTTEGINKC TLIAMDLGEM 60
CEDTVTYKCP LLVNTEPEDI DCWCNLTSTW VMYGTCTQSG ERRREKRSVA LTPHSGMGLE 120
TRAETWMSSE GAWKHAQRVE SWILRNPGFA LLAGFMAYMI GQTGIQRTVF FVLMMLVAPS 180
YGMRCVGVGN RDFVEGVSGG AWVDVLEHG GCVTTMAQGK PTLDFELTKT TAKEVALLRT 240
YCIEASISNI TTATRCPTQG EPYLKEEQDQ QYICRRDVVD RGWGNGCGLF GKGGVVTCAK 300
FSCSGKITGN LVQIENLEYT VVVTVHNGDT HAVGNDTSNH GVTAMITPRS PSVEVKLPDY 360
GELTLDCEPR SGIDFNEMIL MKMKKKTWLV HKQWFLDLPL PWTAGADTSE VHWNYKERMV 420
TFKVPHAKRQ DVTVLGSQEG AMHSALAGAT EVDSGDGNHM FAGHLKCKVR MEKLRIKGMS 480
YTMCSGKFSI DKEMAETQHG TTVVKVKYEG AGAPCKVPIE IRDVNKEKVV GRIISSTPLA 540
ENTNSVTNIE LEPPFGDSYI VIGVGNSALT LHWFRKGHHH HHHH 585

SEQ ID NO: 65         moltype = AA  length = 403
FEATURE               Location/Qualifiers
REGION                1..403
                      note = DENV
source                1..403
                      mol_type = protein
                      organism = synthetic construct
SEQUENCE: 65
MRCVGIGNRD FVEGLSGATW VDVVLEHGSC VTTMAKNKPT LDIELLKTEV TNPAVLRKLC 60
IEAKISNTTT DSRCPTQGEA TLVEEQDANF VCRRTVVDRG WGNGCGLFGK GSLLTCAKFK 120
CVTKLEGKIV QYENLKYSVI TVHTGDHQHQ VGNETTEHGT IATITPQAPT SEIQLTDYGT 180
LTLDCSPRTG LDFNEMVLLT MKEKSWLVHK QWFLDLPLPW TSGASTSQET WNRQDLLVTF 240
KTAHAKKQEV VVLGSQEGAM HTALTGATEI QTSGTTTIFA GHLKCRLKMD KLTLKGMSYV 300
MCTGSFKLEK EVAAETQHGTV LVQVKYEGTD APCKIPFSTQ DEKGVTQNGR LITANPIVTD 360
KEKPVNIETE PPFGESYIIV GAGEKALKLS WFKKGHHHHH HHH 403

SEQ ID NO: 66         moltype = AA  length = 403
FEATURE               Location/Qualifiers
REGION                1..403
                      note = DENV
source                1..403
                      mol_type = protein
                      organism = synthetic construct
SEQUENCE: 66
MRCIGISNRD FVEGVSGGSW VDIVLEHGSC VTTMAKNKPT LDFELIKTEA KQPATLRKYC 60
IEAKLTNTTT DSRCPTQGEP SLNEEQDKRF VCKHSMVDRG WGNGCGLFGK GGIVTCAMFT 120
CKKNMKGKVV QPENLEYTIV ITPHSGEEHA VGNDTGKHGK EIKITPQSSI TEAELTGYGT 180
VTMECSPRTG LDFNEMVLLQ MENKAWLVHR QWFLDLPLPW LPGADTQGSN WIQKETLVTF 240
KNPHAKKQDV VVLGSQEGAM HTALTGATEI QMSSGNLLFT GHLKCRLKMD KLQLKGMSYS 300
MCTGKFKVVK EIAETQHGTI VIRVQYEGDG SPCKIPFEIM DLEKRHVLGR LITVNPIVTE 360
KDSPVNIEAE PPFGDSYIII GVEPGQLKLN WFKKGHHHHH HHH 403

SEQ ID NO: 67         moltype = AA  length = 401
FEATURE               Location/Qualifiers
REGION                1..401
                      note = DENV
source                1..401
                      mol_type = protein
                      organism = synthetic construct
SEQUENCE: 67
MRCVGVGNRD FVEGLSGATW VDVVLEHGGC VTTMAKNKPT LDIELQKTEA TQLATLRKLC 60
IEGKITNITT DSRCPTQGEA ILPEEQDQNY VCKHTYVDRG WGNGCGLFGK GSLVTCAKFQ 120
CLESIEGKVV QHENLKYTVI ITVHTGDQHQ VGNETQGVTA EITSQASTAE AILPEYGTLG 180
LECSPRTGLD FNEMILLTMK NKAWMVHRQW FFDLPLPWTS GATTKTPTWN RKELLVTFKN 240
AHAKKQEVVV LGSQEGAMHT ALTGATEIQT SGGTSIFAGH LKCRLKMDKL KLKGMSYAMC 300
LNTFVLKKEV SETQHGTILI KVEYKGEDAP CKIPFSTEDG QGKAHNGRLI TANPVVTKKE 360
EPVNIEAEPP FGESNIVIGI GDKALKINWY RKGHHHHHHH H 401

SEQ ID NO: 68         moltype = AA  length = 403
FEATURE               Location/Qualifiers
REGION                1..403
```

```
                      note = DENV
source                1..403
                      mol_type = protein
                      organism = synthetic construct
SEQUENCE: 68
MRCVGVGNRD FVEGVSGGAW VDLVLEHGGC VTTMAQGKPT LDFELTKTTA KEVALLRTYC  60
IEASISNITT ATRCPTQGEP YLKEEQDQQY ICRRDVVDRG WGNGCGLFGK GGVVTCAKFS  120
CSGKITGNLV QIENLEYTVV VTVHNGDTHA VGNDTSNHGV TAMITPRSPS VEVKLPDYGE  180
LTLDCEPRSG IDFNEMILMK MKKKTWLVHK QWFLDLPLPW TAGADTSEVH WNYKERMVTF  240
KVPHAKRQDV TVLGSQEGAM HSALAGATEV DSGDGNHMFA GHLKCKVRME KLRIKGMSYT  300
MCSGKFSIDK EMAETQHGTT VVKVKYEGAG APCKVPIEIR DVNKEKVVGR IISSTPLAEN  360
TNSVTNIELE PPFGDSYIVI GVGNSALTLH WFRKGHHHHH HHH                    403

SEQ ID NO: 69         moltype = AA  length = 374
FEATURE               Location/Qualifiers
source                1..374
                      mol_type = protein
                      organism = Homo sapiens
SEQUENCE: 69
MWFLTTLLLW VPVDGQVDTT KAVITLQPPW VSVFQEETVT LHCEVLHLPG SSSTQWFLNG  60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGLQLPTPVW FHVLFYLAVG  300
IMFLVNTVLW VTIRKELKRK KKWDLEISLD SGHEKKVISS LQEDRHLEEE LKCQEQKEEQ  360
LQEGVHRKEP QGAT                                                    374

SEQ ID NO: 70         moltype = AA  length = 316
FEATURE               Location/Qualifiers
source                1..316
                      mol_type = protein
                      organism = Homo sapiens
SEQUENCE: 70
MTMETQMSQN VCPRNLWLLQ PLTVLLLLAS ADSQAAPPKA VLKLEPPWIN VLQEDSVTLT  60
CQGARSPESD SIQWFHNGNL IPTHTQPSYR FKANNNDSGE YTCQTGQTSL SDPVHLTVLS  120
EWLVLQTPHL EFQEGETIML RCHSWKDKPL VKVTFFQNGK SQKFSHLDPT FSIPQANHSH  180
SGDYHCTGNI GYTLFSSKPV TITVQVPSMG SSSPMGVIVA VVIATAVAAI VAAVVALIYC  240
RKKRISANST DPVKAAQFEP PGRQMIAIRK RQLEETNNDY ETADGGYMTL NPRAPTDDDK  300
NIYLTLPPND HVNSNN                                                  316

SEQ ID NO: 71         moltype = AA  length = 316
FEATURE               Location/Qualifiers
source                1..316
                      mol_type = protein
                      organism = Homo sapiens
SEQUENCE: 71
MTMETQMSQN VCPRNLWLLQ PLTVLLLLAS ADSQAAPPKA VLKLEPPWIN VLQEDSVTLT  60
CQGARSPESD SIQWFHNGNL IPTHTQPSYR FKANNNDSGE YTCQTGQTSL SDPVHLTVLS  120
EWLVLQTPHL EFQEGETIML RCHSWKDKPL VKVTFFQNGK SQKFSRLDPT FSIPQANHSH  180
SGDYHCTGNI GYTLFSSKPV TITVQVPSMG SSSPMGVIVA VVIATAVAAI VAAVVALIYC  240
RKKRISANST DPVKAAQFEP PGRQMIAIRK RQLEETNNDY ETADGGYMTL NPRAPTDDDK  300
NIYLTLPPND HVNSNN                                                  316

SEQ ID NO: 72         moltype = AA  length = 291
FEATURE               Location/Qualifiers
source                1..291
                      mol_type = protein
                      organism = Homo sapiens
SEQUENCE: 72
MGILSFLPVL ATESDWADCK SPQPWGHMLL WTAVLFLAPV AGTPAAPPKA VLKLEPQWIN  60
VLQEDSVTLT CRGTHSPESD SIQWFHNGNL IPTHTQPSYR FKANNNDSGE YTCQTGQTSL  120
SDPVHLTVLS EWLVLQTPHL EFQEGETIVL RCHSWKDKPL VKVTFFQNGK SKKFSRSDPN  180
FSIPQANHSH SGDYHCTGNI GYTLYSSKPV TITVQAPSSS PMGIIVAVVT GIAVAAIVAA  240
VVALIYCRKK RISANPTNPD EADKVGAENT ITYSLLMHPD ALEEPDDQNR I           291

SEQ ID NO: 73         moltype = AA  length = 254
FEATURE               Location/Qualifiers
source                1..254
                      mol_type = protein
                      organism = Homo sapiens
SEQUENCE: 73
MWQLLLPTAL LLLVSAGMRT EDLPKAVVFL EPQWYRVLEK DSVTLKCQGA YSPEDNSTQW  60
FHNESLISSQ ASSYFIDAAT VDDSGEYRCQ TNLSTLSDPV QLEVHIGWLL LQAPRWVFKE  120
EDPIHLRCHS WKNTALHKVT YLQNGKGRKY FHHNSDFYIP KATLKDSGSY FCRGLFGSKN  180
VSSETVNITI TQGLSVSTIS SFFPPGYQVS FCLVMVLLFA VDTGLYFSVK TNIRSSTRDW  240
KDHKFKWRKD PQDK                                                    254

SEQ ID NO: 74         moltype = AA  length = 254
FEATURE               Location/Qualifiers
```

```
source                  1..254
                        mol_type = protein
                        organism = Homo sapiens
SEQUENCE: 74
MWQLLLPTAL LLLVSAGMRT EDLPKAVVFL EPQWYRVLEK DSVTLKCQGA YSPEDNSTQW    60
FHNESLISSQ ASSYFIDAAT VDDSGEYRCQ TNLSTLSDPV QLEVHIGWLL LQAPRWVFKE   120
EDPIHLRCHS WKNTALHKVT YLQNGKGRKY FHHNSDFYIP KATLKDSGSY FCRGLVGSKN   180
VSSETVNITI TQGLSVSTIS SFFPPGYQVS FCLVMVLLFA VDTGLYFSVK TNIRSSTRDW   240
KDHKFKWRKD PQDK                                                    254

SEQ ID NO: 75           moltype = AA  length = 233
FEATURE                 Location/Qualifiers
source                  1..233
                        mol_type = protein
                        organism = Homo sapiens
SEQUENCE: 75
MWQLLLPTAL LLLVSAGMRT EDLPKAVVFL EPQWYRVLEK DSVTLKCQGA YSPEDNSTQW    60
FHNENLISSQ ASSYFIDAAT VDDSGEYRCQ TNLSTLSDPV QLEVHVGWLL LQAPRWVFKE   120
EDPIHLRCHS WKNTALHKVT YLQNGKDRKY FHHNSDFHIP KATLKDSGSY FCRGLVGSKN   180
VSSETVNITI TQGLAVSTIS SFSPPGYQVS FCLVMVLLFA VDTGLYFSVK TNI          233

SEQ ID NO: 76           moltype = AA  length = 233
FEATURE                 Location/Qualifiers
source                  1..233
                        mol_type = protein
                        organism = Homo sapiens
SEQUENCE: 76
MWQLLLPTAL LLLVSAGMRT EDLPKAVVFL EPQWYSVLEK DSVTLKCQGA YSPEDNSTQW    60
FHNESLISSQ ASSYFIDAAT VNDSGEYRCQ TNLSTLSDPV QLEVHIGWLL LQAPRWVFKE   120
EDPIHLRCHS WKNTALHKVT YLQNGKDRKY FHHNSDFHIP KATLKDSGSY FCRGLVGSKN   180
VSSETVNITI TQGLAVSTIS SFSPPGYQVS FCLVMVLLFA VDTGLYFSVK TNI          233

SEQ ID NO: 77           moltype = AA  length = 404
FEATURE                 Location/Qualifiers
source                  1..404
                        mol_type = protein
                        organism = Mus musculus
SEQUENCE: 77
MILTSFGDDM WLLTTLLLWV PVGGEVVNAT KAVITLQPPW VSIFQKENVT LWCEGPHLPG    60
DSSTQWFING TAVQISTPSY SIPEASFQDS GEYRCQIGSS MPSDPVQLQI HNDWLLLQAS   120
RRVLTEGEPL ALRCHGWKNK LVYNVVFYRN GKSFQFSSDS EVAILKTNLS HSGIYHCSGT   180
GRHRYTSAGV SITVKELFTT PVLRASVSSP FPEGSLVTLN CETNLLLQRP GLQLHFSFYV   240
GSKILEYRNT SSEYHIARAE REDAGFYWCE VATEDSVSLK RSPELELQVL GPQSSAPVWF   300
HILFYLSVGI MFSLNTVLYV KIHRLQREKK YNLEVPLVSE QGKKANSFQQ VRSDGVYEEV   360
TATASQTTPK EAPDGPRSSV GDCGPEQPEP LPPSDSTGAQ TSQS                    404

SEQ ID NO: 78           moltype = AA  length = 293
FEATURE                 Location/Qualifiers
source                  1..293
                        mol_type = protein
                        organism = Mus musculus
SEQUENCE: 78
MGILPFLLIP MESNWTVHVF SRTLCHMLLW TAVLNLAAGT HDLPKAVVKL EPPWIQVLKE    60
DTVTLTCEGT HNPGNSSTQW FHNGRSIRSQ VQASYTFKAT VNDSGEYRCQ MEQTRLSDPV   120
DLGVISDWLL LQTPQLVFLE GETITLRCHS WRNKLLNRIS FPHNEKSVRY HHYSSNFSIP   180
KANHSHSGDY YCKGSLGRTL HQSKPVTITV QGPKSSRSLP VLTIVAAVTG IAVAAIVIIL   240
VSLVYLKKKQ VPDNPPDLEE AAKTEAENTI TYSLLKHPEA LDEETEHDYQ NHI          293

SEQ ID NO: 79           moltype = AA  length = 267
FEATURE                 Location/Qualifiers
source                  1..267
                        mol_type = protein
                        organism = Mus musculus
SEQUENCE: 79
MTLDTQMFQN AHSGSQWLLP PLTILLLFAF ADRQSAALPK AVVKLDPPWI QVLKEDMVTL    60
MCEGTHNPGN SSTQWFHNWS SIRSQVQSSY TFKATVNDSG EYRCQMEQTR LSDPVDLGVI   120
SDWLLLQTPQ RVFLEGETIT LRCHSWRNKL LNRISFFHNE KSVRYHHYKS NFSIPKANHS   180
HSGDYYCKGS LGSTQHQSKP VTITVQDPAT TSSISLVWYH TAFSLVMCLL FAVDTGLYFY   240
VRRNLQTPRD YWRKSLSIRK HQAPQDK                                      267

SEQ ID NO: 80           moltype = AA  length = 249
FEATURE                 Location/Qualifiers
source                  1..249
                        mol_type = protein
                        organism = Mus musculus
SEQUENCE: 80
MWQLLLPTAL VLTAFSGIQA GLQKAVVNLD PKWVRVLEED SVTLRCQGTF SPEDNSIKWF    60
HNESLIPHQD ANYVIQSARV KDSGMYRCQT ALSTISDPVQ LEVHMGWLLL QTTKWLFQEG   120
DPIHLRCHSW QNRPVRKVTY LQNGKGKKYF HENSELLIPK ATHNDSGSYF CRGLIGHNNK   180
```

```
SSASFRISLG DPGSPSMFPP WHQITFCLLI GLLFAIDTVL YFSVRRGLQS PVADYEEPKI    240
QWSKEPQDK                                                            249

SEQ ID NO: 81           moltype = AA  length = 365
FEATURE                 Location/Qualifiers
source                  1..365
                        mol_type = protein
                        organism = Homo sapiens
SEQUENCE: 81
MGVPRPQPWA LGLLLFLLPG SLGAESHLSL LYHLTAVSSP APGTPAFWVS GWLGPQQYLS    60
YNSLRGEAEP CGAWVWENQV SWYWEKETTD LRIKEKLFLE AFKALGGKGP YTLQGLLGCE    120
LGPDNTSVPT AKFALNGEEF MNFDLKQGTW GGDWPEALAI SQRWQQQDKA ANKELTFLLF    180
SCPHRLREHL ERGRGNLEWK EPPSMRLKAR PSSPGFSVLT CSAFSFYPPE LQLRFLRNGL    240
AAGTGQGDFG PNSDGSFHAS SSLTVKSGDE HHYCCIVQHA GLAQPLRVEL ESPAKSSVLV    300
VGIVIGVLLL TAAAVGGALL WRRMRSGLPA PWISLRGDDT GVLLPTPGEA QDADLKDVNV    360
IPATA                                                                365

SEQ ID NO: 82           moltype = AA  length = 119
FEATURE                 Location/Qualifiers
source                  1..119
                        mol_type = protein
                        organism = Homo sapiens
SEQUENCE: 82
MSRSVALAVL ALLSLSGLEA IQRTPKIQVY SRHPAENGKS NFLNCYVSGF HPSDIEVDLL    60
KNGERIEKVE HSDLSFSKDW SFYLLYYTEF TPTEKDEYAC RVNHVTLSQP KIVKWDRDM     119

SEQ ID NO: 83           moltype = AA  length = 330
FEATURE                 Location/Qualifiers
source                  1..330
                        mol_type = protein
                        organism = Homo sapiens
SEQUENCE: 83
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                     330

SEQ ID NO: 84           moltype = AA  length = 326
FEATURE                 Location/Qualifiers
source                  1..326
                        mol_type = protein
                        organism = Homo sapiens
SEQUENCE: 84
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKKVEP KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDIAVEW ESNGQPENNY KTTPPMLDSD GSFFLYSKLT VDKSRWQQGN    300
VFSCSVMHEA LHNHYTQKSL SLSPGK                                         326

SEQ ID NO: 85           moltype = AA  length = 377
FEATURE                 Location/Qualifiers
source                  1..377
                        mol_type = protein
                        organism = Homo sapiens
SEQUENCE: 85
ASTKGPSVFP LAPCSRSTSG GTAALGCLVK DYFPEPVTVS WNSGALTSGV HTFPAVLQSS    60
GLYSLSSVVT VPSSSLGTQT YTCNVNHKPS NTKVDKRVEL KTPLGDTTHT CPRCPEPKSC    120
DTPPPCPRCP EPKSCDTPPP CPRCPEPKSC DTPPPCPRCP APELLGGPSV FLFPPKPKDT    180
LMISRTPEVT CVVVDVSHED PEVQFKWYVD GVEVHNAKTK PREEQYNSTF RVVSVLTVLH    240
QDWLNGKEYK CKVSNKALPA PIEKTISKTK GQPREPQVYT LPPSREEMTK NQVSLTCLVK    300
GFYPSDIAVE WESSGQPENN YNTTPPMLDS DGSFFLYSKL TVDKSRWQQG NIFSCSVMHE    360
ALHNRFTQKS LSLSPGK                                                   377

SEQ ID NO: 86           moltype = AA  length = 327
FEATURE                 Location/Qualifiers
source                  1..327
                        mol_type = protein
                        organism = Homo sapiens
SEQUENCE: 86
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                        327
```

```
SEQ ID NO: 87            moltype = AA    length = 328
FEATURE                  Location/Qualifiers
REGION                   1..328
                         note = CH
source                   1..328
                         mol_type = protein
                         organism = synthetic construct
SEQUENCE: 87
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSP                                      328

SEQ ID NO: 88            moltype = AA    length = 119
FEATURE                  Location/Qualifiers
REGION                   1..119
                         note = VH
source                   1..119
                         mol_type = protein
                         organism = synthetic construct
SEQUENCE: 88
EVQLVESGGG SVKPGGSLKL SCAASGFTFS DHYMYWVRQT PEKRLEWVAI ISGGGSYTSY    60
PDSMKGRFTI SRDNAKNILH LQMSSLKSED TAMYYCTRES NGKPGFAYWG QGTLVTVSA    119

SEQ ID NO: 89            moltype = AA    length = 111
FEATURE                  Location/Qualifiers
REGION                   1..111
                         note = VL
source                   1..111
                         mol_type = protein
                         organism = synthetic construct
SEQUENCE: 89
DIELTQSPTS LAVSLGQRAT ISCKASQSVD YAGDSYMNWY QQKPGQPPKL LIYAASNLES    60
GIPARFSASG SGTDFTLNIH PVEEEDAATY YCQQSYEDPW TFGGGTKLEI K            111

SEQ ID NO: 90            moltype = AA    length = 132
FEATURE                  Location/Qualifiers
REGION                   1..132
                         note = VH
source                   1..132
                         mol_type = protein
                         organism = synthetic construct
SEQUENCE: 90
QVQLVQSGPD VEKPGASVKV SCKASGYTFT SYYIHWVRQA PGQGLEWMGV INPRGGSRRS    60
AQKFQGRITM TRDTSTSTVY MELSSLRSED TAVYYCARGG RALFYDSYTT PFDGGSWWFD   120
PWGQGSLVTV SS                                                       132

SEQ ID NO: 91            moltype = AA    length = 132
FEATURE                  Location/Qualifiers
REGION                   1..132
                         note = VH
source                   1..132
                         mol_type = protein
                         organism = synthetic construct
SEQUENCE: 91
QVQLVQSGAE VKKPGASVKV SCKASGYTFT SNYIHWVRQA PGQGLEWMGV INPRGGSRRS    60
AQKFQGRVTM TRDTSTSTVY MELSSLRSED TAVYYCARGG RALFYDSYTT PFDGGSWWFD   120
PWGQGSLVTV SS                                                       132

SEQ ID NO: 92            moltype = AA    length = 132
FEATURE                  Location/Qualifiers
REGION                   1..132
                         note = VH
source                   1..132
                         mol_type = protein
                         organism = synthetic construct
SEQUENCE: 92
QVQLVQSGAE VKKPGASVKV SCKASGYTFT SYYIHWVRQA PGQGLEWMGV INPRGGSRRS    60
AQKFQGRVTM TRDTSTSTVY MELSSLRSED TAVYYCARGG RALFYDSYTT PFDGGSWWFD   120
PWGQGSLVTV SS                                                       132

SEQ ID NO: 93            moltype = AA    length = 132
FEATURE                  Location/Qualifiers
REGION                   1..132
                         note = VH
source                   1..132
                         mol_type = protein
```

```
                        organism = synthetic construct
SEQUENCE: 93
QVQLVQSGPD VEKPGASVKV SCKASGYTFT SYYMHWVRQA PGQGLEWMGV INPRGGSRRS    60
AQKFQGRITM TRDTSTSTVY MELSSLRSED TAVYYCARGG RALFYDSYTT PFDGGSWWFD   120
PWGQGSLVTV SS                                                       132

SEQ ID NO: 94           moltype = AA  length = 132
FEATURE                 Location/Qualifiers
REGION                  1..132
                        note = VH
source                  1..132
                        mol_type = protein
                        organism = synthetic construct
SEQUENCE: 94
QVQLVQSGAE VKKPGASVKV SCKASGYTFT SYYMHWVRQA PGQGLEWMGV INPRGGSRRS    60
AQKFQGRVTM TRDTSTSTVY MELSSLRSED TAVYYCARGG RALFYDSYTT PFDGGSWWFD   120
PWGQGSLVTV SS                                                       132

SEQ ID NO: 95           moltype = AA  length = 132
FEATURE                 Location/Qualifiers
REGION                  1..132
                        note = VH
source                  1..132
                        mol_type = protein
                        organism = synthetic construct
SEQUENCE: 95
QVQLVQSGAE VKKPGASVKV SCKASGYTFT SYYMHWVRQA PGQGLEWMGV INPRGGSRRS    60
AQKFQGRVTM TRDTSTSTVY MELSSLRSED TAVYYCARGG EALFYDSYTT PFDGGSWWFD   120
PWGQGSLVTV SS                                                       132

SEQ ID NO: 96           moltype = AA  length = 107
FEATURE                 Location/Qualifiers
REGION                  1..107
                        note = VL
source                  1..107
                        mol_type = protein
                        organism = synthetic construct
SEQUENCE: 96
DIQLTQSPSS LSASVGDRVT FTCQASQDIR KYLNWYQQKP GKAPKLLIYD ASNLKTGVPS    60
RFSGSGSGTD FTFTISSLQP EDVATYYCQQ FEDLPITFGQ GTRLQIK                 107

SEQ ID NO: 97           moltype = AA  length = 107
FEATURE                 Location/Qualifiers
REGION                  1..107
                        note = VL
source                  1..107
                        mol_type = protein
                        organism = synthetic construct
SEQUENCE: 97
DIQLTQSPSS LSASVGDRVT FTCQASQEIR KYLNWYQQKP GKAPKLLIYD ASNLKTGVPS    60
RFSGSGSGTD FTFTISSLQP EDVATYYCQQ FDDLPITFGQ GTRLQIK                 107

SEQ ID NO: 98           moltype = AA  length = 107
FEATURE                 Location/Qualifiers
REGION                  1..107
                        note = VL
source                  1..107
                        mol_type = protein
                        organism = synthetic construct
SEQUENCE: 98
DIQLTQSPSS LSASVGDRVT ITCQASQDIR KYLNWYQQKP GKAPKLLIYD ASNLKTGVPS    60
RFSGSGSGTD FTLTISSLQP EDVATYYCQQ FDDLPITFGQ GTRLQIK                 107

SEQ ID NO: 99           moltype = AA  length = 107
FEATURE                 Location/Qualifiers
REGION                  1..107
                        note = VL
source                  1..107
                        mol_type = protein
                        organism = synthetic construct
SEQUENCE: 99
DIQLTQSPSS LSASVGDRVT ITCQASQEIR KYLNWYQQKP GKAPKLLIYD ASNLKTGVPS    60
RFSGSGSGTD FTLTISSLQP EDVATYYCQQ FDDLPITFGQ GTRLQIK                 107

SEQ ID NO: 100          moltype = AA  length = 107
FEATURE                 Location/Qualifiers
REGION                  1..107
                        note = VL
source                  1..107
```

```
                        mol_type = protein
                        organism = synthetic construct
SEQUENCE: 100
DIQLTQSPSS LSASVGDRVT ITCQASQDIR KYLNWYQQKP GKAPKLLIYD ASNLKTGVPS    60
RFSGSGSGTD FTLTISSLQP EDVATYYCQQ FEDLPITFGQ GTRLQIK                 107

SEQ ID NO: 101          moltype = AA   length = 5
FEATURE                 Location/Qualifiers
REGION                  1..5
                        note = HVR-H1
source                  1..5
                        mol_type = protein
                        organism = synthetic construct
SEQUENCE: 101
SYYIH                                                                 5

SEQ ID NO: 102          moltype = AA   length = 30
FEATURE                 Location/Qualifiers
REGION                  1..30
                        note = FR-H1
source                  1..30
                        mol_type = protein
                        organism = synthetic construct
SEQUENCE: 102
QVQLVQSGAE VKKPGASVKV SCKASGYTFT                                     30

SEQ ID NO: 103          moltype = AA   length = 32
FEATURE                 Location/Qualifiers
REGION                  1..32
                        note = FR-H3
source                  1..32
                        mol_type = protein
                        organism = synthetic construct
SEQUENCE: 103
RVTMTRDTST STVYMELSSL RSEDTAVYYC AR                                  32

SEQ ID NO: 104          moltype = AA   length = 23
FEATURE                 Location/Qualifiers
REGION                  1..23
                        note = FR-L1
source                  1..23
                        mol_type = protein
                        organism = synthetic construct
SEQUENCE: 104
DIQLTQSPSS LSASVGDRVT ITC                                            23

SEQ ID NO: 105          moltype = AA   length = 32
FEATURE                 Location/Qualifiers
REGION                  1..32
                        note = FR-L3
source                  1..32
                        mol_type = protein
                        organism = synthetic construct
SEQUENCE: 105
GVPSRFSGSG SGTDFTLTIS SLQPEDVATY YC                                  32

SEQ ID NO: 106          moltype = AA   length = 157
FEATURE                 Location/Qualifiers
REGION                  1..157
                        note = CD154
source                  1..157
                        mol_type = protein
                        organism = synthetic construct
SEQUENCE: 106
DYKDDDDKMQ KGDQNPQIAA HVISEASSKT TSVLQWAEKG YYTMSNNLVT LENGKQLTVK    60
RQGLYYIYAQ VTFCSNREAS SQAPFIASLC LKSPGRFERI LLRAANTHSS AKPCGQQSIH   120
LGGVFELQPG ASVFVNVTDP SQVSHGTGFT SFGLLKL                            157

SEQ ID NO: 107          moltype = AA   length = 328
FEATURE                 Location/Qualifiers
REGION                  1..328
                        note = CH
source                  1..328
                        mol_type = protein
                        organism = synthetic construct
SEQUENCE: 107
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
```

```
STYRVVSVLT VLHQDWLNGK EYKCKVSNAA LPAPISKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSP                                      328

SEQ ID NO: 108         moltype = AA   length = 328
FEATURE                Location/Qualifiers
REGION                 1..328
                       note = CH
source                 1..328
                       mol_type = protein
                       organism = synthetic construct
SEQUENCE: 108
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VLHQDWLNGK EYCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV LHEALHAHTT RKELSLSP                                      328

SEQ ID NO: 109         moltype = AA   length = 328
FEATURE                Location/Qualifiers
REGION                 1..328
                       note = CH
source                 1..328
                       mol_type = protein
                       organism = synthetic construct
SEQUENCE: 109
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VLHQDWLNGK EYCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV LHEALHAHYT RKELSLSP                                      328
```

ANTI-DENGUE VIRUS ANTIBODIES, POLYPEPTIDES CONTAINING VARIANT Fc REGIONS, AND METHODS OF USE

CROSS-REFERENCE TO RELATED APPLICATIONS

This application is a Continuation of U.S. application Ser. No. 17/066,092, filed Oct. 8, 2020, which is a Divisional of U.S. application Ser. No. 16/435,979, filed Jun. 10, 2019, now U.S. Pat. No. 10,844,113, issued Nov. 24, 2020, which is a Continuation of U.S. application Ser. No. 16/333,736, filed Mar. 15, 2019, now U.S. Pat. No. 10,604,561, issued Mar. 31, 2020, which is a U.S. National Phase of PCT Application No. PCT/SG2017/050465, filed Sep. 15, 2017, which claims the benefit of Singaporean Patent Application No. 10201607778X, filed Sep. 16, 2016, each of which is incorporated herein by reference in its entirety.

REFERENCE TO SEQUENCE LISTING SUBMITTED ELECTRONICALLY

The content of the electronically submitted sequence listing (Name: 6663_0260_Sequence_Listing.xml; Size: 140 kilobytes; and Date of Creation: Aug. 16, 2023) filed with the application is incorporated herein by reference in its entirety.

FIELD OF THE INVENTION

The present invention relates to anti-dengue virus antibodies and methods of using the same. The present invention also relates to polypeptides containing variant Fc regions and methods of using the same

BACKGROUND

Dengue fever is the most common arthropod-borne viral disease in the world. The virus causing dengue (or referred to herein as DENV) can be divided into four different infective serotypes such as DENV-1, DENV-2, DENV-3, and DENV-4. Symptoms of dengue infection include fever, muscle pain, headache, low platelet numbers and low white blood cell numbers, coagulopathy, bleeding and vascular leakage that can lead to dengue shock syndrome. When a person is exposed to the dengue virus after a previous dengue infection, antiviral antibodies may enhance the uptake of virus into host cells and the patient is at higher risk to develop a severe form or dengue. Severe forms of dengue can, however, also occur during a first infection.

Whilst being the most common arthropod-borne viral disease, to date, there is no drug available for treating dengue. Approaches with regards to dengue as a disease have mainly been towards the prevention of the infection and/or treatment to alleviate symptoms.

Thus, there is a need to provide agents capable of neutralizing and/or binding to at least one dengue serotype. Recently, several groups have reported on anti-DENV neutralizing antibodies (see, e.g., WO2012/082073, WO2013/089647, WO2013/151764, WO2013/173348, WO2014/025546, WO2015/123362, WO2015/122995, and WO2016/012800). However, antibodies with superior therapeutic properties are still needed.

Vaccines and antibody therapeutics are currently in development to prevent and treat virus infection. However, antibody based treatments are not without risks. One such risk is antibody-dependent enhancement (ADE), which occurs when non-neutralising antiviral antibodies facilitate virus entry into host cells, leading to increased infectivity in the cells (Expert Rev Anti Infect Ther (2013) 11, 1147-1157). The most common mechanism for ADE is the interaction of the virus-antibody complex through the Fc portion of the antibody with Fc receptors (FcRs) on the cell surface. A normally mild viral infection can be enhanced by ADE to become a life-threatening disease. It has been reported that an anti-DENV antibody with mutations in the Fc region that prevent binding to FcγR failed to enhance DENV infection (WO2010/043977). However, there is still a need for antibody therapeutics without increasing the risk of antibody-dependent enhancement of infection.

SUMMARY

The invention provides anti-DENV antibodies, polypeptides containing variant Fc regions, and methods of using the same.

In some embodiments, an isolated anti-DENV antibody of the present invention binds to DENV E protein. In some embodiments, an anti-DENV antibody of the invention comprises:
(a) (i) HVR-H3 comprising the amino acid sequence GGX$_1$ALFYDSYTTPX$_2$DX$_3$GSWWFDP, wherein X$_1$ is R or E, X$_2$ is R or F, X$_3$ is G, D or L (SEQ ID NO: 42), (ii) HVR-L3 comprising the amino acid sequence QQFX$_1$X$_2$LPIT, wherein X$_1$ is D, S or E, X$_2$ is D or A (SEQ ID NO: 45), and (iii) HVR-H2 comprising the amino acid sequence VINPRGGSX$_1$X$_2$SAQKFQG, wherein X$_1$ is T or R, X$_2$ is A or R (SEQ ID NO: 41);
(b) (i) HVR-H1 comprising the amino acid sequence SX$_1$YX$_2$H, wherein X$_1$ is N or Y, X$_2$ is I or M (SEQ ID NO: 40), (ii) HVR-H2 comprising the amino acid sequence VINPRGGSX$_1$X$_2$SAQKFQG, wherein X$_1$ is T or R, X$_2$ is A or R (SEQ ID NO: 41), and (iii) HVR-H3 comprising the amino acid sequence GGX$_1$ALFYDSYTTPX$_2$DX$_3$GSWWFDP, wherein X$_1$ is R or E, X$_2$ is R or F, X$_3$ is G, D or L (SEQ ID NO: 42);
(c) (i) HVR-H1 comprising the amino acid sequence SX$_1$YX$_2$H, wherein X$_1$ is N or Y, X$_2$ is I or M (SEQ ID NO: 40), (ii) HVR-H2 comprising the amino acid sequence VINPRGGSX$_1$X$_2$SAQKFQG, wherein X$_1$ is T or R, X$_2$ is A or R (SEQ ID NO: 41), (iii) HVR-H3 comprising the amino acid sequence GGX$_1$ALFYDSYTTPX$_2$DX$_3$GSWWFDP, wherein X$_1$ is R or E, X$_2$ is R or F, X$_3$ is G, D or L (SEQ ID NO: 42), (iv) HVR-L1 comprising the amino acid sequence QASQX$_1$IRX$_2$YLN, wherein X$_1$ is D or E, X$_2$ is K or Q (SEQ ID NO: 43); (v) HVR-L2 comprising the amino acid sequence DASX$_1$LKX$_2$, wherein X$_1$ is N or E, X$_2$ is T or F (SEQ ID NO: 44); and (vi) HVR-L3 comprising the amino acid sequence QQFX$_1$X$_2$LPIT, wherein X$_1$ is D, S or E, X$_2$ is D or A (SEQ ID NO: 45); or
(d) (i) HVR-L1 comprising the amino acid sequence QASQX$_1$IRX$_2$YLN, wherein X$_1$ is D or E, X$_2$ is K or Q (SEQ ID NO: 43); (ii) HVR-L2 comprising the amino acid sequence DASX$_1$LKX$_2$, wherein X$_1$ is N or E, X$_2$ is T or F (SEQ ID NO: 44); and (iii) HVR-L3 comprising the amino acid sequence QQFX$_1$X$_2$LPIT, wherein X$_1$ is D, S or E, X$_2$ is D or A (SEQ ID NO: 45).
In some embodiments, the antibody of the invention is not an antibody comprising (i) HVR-H1 comprising the amino acid sequence of SEQ ID NO: 11, (ii) HVR-H2 comprising the amino acid sequence of SEQ ID NO:

13, (iii) HVR-H3 comprising the amino acid sequence of SEQ ID NO: 16, (iv) HVR-L1 comprising the amino acid sequence of SEQ ID NO: 21, (v) HVR-L2 comprising the amino acid sequence of SEQ ID NO: 24, and (vi) HVR-L3 comprising the amino acid sequence of SEQ ID NO: 27.

In some embodiments, an isolated anti-DENV antibody of the invention comprises:

(a) (i) HVR-H3 from the VH sequence of any one of SEQ ID NOs: 2-6, (ii) HVR-L3 from the VL sequence of any one of SEQ ID NOs: 8-10, and (iii) HVR-H2 from the VH sequence of any one of SEQ ID NOs: 2-6;

(b) (i) HVR-H1 from the VH sequence of any one of SEQ ID NOs: 2-6, (ii) HVR-H2 from the VH sequence of any one of SEQ ID NOs: 2-6, and (iii) HVR-H3 from the VH sequence of any one of SEQ ID NOs: 2-6;

(c) (i) HVR-H1 from the VH sequence of any one of SEQ ID NOs: 2-6, (ii) HVR-H2 from the VH sequence of any one of SEQ ID NOs: 2-6, (iii) HVR-H3 from the VH sequence of any one of SEQ ID NOs: 2-6, (iv) HVR-L1 from the VL sequence of any one of SEQ ID NOs: 8-10; (v) HVR-L2 from the VL sequence of any one of SEQ ID NOs: 8-10; and (vi) HVR-L3 from the VL sequence of any one of SEQ ID NOs: 8-10;

(d) (i) HVR-L1 from the VL sequence of any one of SEQ ID NOs: 8-10; (ii) HVR-L2 from the VL sequence of any one of SEQ ID NOs: 8-10; and (iii) HVR-L3 from the VL sequence of any one of SEQ ID NOs: 8-10; or (e) (i) HVR-H1 from the VH sequence of any one of SEQ ID NOs: 2-6, (ii) HVR-H2 from the VH sequence of any one of SEQ ID NOs: 2-6, (iii) HVR-H3 from the VH sequence of any one of SEQ ID NOs: 2-6, (iv) HVR-L1 from the VL sequence of any one of SEQ ID NOs: 7; (v) HVR-L2 from the VL sequence of any one of SEQ ID NOs: 7; and (vi) HVR-L3 from the VL sequence of any one of SEQ ID NOs: 7.

In some embodiments, the antibody of the invention is not an antibody comprising (i) HVR-H1 from the VH sequence of SEQ ID NO: 1, (ii) HVR-H2 from the VH sequence of SEQ ID NO: 1, (iii) HVR-H3 from the VH sequence of SEQ ID NO: 1, (iv) HVR-L1 from the VL sequence of SEQ ID NO: 7, (v) HVR-L2 from the VL sequence of SEQ ID NO: 7, and (vi) HVR-L3 from the VL sequence of SEQ ID NO: 7.

In some embodiments, an isolated anti-DENV antibody of the present invention further comprises a heavy chain variable domain framework FR1 comprising the amino acid sequence of SEQ ID NO: 31, FR2 comprising the amino acid sequence of SEQ ID NO: 32, FR3 comprising the amino acid sequence of SEQ ID NO: 33 or 34, FR4 comprising the amino acid sequence of SEQ ID NO: 35. In some embodiments, an isolated anti-DENV antibody of the present invention further comprises a light chain variable domain framework FR1 comprising the amino acid sequence of SEQ ID NO: 36, FR2 comprising the amino acid sequence of SEQ ID NO: 37, FR3 comprising the amino acid sequence of SEQ ID NO: 38, FR4 comprising the amino acid sequence of SEQ ID NO: 39.

In some embodiments, an isolated anti-DENV antibody of the present invention comprises (a) a VH sequence having at least 95% sequence identity to the amino acid sequence of any one of SEQ ID NOs: 2-6; (b) a VL sequence having at least 95% sequence identity to the amino acid sequence of any one of SEQ ID NOs: 8-10; (c) a VH sequence of any one of SEQ ID NOs: 2-6 and a VL sequence of any one of SEQ ID NOs: 8-10; or (d) a VH sequence of any one of SEQ ID NOs: 2-6 and a VL sequence of any one of SEQ ID NOs: 7.

In some embodiments, an isolated anti-DENV antibody of the present invention is a monoclonal antibody. In some embodiments, an isolated anti-DENV antibody of the present invention is a human, humanized, or chimeric antibody. In some embodiments, an isolated anti-DENV antibody of the present invention is an antibody fragment that binds to DENV or DENV E protein. In some embodiments, an isolated anti-DENV antibody of the present invention is a full length IgG antibody.

In some embodiments, an Fc region of an anti-DENV antibody of the present invention comprises Ala at position 234 and Ala at position 235 according to EU numbering. In some embodiments, an Fc region of an anti-DENV antibody of the present invention may be selected from variant Fc regions described herein.

The invention also provides isolated nucleic acids encoding an anti-DENV antibody of the present invention. The invention also provides host cells comprising a nucleic acid of the present invention. The invention also provides a method of producing an antibody comprising culturing a host cell of the present invention so that the antibody is produced.

The invention also provides a pharmaceutical formulation comprising an anti-DENV antibody of the present invention and a pharmaceutically acceptable carrier.

Anti-DENV antibodies of the present invention may be for use as a medicament. In some embodiments, anti-DENV antibodies of the present invention may be for use in treating DENV infection.

Anti-DENV antibodies of the present invention may be used in the manufacture of a medicament. In some embodiments, the medicament is for treatment of a DENV infection.

The invention also provides a method of treating an individual having a DENV infection. In some embodiments, the method comprises administering to the individual an effective amount of an anti-DENV antibody of the present invention. In some embodiments, the method further comprises administering to the individual an additional therapeutic agent, e.g., as described below.

In some embodiments, a variant Fc region of the present invention comprises at least one amino acid alteration in a parent Fc region. In further embodiments, the variant Fc region has a substantially decreased FcγR-binding activity when compared to the parent Fc region. In further embodiments, the variant Fc region does not have a substantially decreased C1q-binding activity when compared to the parent Fc region.

In some embodiments, a variant Fc region of the present invention comprises Ala at position 234, Ala at position 235, according to EU numbering. In further embodiments, the variant Fc region comprises amino acid alterations of any one of the following (a)-(c): (a) positions 267, 268, and 324, (b) positions 236, 267, 268, 324, and 332, and (c) positions 326 and 333; according to EU numbering.

In some embodiments, a variant Fc region of the present invention comprises amino acids selected from the group consisting of: (a) Glu at position 267, (b) Phe at position 268, (c) Thr at position 324, (d) Ala at position 236, (e) Glu at position 332, (f) Ala, Asp, Glu, Met, or Trp at position 326, and (g) Ser at position 333; according to EU numbering.

In some embodiments, a variant Fc region of the present invention further comprises amino acids selected from the group consisting of: (a) Ala at position 434, (b) Ala at position 434, Thr at position 436, Arg at position 438, and Glu at position 440, (c) Leu at position 428, Ala at position 434, Thr at position 436, Arg at position 438, and Glu at position 440, and (d) Leu at position 428, Ala at position 434, Arg at position 438, and Glu at position 440; according to EU numbering.

In some embodiments, a variant Fc region of the present invention comprises any of the amino acid alterations, singly or in combination, as described in Table 4. In some embodiments, a parent Fc region described in the present invention is derived from human IgG1. The invention provides a polypeptide comprising the amino acid sequence of any one of SEQ ID NOs: 51-59.

In some embodiments, a polypeptide comprising a variant Fc region of the present invention is an antibody. In further embodiments, the antibody is an anti-virus antibody. In further embodiments, the antibody comprises a variable region derived from an anti-DENV antibody described herein.

In further embodiments, the antibody comprises:
(a) (i) HVR-H3 comprising the amino acid sequence of SEQ ID NO: 16, (ii) HVR-L3 comprising the amino acid sequence of SEQ ID NO: 27, and (iii) HVR-H2 comprising the amino acid sequence of SEQ ID NO: 13;
(b) (i) HVR-H1 comprising the amino acid sequence of SEQ ID NO: 11, (ii) HVR-H2 comprising the amino acid sequence of SEQ ID NO: 13, and (iii) HVR-H3 comprising the amino acid sequence of SEQ ID NO: 16;
(c) (i) HVR-H1 comprising the amino acid sequence of SEQ ID NO: 11, (ii) HVR-H2 comprising the amino acid sequence of SEQ ID NO: 13, (iii) HVR-H3 comprising the amino acid sequence of SEQ ID NO: 16, (iv) HVR-L1 comprising the amino acid sequence of SEQ ID NO: 21; (v) HVR-L2 comprising the amino acid sequence of SEQ ID NO: 24; and (vi) HVR-L3 comprising the amino acid sequence of SEQ ID NO: 27; or
(d) (i) HVR-L1 comprising the amino acid sequence of SEQ ID NO: 21; (ii) HVR-L2 comprising the amino acid sequence of SEQ ID NO: 24; and (iii) HVR-L3 comprising the amino acid sequence of SEQ ID NO: 27.

In further embodiments, the antibody comprises:
(a) (i) HVR-H3 from the VH sequence of SEQ ID NO: 6, (ii) HVR-L3 from the VL sequence of SEQ ID NO: 10, and (iii) HVR-H2 from the VH sequence of SEQ ID NO: 6;
(b) (i) HVR-H1 from the VH sequence of SEQ ID NO: 6, (ii) HVR-H2 from the VH sequence of SEQ ID NO: 6, and (iii) HVR-H3 from the VH sequence of SEQ ID NO: 6;
(c) (i) HVR-H1 from the VH sequence of SEQ ID NO: 6, (ii) HVR-H2 from the VH sequence of SEQ ID NO: 6, (iii) HVR-H3 from the VH sequence of SEQ ID NO: 6, (iv) HVR-L1 from the VL sequence of SEQ ID NO: 10; (v) HVR-L2 from the VL sequence of SEQ ID NO: 10; and (vi) HVR-L3 from the VL sequence of SEQ ID NO: 10;
(d) (i) HVR-L1 from the VL sequence of SEQ ID NO: 10; (ii) HVR-L2 from the VL sequence of SEQ ID NO: 10; and (iii) HVR-L3 from the VL sequence of SEQ ID NO: 10; or
(e) (i) HVR-H1 from the VH sequence of SEQ ID NO: 6, (ii) HVR-H2 from the VH sequence of SEQ ID NO: 6, (iii) HVR-H3 from the VH sequence of SEQ ID NO: 6, (iv) HVR-L1 from the VL sequence of SEQ ID NO: 7;
(v) HVR-L2 from the VL sequence of SEQ ID NO: 7; and (vi) HVR-L3 from the VL sequence of SEQ ID NO: 7;

The invention also provides isolated nucleic acids encoding a polypeptide comprising a variant Fc region of the present invention. The invention also provides host cells comprising a nucleic acid of the present invention. The invention also provides a method of producing a polypeptide comprising a variant Fc region comprising culturing a host of the present invention so that the polypeptide is produced.

The invention also provides a pharmaceutical formulation comprising a polypeptide comprising a variant Fc region of the present invention and a pharmaceutically acceptable carrier.

Polypeptides comprising variant Fc regions of the present invention may be for use as a medicament. In some embodiments, polypeptides comprising variant Fc regions of the present invention may be for use in treating a viral infection.

Polypeptides comprising variant Fc regions of the present invention may be used in the manufacture of a medicament. In some embodiments, the medicament is for treatment of a viral infection.

The invention also provides a method of treating an individual having a viral infection. In some embodiments, the method comprises administering to the individual an effective amount of a polypeptide comprising a variant Fc region of the present invention.

The invention also provides an anti-DENV antibody described herein, further comprising a polypeptide comprising a variant Fc region of the present invention.

In one embodiment the present invention refers to a process for preparing an antibody comprising: (a) HVR-H1 comprising the amino acid sequence of SEQ ID NO: 12, (b) HVR-H2 comprising the amino acid sequence of SEQ ID NO: 15, (c) HVR-H3 comprising the amino acid sequence of SEQ ID NO: 20, (d) HVR-L1 comprising the amino acid sequence of SEQ ID NO: 21, (e) HVR-L2 comprising the amino acid sequence of SEQ ID NO: 24 and (f) HVR-L3 comprising the amino acid sequence of SEQ ID NO: 27, the process comprising the steps of:
(a) combining a VH variant sequence selected from the group consisting of: 3CH1047 (SEQ ID NO: 6), and 3CH1049 (SEQ ID NO: 95) with a human IgG1 CH sequence selected from the group consisting of: SG182 (SEQ ID NO: 46), SG1095 (SEQ ID NO: 54) and SG1106 (SEQ ID NO: 59);
(b) combining a VL variant sequence selected from the group consisting of 3CL (SEQ ID NO: 7) and 3CL633 (SEQ ID NO: 98), with a human CL sequence SK1 (SEQ ID NO: 60);
(c) cloning each one of the combinations in an expression vector;
(d) expressing the resulting expression vectors in co-transfected cells (host cells); and
(e) purifying the resulting antibody from step (d).

DETAILED DESCRIPTION OF EMBODIMENTS OF THE INVENTION

Figure 1:
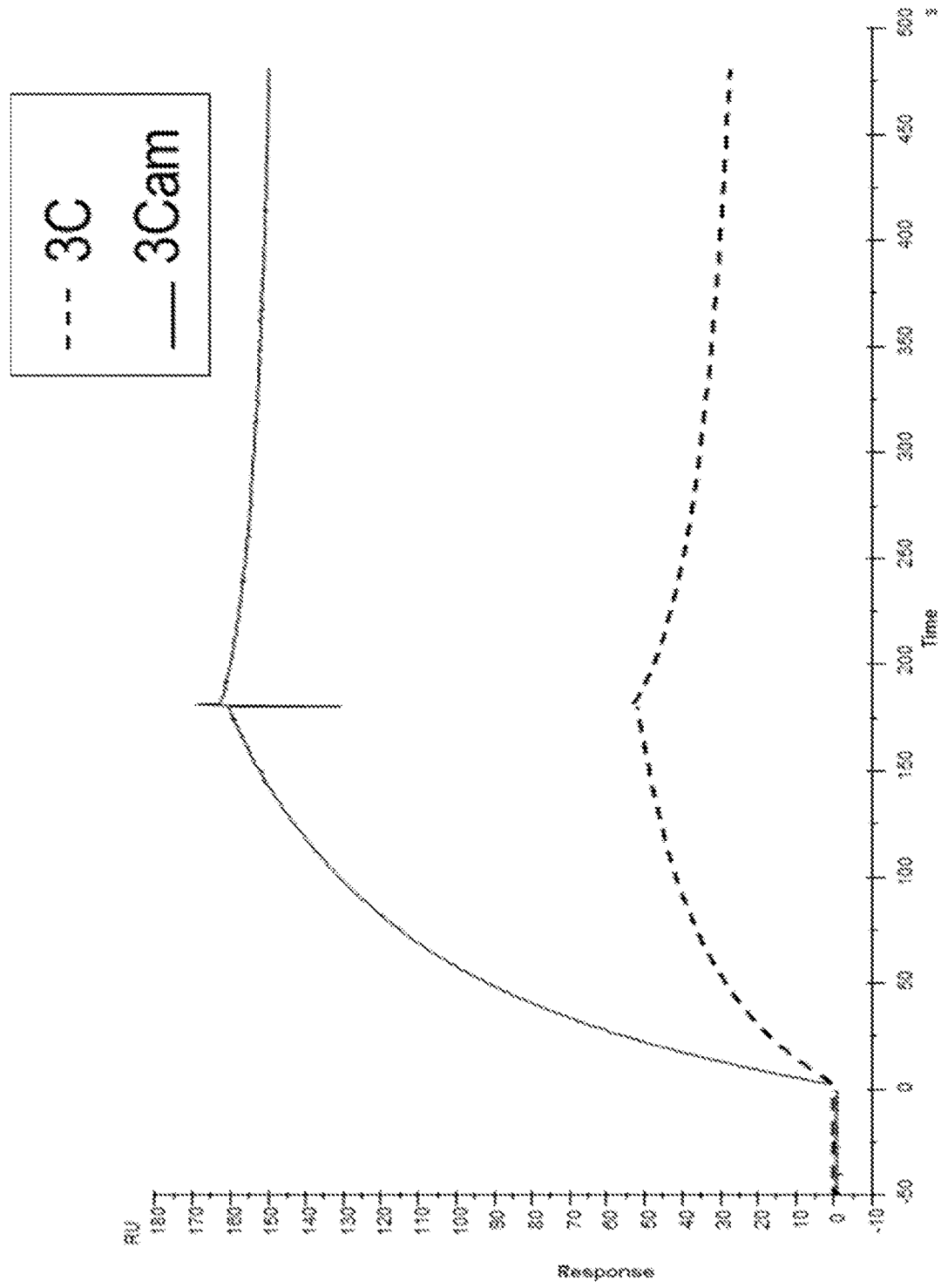
FIGS. 1 (A)-(D) illustrate BIACORE® sensorgrams of anti-DENV antibodies 3C and 3Cam towards DENV-1 E protein (A), DENV-2 E protein (B), DENV-3 E protein (C), and DENV-4 E protein (D), as described in Example 2.
Figure 1B:
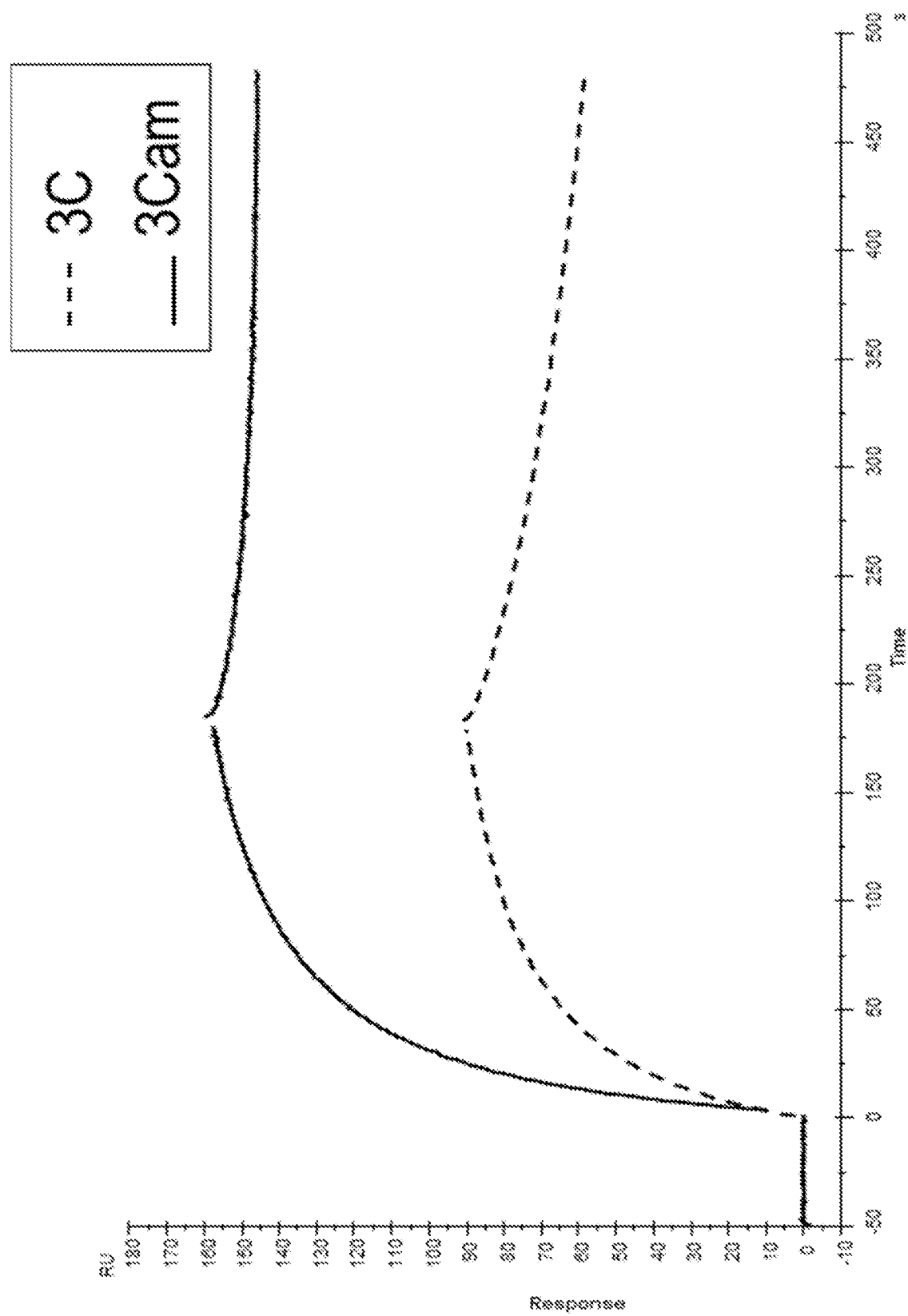
Figure 1:
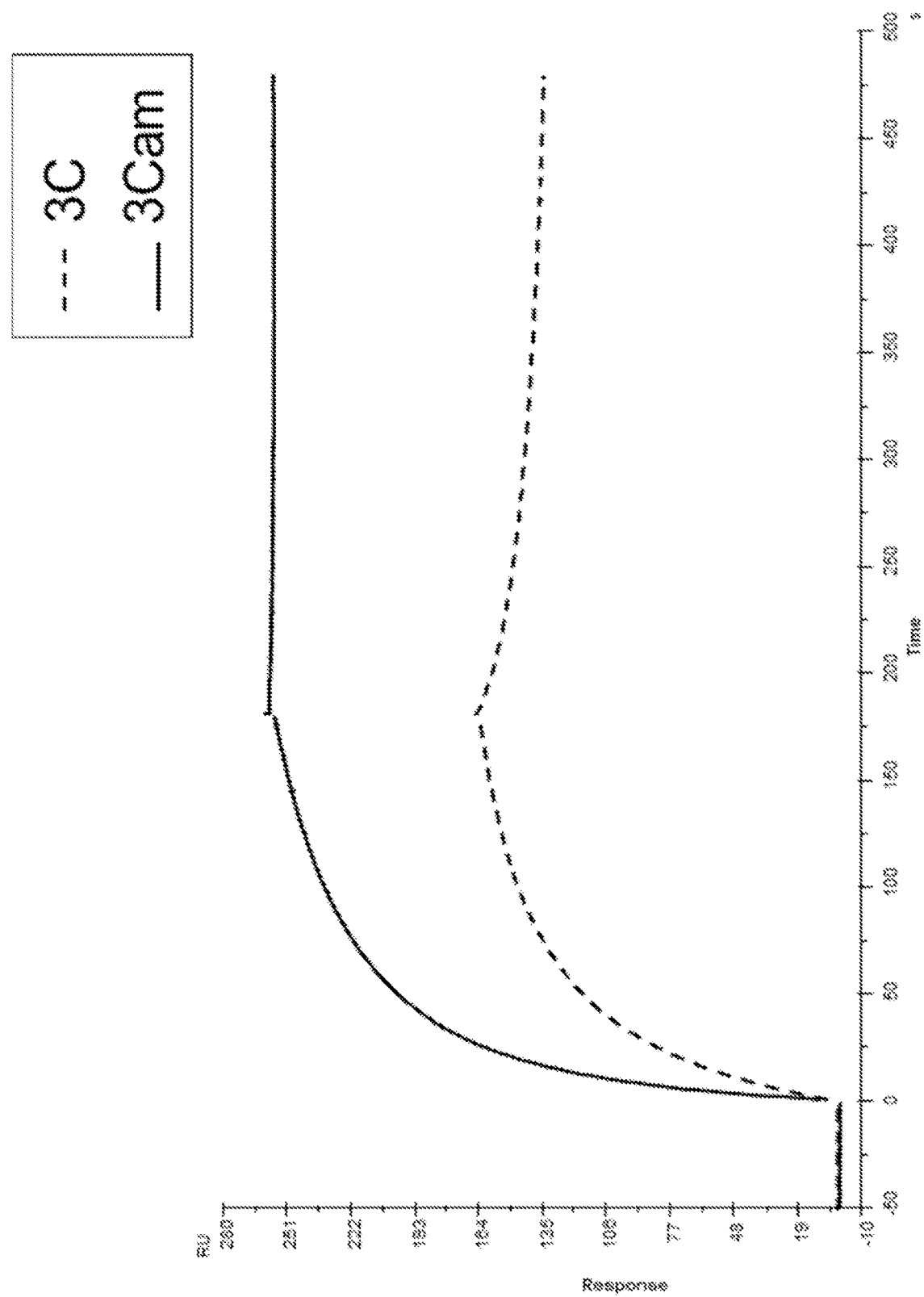
Figure 1:
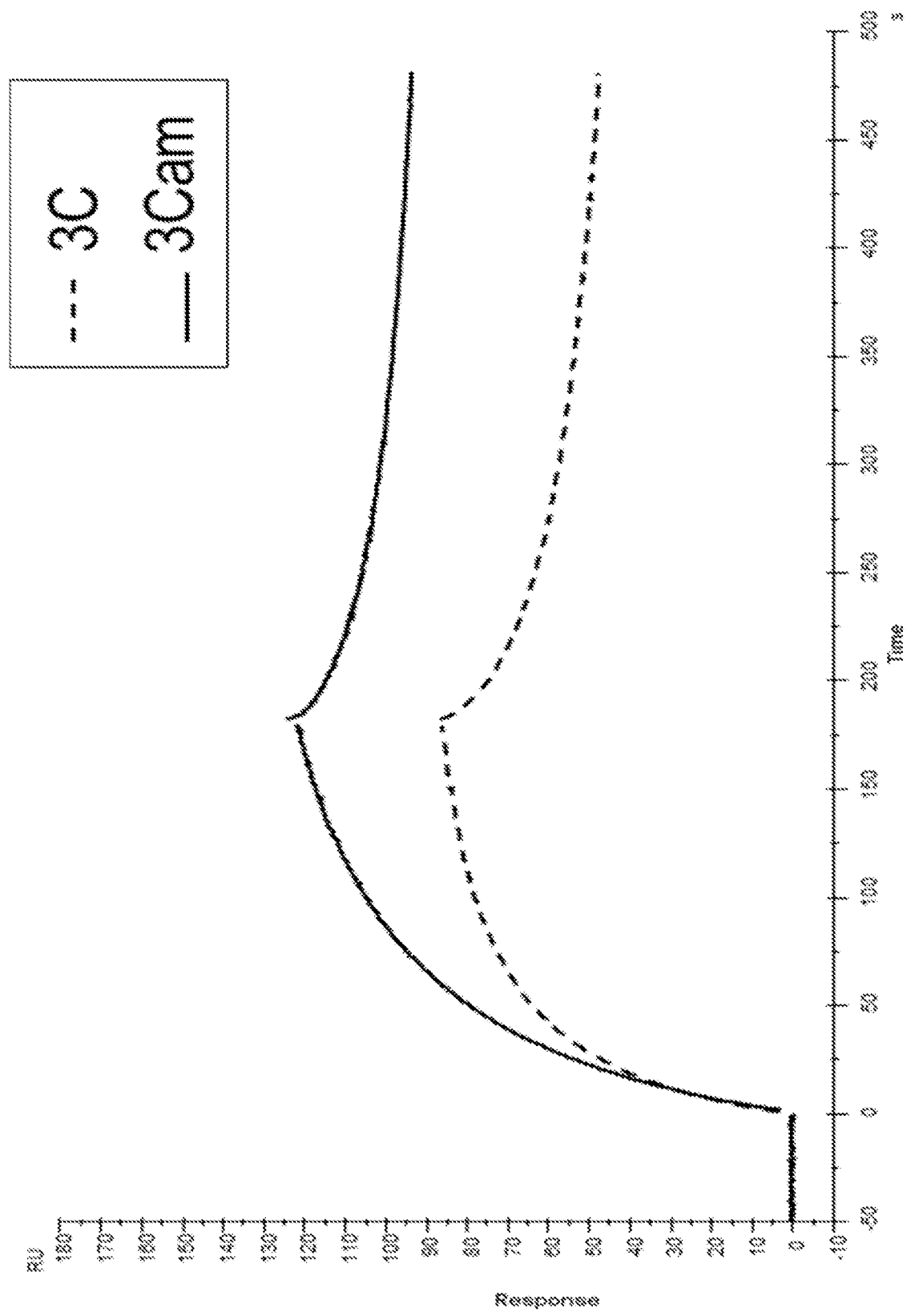

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al., eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty, ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane, Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993).

I. DEFINITIONS

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-DENV antibody" and "an antibody that binds to DENV" refer to an antibody that is capable of binding DENV with sufficient affinity such that the antibody is useful as a diagnostic and/or therapeutic agent in targeting DENV. The antibody may bind to E protein of DENV. The terms "anti-DENV E protein antibody" and "an antibody that binds to DENV E protein" refer to an antibody that is capable of binding DENV E protein with sufficient affinity such that the antibody is useful as a diagnostic and/or therapeutic agent in targeting DENV. In one embodiment, the extent of binding of an anti-DENV E protein antibody to an unrelated protein which is not DENV E protein is less than about 10% of the binding of the antibody to DENV E protein as measured, e.g., by a radioimmunoassay (RIA). In certain embodiments, an antibody that binds to DENV and/or DENV E protein has a dissociation constant (Kd) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$ M, e.g., from $10^{-9}$ M to $10^{-13}$ M). In certain embodiments, an anti-DENV antibody binds to an epitope of DENV that is conserved among DENV from different serotypes. In certain embodiments, an anti-DENV E protein antibody binds to an epitope of DENV E protein that is conserved among DENV E protein from different serotypes.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express Fc gamma RIII only, whereas monocytes express Fc gamma RI, Fc gamma RII, and Fc gamma RIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay, and conversely, the reference antibody blocks binding of the antibody to its antigen in a competition assay. An exemplary competition assay is provided herein.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e. g. from Quidel, San Diego, CA.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called alpha, delta, epsilon, gamma, and mu, respectively.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "cytotoxic agent" as used herein refers to a substance that inhibits or prevents a cellular function and/or causes cell death or destruction. Cytotoxic agents include, but are not limited to, radioactive isotopes (e.g., $^{211}$At, $^{131}$I, $^{125}$I, $^{90}$Y $^{186}$Re, $^{188}$Re, $^{153}$Sm, $^{212}$Bi, $^{32}$P, $^{212}$Pb and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" includes any determinant capable of being bound by an antibody. An epitope is a region of an antigen that is bound by an antibody that targets that antigen, and includes specific amino acids that directly contact the antibody. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See, e.g., Daeron, *Annu. Rev. Immunol.* 15:203-234 (1997).) FcRs are reviewed, for example, in Ravetch and Kinet, *Annu. Rev. Immunol.* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward, *Immunol. Today* 18(12):592-598 (1997); Ghetie et al., *Nature Biotechnology* 15(7):637-640 (1997); Hinton et al., *J. Biol. Chem.* 279(8):6213-6216 (2004); WO 2004/92219 (Hinton et al.). Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al., *J. Biol. Chem.* 9(2):6591-6604 (2001).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991.

The term "Fc region-comprising antibody" refers to an antibody that comprises an Fc region. The C-terminal lysine (residue 447) or glycine-lysine (residues 446-447) of the Fc region may be removed, for example, during purification of the antibody or by recombinant engineering of the nucleic acid encoding the antibody. Accordingly, a composition comprising an antibody having an Fc region according to this invention can comprise an antibody with G446-K447, with G446 and without K447, with all G446-K447 removed, or a mixture of three types of antibodies described above.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody" and "whole antibody" are used herein interchangeably to refer to an antibody having a structure substantially similar to a native antibody structure or having heavy chains that contain an Fc region as defined herein.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g., B cell receptor; BCR), etc. Such effector functions generally require the Fc region to be combined with a binding domain (e.g., an antibody variable domain) and can be assessed using various assays as disclosed, for example, in definitions herein.

The terms "host cell," "host cell line,", "co-transfected cell" and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In certain embodiments, a host cell or co-transfected cell is CHO-DXB11, CHO-K1 or CHO-DG44. Such host cell or co-transfected cell may be a cell expressing taurine transporter, obtained by introducing DNA encoding taurine transporter (WO2007/119774).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "DENV E protein", as used herein, refers to any native DENV E protein from any DENV serotypes, including DENV-1, DENV-2, DENV-3, and DENV-4, unless otherwise indicated. The DENV genome encodes three structural (capsid (C), pre-membrane/membrane (prM/M), and envelope (E)) and seven nonstructural (NS1, NS2A, NS2B, NS3, NS4A, NS4B, and NS5) proteins. The E protein, a glycoprotein of approximately 55 kDa, is present as a heterodimer with PrM protein before the maturation of the virion. X-ray crystallographic studies of the ectodomain of E protein have revealed three distinct beta-barrel domains connected to the viral membrane by a helical stem anchor and two antiparallel transmembrane domains. Domain III (EDIII) adopts an immunoglobulin-like fold and has been suggested to play a critical role in receptor interactions. Domain II (EDII) is an elongated domain composed of two long finger-like structures and contains a highly conserved 13 amino acid fusion loop (EDII-FL) at the tip, and participates in the membrane fusion and dimerization of E protein. The central domain (domain I; EDI) is a nine-stranded β-barrel that is connected to EDIII and EDII by one and four flexible linkers, respectively. E proteins are important for viral assembly, receptor attachment, entry, viral fusion, and possibly immune evasion during the life cycle of the virus and, thus, are dynamic proteins required to adopt several distinct conformations and arrangements on the virus particle. The term encompasses "full-length" unprocessed DENV E protein as well as any form of DENV E protein that results from processing in the cell. The term also encompasses naturally occurring variants of DENV E protein, e.g., serotype variants or quasispecies.

The phrase "substantially decreased", "substantially increased", or "substantially different," as used herein, refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

A "variant Fc region" comprises an amino acid sequence which differs from that of a native sequence Fc region by virtue of at least one amino acid modification (alteration), preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. COMPOSITIONS AND METHODS

In one aspect, the invention is based, in part, on anti-DENV antibodies and uses thereof. In certain embodiments, antibodies that bind to DENV and/or DENV E protein are provided. Antibodies of the invention are useful, e.g., for the diagnosis or treatment of DENV infection.

In one aspect, the invention is based, in part, on polypeptides comprising variant Fc regions and uses thereof. In certain embodiments, polypeptides comprising variant Fc regions with a substantially decreased FcγR-binding activity are provided. In certain embodiments, polypeptides comprising variant Fc regions without a substantially decreased C1q-binding activity are provided. In particular embodiments, the polypeptides of the invention are antibodies. Polypeptides comprising variant Fc regions of the invention are useful, e.g., for the diagnosis or treatment of viral infection.

A. Exemplary Anti-DENV Antibodies and Polypeptides Comprising Variant Fc Regions In one aspect, the invention provides isolated antibodies that bind to DENV and/or DENV E protein. In certain embodiments, an anti-DENV antibody blocks binding of DENV and/or DENV E protein to a host cell. In certain embodiments, an anti-DENV antibody inhibits DENV entry into a host cell. In certain embodiments, an anti-DENV antibody binds to a whole DENV particle. In further embodiments, the antibody binds to a whole DENV particle better than to a monomeric DENV E protein. In certain embodiments, an anti-DENV antibody of the present invention binds to and/or neutralizes at least one, at least two, at least three, or all four DENV serotypes selected from the group consisting of DENV serotype 1 (DENV-1), DENV serotype 2 (DENV-2), DENV serotype 3 (DENV-3), and DENV serotype 4 (DENV-4). In certain embodiments, the anti-DENV antibody binds to and/or neutralizes DENV E protein derived from at least one, at least two, at least three, or all four DENV serotypes selected from the group consisting of DENV-1, DENV-2, DENV-3, and DENV-4. A "serotype" refers to distinct variations within a virus species.

In one aspect, the invention provides an anti-DENV antibody comprising at least one, two, three, four, five, or six HVRs selected from (a) HVR-H1 comprising the amino acid sequence of any one of SEQ ID NOs: 11-12; (b) HVR-H2 comprising the amino acid sequence of any one of SEQ ID NOs: 13-15; (c) HVR-H3 comprising the amino acid sequence of any one of SEQ ID NOs: 16-20; (d) HVR-L1 comprising the amino acid sequence of any one of SEQ ID NOs: 21-23; (e) HVR-L2 comprising the amino acid sequence of any one of SEQ ID NOs: 24-26; and (f) HVR-L3 comprising the amino acid sequence of any one of SEQ ID NOs: 27-30.

In another aspect, the invention provides an anti-DENV antibody comprising at least one, two, three, four, five, or six HVRs selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44; and (f) HVR-L3 comprising the amino acid sequence of SEQ ID NO: 45.

In another aspect, the invention provides an anti-DENV antibody comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 15; (c) HVR-H3 comprising the amino acid sequence of SEQ ID NO: 20; (d) HVR-L1 comprising the amino acid sequence of SEQ ID NO: 23; (e) HVR-L2 comprising the amino acid sequence of SEQ ID NO: 26; and (f) HVR-L3 comprising the amino acid sequence of SEQ ID NO: 30.

In another aspect, the invention provides an anti-DENV antibody comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 15; (c) HVR-H3 comprising the amino acid sequence of SEQ ID NO: 20; (d) HVR-L1 comprising the amino acid sequence of SEQ ID NO: 21; (e) HVR-L2 comprising the amino acid sequence of SEQ ID NO: 24; and (f) HVR-L3 comprising the amino acid sequence of SEQ ID NO: 27.

In one aspect, the invention provides an antibody comprising at least one, at least two, or all three VH HVR sequences selected from (a) HVR-H1 comprising the amino acid sequence of any one of SEQ ID NOs: 11-12; (b) HVR-H2 comprising the amino acid sequence of any one of SEQ ID NOs: 13-15; and (c) HVR-H3 comprising the amino acid sequence of any one of SEQ ID NOs: 16-20. In one embodiment, the antibody comprises HVR-H3 comprising the amino acid sequence of any one of SEQ ID NOs: 16-20. In another embodiment, the antibody comprises HVR-H3 comprising the amino acid sequence of any one of SEQ ID NOs: 16-20 and HVR-L3 comprising the amino acid sequence of any one of SEQ ID NOs: 27-30. In a further embodiment, the antibody comprises HVR-H3 comprising the amino acid sequence of any one of SEQ ID NOs: 16-20, HVR-L3 comprising the amino acid sequence of any one of SEQ ID NOs: 27-30, and HVR-H2 comprising the amino acid sequence of any one of SEQ ID NOs: 13-15. In a further embodiment, the antibody comprises (a) HVR-H1 comprising the amino acid sequence of any one of SEQ ID NOs: 11-12; (b) HVR-H2 comprising the amino acid sequence of any one of SEQ ID NOs: 13-15; and (c) HVR-H3 comprising the amino acid sequence of any one of SEQ ID NOs: 16-20.

In another aspect, the invention provides an antibody comprising at least one, at least two, or all three VH HVR sequences selected from (a) HVR-H1 comprising the amino acid sequence of SEQ ID NO: 40; (b) HVR-H2 comprising the amino acid sequence of SEQ ID NO: 41; and (c) HVR-H3 comprising the amino acid sequence of SEQ ID NO: 42. In one embodiment, the antibody comprises HVR-H3 comprising the amino acid sequence of SEQ ID NO: 42. In another embodiment, the antibody comprises HVR-H3 comprising the amino acid sequence of SEQ ID NO: 42 and HVR-L3 comprising the amino acid sequence of SEQ ID NO: 45. In a further embodiment, the antibody comprises HVR-H3 comprising the amino acid sequence of SEQ ID NO: 42, HVR-L3 comprising the amino acid sequence of SEQ ID NO: 45, and HVR-H2 comprising the amino acid sequence of SEQ ID NO: 41. In a further embodiment, the antibody comprises (a) HVR-H1 comprising the amino acid sequence of SEQ ID NO: 40; (b) HVR-H2 comprising the amino acid sequence of SEQ ID NO: 41; and (c) HVR-H3 comprising the amino acid sequence of SEQ ID NO: 42.

In another aspect, the invention provides an antibody comprising at least one, at least two, or all three VH HVR sequences selected from (a) HVR-H1 comprising the amino acid sequence of SEQ ID NO: 12; (b) HVR-H2 comprising the amino acid sequence of SEQ ID NO: 15; and (c) HVR-H3 comprising the amino acid sequence of SEQ ID NO: 20. In one embodiment, the antibody comprises HVR-H3 comprising the amino acid sequence of SEQ ID NO: 20. In another embodiment, the antibody comprises HVR-H3 comprising the amino acid sequence of SEQ ID NO: 20 and HVR-L3 comprising the amino acid sequence of SEQ ID NO: 27. In a further embodiment, the antibody comprises HVR-H3 comprising the amino acid sequence of SEQ ID NO: 20, HVR-L3 comprising the amino acid sequence of SEQ ID NO: 30, and HVR-H2 comprising the amino acid sequence of SEQ ID NO: 15. In a further embodiment, the antibody comprises HVR-H3 comprising the amino acid sequence of SEQ ID NO: 20, HVR-L3 comprising the amino acid sequence of SEQ ID NO: 27, and HVR-H2 comprising the amino acid sequence of SEQ ID NO: 15. In a further embodiment, the antibody comprises (a) HVR-H1 comprising the amino acid sequence of SEQ ID NO: 12; (b) HVR-H2 comprising the amino acid sequence of SEQ ID NO: 15; and (c) HVR-H3 comprising the amino acid sequence of SEQ ID NO: 20.

In another aspect, the invention provides an antibody comprising at least one, at least two, or all three VL HVR sequences selected from (a) HVR-L1 comprising the amino acid sequence of any one of SEQ ID NOs: 21-23; (b) HVR-L2 comprising the amino acid sequence of any one of SEQ ID NOs: 24-26; and (c) HVR-L3 comprising the amino acid sequence of any one of SEQ ID NOs: 27-30. In one embodiment, the antibody comprises (a) HVR-L1 comprising the amino acid sequence of any one of SEQ ID NOs: 21-23; (b) HVR-L2 comprising the amino acid sequence of any one of SEQ ID NOs: 24-26; and (c) HVR-L3 comprising the amino acid sequence of any one of SEQ ID NOs: 27-30.

In another aspect, the invention provides an antibody comprising at least one, at least two, or all three VL HVR sequences selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45. In one embodiment, the antibody comprises (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, the invention provides an antibody comprising at least one, at least two, or all three VL HVR sequences selected from (a) HVR-L1 comprising the amino acid sequence of SEQ ID NO: 23; (b) HVR-L2 comprising the amino acid sequence of SEQ ID NO: 26; and (c) HVR-L3 comprising the amino acid sequence of SEQ ID NO: 30. In one embodiment, the antibody comprises (a) HVR-L1 comprising the amino acid sequence of SEQ ID NO: 23; (b) HVR-L2 comprising the amino acid sequence of SEQ ID NO: 26; and (c) HVR-L3 comprising the amino acid sequence of SEQ ID NO: 30.

In another aspect, an antibody of the invention comprises (a) a VH domain comprising at least one, at least two, or all three VH HVR sequences selected from (i) HVR-H1 comprising the amino acid sequence of any one of SEQ ID NOs: 11-12, (ii) HVR-H2 comprising the amino acid sequence of any one of SEQ ID NOs: 13-15, and (iii) HVR-H3 comprising an amino acid sequence of any one of SEQ ID NOs: 16-20; and (b) a VL domain comprising at least one, at least two, or all three VL HVR sequences selected from (i) HVR-L1 comprising the amino acid sequence of any one of SEQ ID NOs: 21-23, (ii) HVR-L2 comprising the amino acid sequence of any one of SEQ ID NOs: 24-26, and (iii) HVR-L3 comprising the amino acid sequence of any one of SEQ ID NOs: 27-30.

In another aspect, an antibody of the invention comprises (a) a VH domain comprising at least one, at least two, or all three VH HVR sequences selected from (i) HVR-H1 comprising the amino acid sequence of SEQ ID NO: 40, (ii) HVR-H2 comprising the amino acid sequence of SEQ ID NO: 41, and (iii) HVR-H3 comprising an amino acid sequence of SEQ ID NO: 42; and (b) a VL domain comprising at least one, at least two, or all three VL HVR sequences selected from (i) HVR-L1 comprising the amino acid sequence of SEQ ID NO: 43, (ii) HVR-L2 comprising the amino acid sequence of SEQ ID NO: 44, and (iii) HVR-L3 comprising the amino acid sequence of SEQ ID NO: 45.

In another aspect, an antibody of the invention comprises (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 15, and (iii) HVR-H3 comprising an amino acid sequence of SEQ ID NO: 20; and (b) a VL domain comprising at least one, at least two, or all three VL HVR sequences selected from (i) HVR-L1 comprising the amino acid sequence of SEQ ID NO: 23, (ii) HVR-L2 comprising the amino acid sequence of SEQ ID NO: 26, and (iii) HVR-L3 comprising the amino acid sequence of SEQ ID NO: 30.

In another aspect, an antibody of the invention comprises (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 15, and (iii) HVR-H3 comprising an amino acid sequence of SEQ ID NO: 20; and (b) a VL domain comprising at least one, at least two, or all three VL HVR sequences selected from (i) HVR-L1 comprising the amino acid sequence of SEQ ID NO: 21, (ii) HVR-L2 comprising the amino acid sequence of SEQ ID NO: 24, and (iii) HVR-L3 comprising the amino acid sequence of SEQ ID NO: 27.

In another aspect, the invention provides an antibody comprising (a) HVR-H1 comprising the amino acid sequence of any one of SEQ ID NOs: 11-12; (b) HVR-H2 comprising the amino acid sequence of any one of SEQ ID NOs: 13-15; (c) HVR-H3 comprising the amino acid sequence of any one of SEQ ID NOs: 16-20; (d) HVR-L1 comprising the amino acid sequence of any one of SEQ ID NOs: 21-23; (e) HVR-L2 comprising the amino acid sequence of any one of SEQ ID NOs: 24-26; and (f) HVR-L3 comprising an amino acid sequence of any one of SEQ ID NOs: 27-30.

In another aspect, the invention provides an antibody comprising (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44; and (f) HVR-L3 comprising an amino acid sequence of SEQ ID NO: 45.

In another aspect, the invention provides an antibody comprising (a) HVR-H1 comprising the amino acid sequence of SEQ ID NO: 12; (b) HVR-H2 comprising the amino acid sequence of SEQ ID NO: 15; (c) HVR-H3 comprising the amino acid sequence of SEQ ID NO: 20; (d) HVR-L1 comprising the amino acid sequence of SEQ ID NO: 23; (e) HVR-L2 comprising the amino acid sequence of SEQ ID NO: 26; and (f) HVR-L3 comprising an amino acid sequence of SEQ ID NO: 30.

In another aspect, the invention provides an antibody comprising (a) HVR-H1 comprising the amino acid sequence of SEQ ID NO: 12; (b) HVR-H2 comprising the amino acid sequence of SEQ ID NO: 15; (c) HVR-H3 comprising the amino acid sequence of SEQ ID NO: 20; (d) HVR-L1 comprising the amino acid sequence of SEQ ID NO: 21; (e) HVR-L2 comprising the amino acid sequence of SEQ ID NO: 24; and (f) HVR-L3 comprising an amino acid sequence of SEQ ID NO: 27.

In certain embodiments, any one or more amino acids of an anti-DENV antibody as provided above are substituted at the following HVR positions: (a) in HVR-H1 (SEQ ID NO: 11), at positions 2, and 4; (b) in HVR-H2 (SEQ ID NO: 13), at positions 9, and 10; (c) in HVR-H3 (SEQ ID NO: 16), at positions 3, 14, and 16; (d) in HVR-L1 (SEQ ID NO: 21), at positions 5, and 8; (e) in HVR-L2 (SEQ ID NO:24), at positions 4, and 7; and (f) in HVR-L3 (SEQ ID NO:27), at positions 4, and 5.

In certain embodiments, the one or more amino acid substitutions of an anti-DENV antibody are conservative substitutions, as provided herein. In certain embodiments, any one or more of the following substitutions may be made in any combination: (a) in HVR-H1 (SEQ ID NO: 11), N2Y; I4M; (b) in HVR-H2 (SEQ ID NO: 13), T9R; A10R; (c) in HVR-H3 (SEQ ID NO: 16), R3E; R14F; G16D or L; (d) in HVR-L1 (SEQ ID NO: 21), D5E; K8Q; (e) in HVR-L2 (SEQ ID NO: 24), N4E; T7F; and (f) in HVR-L3 (SEQ ID NO: 27), D4S or E; D5A.

All possible combinations of the above substitutions are encompassed by the consensus sequences of SEQ ID NOs: 40, 41, 42, 43, 44, and 45 for HVR-H1, HVR-H2, HVR-H3, HVR-L1, HVR-L2, and HVR-L3, respectively.

In a further embodiment, an anti-DENV antibody of the invention is not an antibody comprising (i) HVR-H1 comprising the amino acid sequence of SEQ ID NO: 11, (ii) HVR-H2 comprising the amino acid sequence of SEQ ID NO: 13, (iii) HVR-H3 comprising the amino acid sequence of SEQ ID NO: 16, (iv) HVR-L1 comprising the amino acid sequence of SEQ ID NO: 21, (v) HVR-L2 comprising the amino acid sequence of SEQ ID NO: 24, and (vi) HVR-L3 comprising the amino acid sequence of SEQ ID NO: 27.

In another aspect, the invention provides an anti-DENV antibody comprising at least one, two, three, four, five, or six HVRs selected from (a) HVR-H1 from the VH sequence of any one of SEQ ID NOs: 2-6; (b) HVR-H2 from the VH sequence of any one of SEQ ID NOs: 2-6; (c) HVR-H3 from the VH sequence of any one of SEQ ID NOs: 2-6; (d) HVR-L1 from the VL sequence of any one of SEQ ID NOs: 8-10; (e) HVR-L2 from the VL sequence of any one of SEQ ID NOs: 8-10; and (f) HVR-L3 from the VL sequence of any one of SEQ ID NOs: 8-10.

In another aspect, the invention provides an anti-DENV antibody comprising at least one, two, three, four, five, or six HVRs selected from (a) HVR-H1 from the VH sequence of any one of SEQ ID NOs: 2-6; (b) HVR-H2 from the VH sequence of any one of SEQ ID NOs: 2-6; (c) HVR-H3 from the VH sequence of any one of SEQ ID NOs: 2-6; (d) HVR-L1 from the VL sequence of any one of SEQ ID NOs: 7; (e) HVR-L2 from the VL sequence of any one of SEQ ID NOs: 7; and (f) HVR-L3 from the VL sequence of any one of SEQ ID NOs: 7.

In another aspect, the invention provides an anti-DENV antibody comprising at least one, two, three, four, five, or six HVRs selected from (a) HVR-H1 from the VH sequence of SEQ ID NO: 6; (b) HVR-H2 from the VH sequence of SEQ ID NO: 6; (c) HVR-H3 from the VH sequence of SEQ ID NO: 6; (d) HVR-L1 from the VL sequence of SEQ ID NO: 10; (e) HVR-L2 from the VL sequence of SEQ ID NO: 10; and (f) HVR-L3 from the VL sequence of SEQ ID NO: 10.

In another aspect, the invention provides an anti-DENV antibody comprising at least one, two, three, four, five, or six HVRs selected from (a) HVR-H1 from the VH sequence of SEQ ID NO: 6; (b) HVR-H2 from the VH sequence of SEQ ID NO: 6; (c) HVR-H3 from the VH sequence of SEQ ID NO: 6; (d) HVR-L1 from the VL sequence of SEQ ID NO: 7; (e) HVR-L2 from the VL sequence of SEQ ID NO: 7; and (f) HVR-L3 from the VL sequence of SEQ ID NO: 7.

In one aspect, the invention provides an antibody comprising at least one, at least two, or all three VH HVR sequences selected from (a) HVR-H1 from the VH sequence of any one of SEQ ID NOs: 2-6; (b) HVR-H2 from the VH sequence of any one of SEQ ID NOs: 2-6; and (c) HVR-H3 from the VH sequence of any one of SEQ ID NOs: 2-6. In one embodiment, the antibody comprises HVR-H3 from the VH sequence of any one of SEQ ID NOs: 2-6. In another embodiment, the antibody comprises HVR-H3 from the VH sequence of any one of SEQ ID NOs: 2-6 and HVR-L3 from the VL sequence of any one of SEQ ID NOs: 8-10. In another embodiment, the antibody comprises HVR-H3 from the VH sequence of any one of SEQ ID NOs: 2-6 and HVR-L3 from the VL sequence of any one of SEQ ID NOs: 7. In a further embodiment, the antibody comprises HVR-H3 from the VH sequence of any one of SEQ ID NOs: 2-6, HVR-L3 from the VL sequence of any one of SEQ ID NOs: 8-10, and HVR-H2 from the VH sequence of any one of SEQ ID NOs: 2-6. In a further embodiment, the antibody comprises HVR-H3 from the VH sequence of any one of SEQ ID NOs: 2-6, HVR-L3 from the VL sequence of any one of SEQ ID NOs: 7, and HVR-H2 from the VH sequence of any one of SEQ ID NOs: 2-6. In a further embodiment, the antibody comprises (a) HVR-H1 from the VH sequence of any one of SEQ ID NOs: 2-6; (b) HVR-H2 from the VH sequence of any one of SEQ ID NOs: 2-6; and (c) HVR-H3 from the VH sequence of any one of SEQ ID NOs: 2-6.

In one aspect, the invention provides an antibody comprising at least one, at least two, or all three VH HVR sequences selected from (a) HVR-H1 from the VH sequence of SEQ ID NO: 6; (b) HVR-H2 from the VH sequence of SEQ ID NO: 6; and (c) HVR-H3 from the VH sequence of SEQ ID NO: 6. In one embodiment, the antibody comprises HVR-H3 from the VH sequence of SEQ ID NO: 6. In another embodiment, the antibody comprises HVR-H3 from the VH sequence of SEQ ID NO: 6 and HVR-L3 from the VL sequence of SEQ ID NO: 10. In another embodiment, the antibody comprises HVR-H3 from the VH sequence of SEQ ID NO: 6 and HVR-L3 from the VL sequence of SEQ ID NO: 7. In a further embodiment, the antibody comprises HVR-H3 from the VH sequence of SEQ ID NO: 6, HVR-L3 from the VL sequence of SEQ ID NO: 10, and HVR-H2 from the VH sequence of SEQ ID NO: 6. In a further embodiment, the antibody comprises HVR-H3 from the VH sequence of SEQ ID NO: 6, HVR-L3 from the VL sequence of SEQ ID NO: 7, and HVR-H2 from the VH sequence of SEQ ID NO: 6. In a further embodiment, the antibody comprises (a) HVR-H1 from the VH sequence of SEQ ID NO: 6; (b) HVR-H2 from the VH sequence of SEQ ID NO: 6; and (c) HVR-H3 from the VH sequence of SEQ ID NO: 6.

In another aspect, the invention provides an antibody comprising at least one, at least two, or all three VL HVR sequences selected from (a) HVR-L1 from the VL sequence of any one of SEQ ID NOs: 8-10; (b) HVR-L2 from the VL sequence of any one of SEQ ID NOs: 8-10; and (c) HVR-L3 from the VL sequence of any one of SEQ ID NOs: 8-10. In one embodiment, the antibody comprises (a) HVR-L1 from the VL sequence of any one of SEQ ID NOs: 8-10; (b) HVR-L2 from the VL sequence of any one of SEQ ID NOs: 8-10; and (c) HVR-L3 from the VL sequence of any one of SEQ ID NOs: 8-10.

In another aspect, the invention provides an antibody comprising at least one, at least two, or all three VL HVR sequences selected from (a) HVR-L1 from the VL sequence of SEQ ID NO: 10; (b) HVR-L2 from the VL sequence of SEQ ID NO: 10; and (c) HVR-L3 from the VL sequence of SEQ ID NO: 10. In one embodiment, the antibody comprises (a) HVR-L1 from the VL sequence of SEQ ID NO: 10; (b) HVR-L2 from the VL sequence of SEQ ID NO: 10; and (c) HVR-L3 from the VL sequence of SEQ ID NO: 10.

In another aspect, an antibody of the invention comprises (a) a VH domain comprising at least one, at least two, or all three VH HVR sequences selected from (i) HVR-H1 from the VH sequence of any one of SEQ ID NOs: 2-6, (ii) HVR-H2 from the VH sequence of any one of SEQ ID NOs: 2-6, and (iii) HVR-H3 from the VH sequence of any one of SEQ ID NOs: 2-6; and (b) a VL domain comprising at least one, at least two, or all three VL HVR sequences selected from (i) HVR-L1 from the VL sequence of any one of SEQ ID NOs: 8-10, (ii) HVR-L2 from the VL sequence of any one of SEQ ID NOs: 8-10, and (iii) HVR-L3 from the VL sequence of any one of SEQ ID NOs: 8-10.

In another aspect, an antibody of the invention comprises (a) a VH domain comprising at least one, at least two, or all three VH HVR sequences selected from (i) HVR-H1 from the VH sequence of any one of SEQ ID NOs: 2-6, (ii) HVR-H2 from the VH sequence of any one of SEQ ID NOs: 2-6, and (iii) HVR-H3 from the VH sequence of any one of SEQ ID NOs: 2-6; and (b) a VL domain comprising at least one, at least two, or all three VL HVR sequences selected from (i) HVR-L1 from the VL sequence of any one of SEQ ID NOs: 7, (ii) HVR-L2 from the VL sequence of any one of SEQ ID NOs: 7, and (iii) HVR-L3 from the VL sequence of any one of SEQ ID NOs: 7.

In another aspect, an antibody of the invention comprises (a) a VH domain comprising at least one, at least two, or all three VH HVR sequences selected from (i) HVR-H1 from the VH sequence of SEQ ID NO: 6, (ii) HVR-H2 from the VH sequence of SEQ ID NO: 6, and (iii) HVR-H3 from the VH sequence of SEQ ID NO: 6; and (b) a VL domain comprising at least one, at least two, or all three VL HVR sequences selected from (i) HVR-L1 from the VL sequence of SEQ ID NO: 10, (ii) HVR-L2 from the VL sequence of SEQ ID NO: 10, and (iii) HVR-L3 from the VL sequence of SEQ ID NO: 10.

In another aspect, an antibody of the invention comprises (a) a VH domain comprising at least one, at least two, or all three VH HVR sequences selected from (i) HVR-H1 from the VH sequence of SEQ ID NO: 6, (ii) HVR-H2 from the VH sequence of SEQ ID NO: 6, and (iii) HVR-H3 from the VH sequence of SEQ ID NO: 6; and (b) a VL domain comprising at least one, at least two, or all three VL HVR sequences selected from (i) HVR-L1 from the VL sequence of SEQ ID NO: 7, (ii) HVR-L2 from the VL sequence of SEQ ID NO: 7, and (iii) HVR-L3 from the VL sequence of SEQ ID NO: 7.

In another aspect, the invention provides an antibody comprising (a) HVR-H1 from the VH sequence of any one of SEQ ID NOs: 2-6; (b) HVR-H2 from the VH sequence of any one of SEQ ID NOs: 2-6; (c) HVR-H3 from the VH sequence of any one of SEQ ID NOs: 2-6; (d) HVR-L1 from the VL sequence of any one of SEQ ID NOs: 8-10; (e) HVR-L2 from the VL sequence of any one of SEQ ID NOs: 8-10; and (f) HVR-L3 from the VL sequence of any one of SEQ ID NOs: 8-10.

In another aspect, the invention provides an antibody comprising (a) HVR-H1 from the VH sequence of any one of SEQ ID NOs: 2-6; (b) HVR-H2 from the VH sequence of any one of SEQ ID NOs: 2-6; (c) HVR-H3 from the VH sequence of any one of SEQ ID NOs: 2-6; (d) HVR-L1 from the VL sequence of any one of SEQ ID NOs: 7; (e) HVR-L2 from the VL sequence of any one of SEQ ID NOs: 7; and (f) HVR-L3 from the VL sequence of any one of SEQ ID NOs: 7.

In another aspect, the invention provides an antibody comprising (a) HVR-H1 from the VH sequence of SEQ ID NO: 6; (b) HVR-H2 from the VH sequence of SEQ ID NO: 6; (c) HVR-H3 from the VH sequence of SEQ ID NO: 6; (d) HVR-L1 from the VL sequence of SEQ ID NO: 10; (e) HVR-L2 from the VL sequence of SEQ ID NO: 10; and (f) HVR-L3 from the VL sequence of SEQ ID NO: 10.

In another aspect, the invention provides an antibody comprising (a) HVR-H1 from the VH sequence of SEQ ID NO: 6; (b) HVR-H2 from the VH sequence of SEQ ID NO: 6; (c) HVR-H3 from the VH sequence of SEQ ID NO: 6; (d) HVR-L1 from the VL sequence of SEQ ID NO: 7; (e) HVR-L2 from the VL sequence of SEQ ID NO: 7; and (f) HVR-L3 from the VL sequence of SEQ ID NO: 7.

In a further embodiment, an anti-DENV antibody of the invention is not an antibody comprising (i) HVR-H1 from the VH sequence of SEQ ID NO: 1, (ii) HVR-H2 from the VH sequence of SEQ ID NO: 1, (iii) HVR-H3 from the VH sequence of SEQ ID NO: 1, (iv) HVR-L1 from the VL sequence of SEQ ID NO: 7, (v) HVR-L2 from the VL sequence of SEQ ID NO: 7, and (vi) HVR-L3 from the VL sequence of SEQ ID NO: 7.

In any of the above embodiments, an anti-DENV antibody can be humanized. In one embodiment, an anti-DENV antibody comprises HVRs as in any of the above embodiments, and further comprises an acceptor human framework, e.g. a human immunoglobulin framework or a human consensus framework. In another embodiment, an anti-DENV antibody comprises HVRs as in any of the above embodiments, and further comprises a VH or VL comprising an FR sequence. In a further embodiment, the anti-DENV antibody comprises the following heavy chain and/or light chain variable domain FR sequences: For the heavy chain variable domain, the FR1 comprises the amino acid sequence of SEQ ID NO: 31, FR2 comprises the amino acid sequence of SEQ ID NO: 32, FR3 comprises the amino acid sequence of SEQ ID NO: 33 or 34, FR4 comprises the amino acid sequence of SEQ ID NO: 35. For the light chain variable domain, FR1 comprises the amino acid sequence of SEQ ID NO: 36, FR2 comprises the amino acid sequence of SEQ ID NO: 37, FR3 comprises the amino acid sequence of SEQ ID NO: 38, FR4 comprises the amino acid sequence of SEQ ID NO: 39.

In another aspect, an anti-DENV antibody comprises a heavy chain variable domain (VH) sequence having at least 90%, 91%, 92%, 93%, 94%, 95%, 96%, 97%, 98%, 99%, or 100% sequence identity to the amino acid sequence of any one of SEQ ID NOs: 2-6. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-DENV antibody comprising that sequence retains the ability to bind to DENV. In certain embodiments, a total of 1 to 10 amino acids have been substituted, inserted and/or deleted in any one of SEQ ID NOs: 2-6. In certain embodiments, substitutions, insertions, or deletions occur in regions outside the HVRs (i.e., in the FRs). Optionally, the anti-DENV antibody comprises the VH sequence in any one of SEQ ID NOs: 2-6, including post-translational modifications of that sequence. In a particular embodiment, the VH comprises one, two or three HVRs selected from: (a) HVR-H1 comprising the amino acid sequence of any one of SEQ ID NOs: 11-12, (b) HVR-H2 comprising the amino acid sequence of any one of SEQ ID NOs: 13-15, and (c) HVR-H3 comprising the amino acid sequence of any one of SEQ ID NOs: 16-20. Post-translational modifications include but are not limited to a modification of glutamine or glutamate in N-terminal of heavy chain or light chain to pyroglutamic acid by pyroglutamylation.

In another aspect, an anti-DENV antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 6. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-DENV antibody comprising that sequence retains the ability to bind to DENV. In certain embodiments, a total of 1 to 10 amino acids have been substituted, inserted and/or deleted in SEQ ID NO: 6. In certain embodiments, substitutions, insertions, or deletions occur in regions outside the HVRs (i.e., in the FRs). Optionally, the anti-DENV antibody comprises the VH sequence in SEQ ID NO: 6, including post-translational modifications of that sequence. In a particular embodiment, the VH comprises one, two or three HVRs selected from: (a) HVR-H1 comprising the amino acid sequence of SEQ ID NO: 12, (b) HVR-H2 comprising the amino acid sequence of SEQ ID NO: 15, and (c) HVR-H3 comprising the amino acid sequence of SEQ ID NO: 20. Post-translational modifications include but are not limited to a modification of glutamine or glutamate in N-terminal of heavy chain or light chain to pyroglutamic acid by pyroglutamylation.

In another aspect, an anti-DENV antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of any one of SEQ ID NOs: 8-10. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-DENV antibody comprising that sequence retains the ability to bind to DENV. In certain embodiments, a total of 1 to 10 amino acids have been substituted, inserted and/or deleted in any one of SEQ ID NOs: 8-10. In certain embodiments, the substitutions, insertions, or deletions occur in regions outside the HVRs (i.e., in the FRs). Optionally, the anti-DENV antibody comprises the VL sequence in any one of SEQ ID NOs: 8-10, including post-translational modifications of that sequence. In a particular embodiment, the VL comprises one, two or three HVRs selected from (a) HVR-L1 comprising the amino acid sequence of any one of SEQ ID NOs: 21-23; (b) HVR-L2 comprising the amino acid sequence of any one of SEQ ID NOs: 24-26; and (c) HVR-L3 comprising the amino acid sequence of any one of SEQ ID NOs: 27-30. Post-translational modifications include but are not limited to a modification of glutamine or glutamate in N-terminal of heavy chain or light chain to pyroglutamic acid by pyroglutamylation.

In another aspect, an anti-DENV antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 10. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-DENV antibody comprising that sequence retains the ability to bind to DENV. In certain embodiments, a total of 1 to 10 amino acids have been substituted, inserted and/or deleted in SEQ ID NO: 10. In certain embodiments, the substitutions, insertions, or deletions occur in regions outside the HVRs (i.e., in the FRs). Optionally, the anti-DENV antibody comprises the VL sequence in SEQ ID NO: 10, including post-translational modifications of that sequence. In a particular embodiment, the VL comprises one, two or three HVRs selected from (a) HVR-L1 comprising the amino acid sequence of SEQ ID NO: 23; (b) HVR-L2 comprising the amino acid sequence of SEQ ID NO: 26; and (c) HVR-L3 comprising the amino acid sequence of SEQ ID NO: 30. Post-translational modifications include but are not limited to a modification of glutamine or glutamate in N-terminal of heavy chain or light chain to pyroglutamic acid by pyroglutamylation.

In another aspect, an anti-DENV antibody is provided, wherein the antibody comprises a VH as in any of the embodiments provided above, and a VL as in any of the embodiments provided above. In one embodiment, the antibody comprises the VH and VL sequences in any one of SEQ ID NOs: 2-6 and any one of SEQ ID NOs: 8-10, respectively, including post-translational modifications of those sequences. In one embodiment, the antibody comprises the VH and VL sequences in any one of SEQ ID NOs: 2-6 and SEQ ID NOs: 7, respectively, including post-translational modifications of those sequences. Post-translational modifications include but are not limited to a modification of glutamine or glutamate in N-terminal of heavy chain or light chain to pyroglutamic acid by pyroglutamylation.

In another aspect, an anti-DENV antibody is provided, wherein the antibody comprises a VH as in any of the embodiments provided above, and a VL as in any of the embodiments provided above. In one embodiment, the antibody comprises the VH and VL sequences in SEQ ID NO: 6 and SEQ ID NO: 10, respectively, including post-translational modifications of those sequences. In one embodiment, the antibody comprises the VH and VL sequences in SEQ ID NO: 6 and SEQ ID NO: 7, respectively, including post-translational modifications of those sequences. Post-translational modifications include but are not limited to a modification of glutamine or glutamate in N-terminal of heavy chain or light chain to pyroglutamic acid by pyroglutamylation.

In a further aspect, the invention provides an antibody that binds to the same epitope as an anti-DENV antibody provided herein. In certain embodiments, an antibody is provided that binds to an epitope comprising at least one, at least two, at least three, at least four, at least five, at least six, at least seven, or all of the amino acids selected from the group consisting of G100, W101, K122, I162, S274, K310, W391 and F392 on DENV-2 E protein. In certain embodiments, an antibody is provided that binds to an epitope comprising at least one, at least two, or all of the amino acids selected from the group consisting of K122, I162, and S274 on DENV-2 E protein. In certain embodiments, an antibody is provided that binds to an epitope further comprising at least one of the amino acids selected from the group consisting of G100, W101, K310, W391, and F392, when the epitope comprises at least one, at least two, or all of the amino acids selected from the group consisting of K122, I162, and S274.

In a further aspect of the invention, an anti-DENV antibody according to any of the above embodiments is a monoclonal antibody, including a chimeric, humanized or human antibody. In one embodiment, an anti-DENV antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-DENV antibody of the invention may have a modification that abolishes the binding of antibodies to Fc-gamma-receptors (FcγR). Without wishing to be bound by theory, a modification that abolishes the binding of antibodies to Fc-gamma-receptors may be advantageous because a decreased binding to FcR may avoid the phenomenon of ADE (Antibody-dependent enhancement) of infection, which is thought to be mostly mediated by the interaction with FcR. In one embodiment, an Fc region of an anti-DENV antibody of the invention comprises Ala at position 234 and Ala at position 235 according to EU numbering.

In a further aspect, an anti-DENV antibody according to any of the above embodiments may incorporate any of the features, singly or in combination, as described in Sections 1-7 below:

1. Antibody Affinity

In certain embodiments, an antibody provided herein has a dissociation constant (Kd) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER (registered trademark) multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 micro l/well of scintillant (MICROSCINT-20™, Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE (registered trademark)-3000 (BIAcore, Inc., Piscataway, NJ) is performed at 25 degrees C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 µl/min. Association rates ($k_{on}$) and dissociation rates ($k_{off}$) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab (registered trademark) technology; U.S. Pat. No. 7,041,870 describing K-M MOUSE (registered trademark) technology, and U.S. Patent Application Publication No. US 2007/0061900, describing VelociMouse (registered trademark) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N J, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N J, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for DENV E protein and the other is for any other antigen. In certain embodiments, bispecific antibodies may bind to two different epitopes of DENV E protein. Bispecific antibodies may also be used to localize cytotoxic agents to cells which express DENV E protein. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bispecific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (scFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting Fab" or "DAF" comprising an antigen binding site that binds to DENV E protein as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |

TABLE 1-continued

| Original Residue | Exemplary Substitutions | Preferred Substitutions |
|---|---|---|
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots." i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be analyzed to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of an enzyme (e.g. for ADEPT) or a polypeptide which increases the plasma half-life of the antibody to the N- or C-terminus of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +/−3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as ADCC) are unnecessary or deleterious. In vitro and/or in vivo cytotoxicity assays can be conducted to measure CDC and/or ADCC activities. For example, Fc receptor (FcR) binding assays can be conducted to confirm whether the antibody has Fc gamma R binding (hence likely having ADCC activity) and/or FcRn binding ability. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, CA; and CytoTox 96 (registered trademark) non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95: 652-656 (1998). C1q binding assays may also be carried out to confirm whether the antibody is able to bind C1q and hence has CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with modified effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with altered binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which alter ADCC, e.g., substitutions at positions 298, 333, and/or 334 of the Fc region (EU numbering of residues).

In some embodiments, alterations are made in the Fc region that result in altered (i.e., either increased or decreased) C1q binding and/or Complement Dependent Cytotoxicity (CDC), e.g., as described in U.S. Pat. No. 6,194,551, WO 99/51642, WO2011/091078, and Idusogie et al. *J. Immunol.* 164: 4178-4184 (2000).

Antibodies with increased half lives and increased binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which increase binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In another embodiment, an antibody may comprise a variant Fc region of the present invention described herein below in detail.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In one aspect, the invention provides an isolated polypeptide comprising a variant Fc region with a substantially decreased FcγR-binding activity. In one aspect, the invention provides an isolated polypeptide comprising a variant Fc region without a substantially decreased C1q-binding activity. In one aspect, the invention provides an isolated polypeptide comprising a variant Fc region with a substantially decreased FcγR-binding activity and without a substantially decreased C1q-binding activity. In some aspects, the polypeptide is an antibody. In some aspects, the polypeptide is an Fc fusion protein. In certain embodiments, the variant Fc region comprises at least one amino acid residue alteration (e.g., substitution) compared to the corresponding sequence in the Fc region of a native or reference variant sequence (sometimes collectively referred to herein as a "parent" Fc region). In certain embodiments, the variant Fc region of the invention has a substantially decreased FcγR-binding activity compared to the parent Fc region. In certain embodiments, the variant Fc region of the invention does not have a substantially decreased C1q-binding activity compared to the parent Fc region. In certain embodiments, FcγR is human FcγR, monkey FcγR (e.g., cynomolgus, rhesus macaque, marmoset, chimpanzee, or baboon FcγR), or mouse FcγR.

In one aspect, a variant Fc region of the invention has a substantially decreased binding activity for one or more human FcγRs including, but not limited to FcγRIa, FcγRIIa (including allelic variants 167H and 167R), FcγRIIb, FcγRIIIa (including allelic variants 158F and 158V), and FcγRIIIb (including allelic variants NA1 and NA2), as compared to a parent Fc region. In a further aspect, a variant Fc region of the invention has a substantially decreased binding activity for human FcγRIa, FcγRIIa (including allelic variants 167H and 167R), FcγRIIb, FcγRIIIa (including allelic variants 158F and 158V), and FcγRIIIb (including allelic variants NA1 and NA2), as compared to a parent Fc region.

In one aspect, a variant Fc region of the invention has a substantially decreased binding activity for one or more mouse FcγRs including, but not limited to FcγRI, FcγRIIb, FcγRIII, and FcγRIV, as compared to a parent Fc region. In a further aspect, a variant Fc region of the invention has a substantially decreased binding activity for mouse FcγRI, FcγRIIb, FcγRIII, and FcγRIV, as compared to a parent Fc region.

"Fcγ receptors" (herein, referred to as Fcγ receptors, FcγR or FcgR) refers to receptors that may bind to the Fc region of IgG1, IgG2, IgG3, and IgG4 monoclonal antibodies, and practically means any member of the family of proteins encoded by the Fcγ receptor genes. In humans, this family includes FcγRI (CD64) including isoforms FcγRIa, FcγRIb, and FcγRIc; FcγRII (CD32) including isoforms FcγRIIa (including allotypes H131 (type H) and R131 (type R)), FcγRIIb (including FcγRIIb-1 and FcγRIIb-2), and FcγRIIc; and FcγRIII (CD16) including isoforms FcγRIIIa (including allotypes V158 and F158), and FcγRIIIb (including allotypes FcγRIIIb-NA1 and FcγRIIIb-NA2), and any human FcγRs, FcγR isoforms or allotypes yet to be discovered, but is not limited thereto. FcγRIIb1 and FcγRIIb2 have been reported as splicing variants of human FcγRIIb. In addition, a splicing variant named FcγRIIb3 has been reported (J Exp Med, 1989, 170: 1369-1385). In addition to these splicing variants, human FcγRIIb includes all splicing variants registered in NCBI, which are NP_001002273.1, NP_001002274.1, NP 001002275.1, NP_001177757.1, and NP_003992.3. Furthermore, human FcγRIIb includes every previously-reported genetic polymorphism, as well as FcγRIIb (*Arthritis Rheum.* 48:3242-3252 (2003); Kono et al., *Hum. Mol. Genet.* 14:2881-2892 (2005); and Kyogoju et al., *Arthritis Rheum.* 46:1242-1254 (2002)), and every genetic polymorphism that will be reported in the future.

In FcγRIIa, there are two allotypes, one where the amino acid at position 167 of FcγRIIa is histidine (type H) and the other where the amino acid at position 167 is substituted with arginine (type R) (Warrmerdam, *J. Exp. Med.* 172:19-25 (1990)).

The FcγR includes human, mouse, rat, rabbit, and monkey-derived FcγRs but is not limited thereto, and may be derived from any organism. Mouse FcγRs include FcγRI (CD64), FcγRII (CD32), FcγRIII (CD16), and FcγRIV (CD16-2), and any mouse FcγRs, or FcγR isoforms, but are not limited thereto.

The amino acid sequence of human FcγRIa is set forth in SEQ ID NO: 69; the amino acid sequence of human FcγRIIa (167H) is set forth in SEQ ID NO: 70; the amino acid sequence of human FcγRIIa (167R) is set forth in SEQ ID NO: 71; the amino acid sequence of human FcγRIIb is set forth in SEQ ID NO: 72; the amino acid sequence of human FcγRIIIa (158F) is set forth in SEQ ID NO: 73; the amino acid sequence of human FcγRIIIa (158V) is set forth in SEQ ID NO: 74; the amino acid sequence of human FcγRIIIb (NA1) is set forth in SEQ ID NO: 75; and the amino acid sequence of human FcγRIIIb (NA2) is set forth in SEQ ID NO: 76.

The amino acid sequence of mouse FcγRI is set forth in SEQ ID NO: 77; the amino acid sequence of mouse FcγRIIb is set forth in SEQ ID NO: 78; the amino acid sequence of mouse FcγRIII is set forth in SEQ ID NO: 79; and the amino acid sequence of mouse FcγRIV is set forth in SEQ ID NO: 80.

In one aspect, a variant Fc region of the invention has a substantially decreased FcγR-binding activity that is less than 50%, less than 45%, less than 40%, less than 35%, less than 30%, less than 25%, less than 20%, less than 15%, less than 10%, less than 5%, less than 2%, less than 1%, less than 0.5%, less than 0.2%, or less than 0.1% as a function of the FcγR-binding activity for the parent Fc region. In one aspect, a variant Fc region of the invention has a substantially decreased FcγR-binding activity, which means that the ratio of [the difference in the RU values of sensorgrams that changed before and after interaction of FcγR with the variant Fc region]/[the difference in the RU values of sensorgrams that changed before and after capturing FcγR to the sensor chips] is less than 1, less than 0.8, less than 0.5, less than 0.3, less than 0.2, less than 0.1, less than 0.08, less than 0.05, less than 0.03, less than 0.02, less than 0.01, less than 0.008, less than 0.005, less than 0.003, less than 0.002, or less than 0.001.

In one aspect, a variant Fc region of the invention does not have a substantially decreased C1q-binding activity, which means that the difference of C1q-binding activities between a variant Fc region and a parent Fc region of the invention is less than 50%, less than 45%, less than 40%, less than 35%, less than 30%, less than 25%, less than 20%, less than 15%, less than 10%, or less than 5% as a function of the C1q-binding activity for the parent Fc region.

In one aspect, the invention provides an isolated polypeptide comprising a variant Fc region with a substantially decreased ADCC activity. In one aspect, the invention provides an isolated polypeptide comprising a variant Fc region without a substantially decreased CDC activity. In one aspect, the invention provides an isolated polypeptide comprising a variant Fc region with a substantially decreased ADCC activity and without a substantially decreased CDC activity.

In one aspect, a variant Fc region of the invention has a substantially decreased ADCC activity that is less than 50%, less than 45%, less than 40%, less than 35%, less than 30%, less than 25%, less than 20%, less than 15%, less than 10%, less than 5%, less than 2%, less than 1%, less than 0.5%, less than 0.2%, or less than 0.1% as a function of the ADCC activity for the parent Fc region.

In one aspect, a variant Fc region of the invention does not have a substantially decreased CDC activity, which means that the difference of CDC activities between a variant Fc region and a parent Fc region of the invention is less than 50%, less than 45%, less than 40%, less than 35%, less than 30%, less than 25%, less than 20%, less than 15%, less than 10%, or less than 5% as a function of the CDC activity for the parent Fc region.

In one aspect, the invention provides an isolated polypeptide comprising a variant Fc region with a substantially decreased FcγR-binding activity and without a substantially decreased C1q-binding activity, compared to a polypeptide comprising a parent Fc region. In further aspects, the polypeptide of the invention comprises at least one amino acid alteration of at least one position selected from the group consisting of: 234, 235, 236, 267, 268, 324, 326, 332, and 333, according to EU numbering.

In one aspect, the variant Fc region with a substantially decreased FcγR-binding activity and without a substantially decreased C1q-binding activity comprises Ala at position 234, Ala at position 235 and at least one amino acid alteration of at least one position selected from the group consisting of: 236, 267, 268, 324, 326, 332, and 333, according to EU numbering.

In one aspect, the variant Fc region with a substantially decreased FcγR-binding activity and without a substantially decreased C1q-binding activity comprises Ala at position 234, Ala at position 235 and further amino acid alterations of any one of the following (a)-(c): (a) positions 267, 268, and 324; (b) positions 236, 267, 268, 324, and 332; and (c) positions 326 and 333, according to EU numbering.

In a further aspect, the variant Fc region with a substantially decreased FcγR-binding activity and without a substantially decreased C1q-binding activity comprises amino acids selected from the group consisting of: (a) Glu at position 267; (b) Phe at position 268; (c) Thr at position 324; (d) Ala at position 236; (e) Glu at position 332; (f) Ala, Asp, Glu, Met, or Trp at position 326; and (g) Ser at position 333, according to EU numbering.

In one aspect, the variant Fc region with a substantially decreased FcγR-binding activity and without a substantially decreased C1q-binding activity comprises amino acids of: Ala at position 234, Ala at position 235, Ala at position 326, and Ser at position 333, according to EU numbering. In one aspect, the variant Fc region with a substantially decreased FcγR-binding activity and without a substantially decreased C1q-binding activity comprises amino acids of: Ala at position 234, Ala at position 235, Asp at position 326, and Ser at position 333, according to EU numbering. In one aspect, the variant Fc region with a substantially decreased FcγR-binding activity and without a substantially decreased C1q-binding activity comprises amino acids of: Ala at position 234, Ala at position 235, Glu at position 326, and Ser at position 333, according to EU numbering. In one aspect, the variant Fc region with a substantially decreased FcγR-binding activity and without a substantially decreased C1q-binding activity comprises amino acids of: Ala at position 234, Ala at position 235, Met at position 326, and Ser at position 333, according to EU numbering. In one aspect, the variant Fc region with a substantially decreased FcγR-binding activity and without a substantially decreased C1q-binding activity comprises amino acids of: Ala at position 234, Ala at position 235, Trp at position 326, and Ser at position 333, according to EU numbering.

In another aspect, the variant Fc region of the invention can further comprise at least one amino acid alteration of at least one position selected from the group consisting of: 428, 434, 436, 438, and 440, according to EU numbering.

In a further aspect, the variant Fc region can further comprise amino acids selected from the group consisting of: (a) Ala at position 434; (b) Ala at position 434, Thr at position 436, Arg at position 438, and Glu at position 440; (c) Leu at position 428, Ala at position 434, Thr at position 436, Arg at position 438, and Glu at position 440; and (d) Leu at position 428, Ala at position 434, Arg at position 438, and Glu at position 440, according to EU numbering (see also WO2016/125495 describing a relationship between amino acid alterations and FcRn-binding activity of a variant Fc region).

In another aspect, the variant Fc region of the invention comprises amino acids of: Ala at position 234, Ala at position 235, Ala at position 326, Ser at position 333, Leu at position 428, Ala at position 434, Thr at position 436, Arg at position 438, and Glu at position 440, according to EU numbering. In another aspect, the variant Fc region of the invention comprises amino acids of: Ala at position 234, Ala at position 235, Ala at position 326, Ser at position 333, Leu at position 428, Ala at position 434, Arg at position 438, and Glu at position 440, according to EU numbering.

In one aspect, it is preferable that a variant Fc region of the invention does not have a substantially increased FcRn binding activity, especially at pH7.4, compared to the parent Fc region.

"FcRn" is structurally similar to polypeptides of major histocompatibility complex (MHC) class I, and exhibits 22% to 29% sequence identity with MHC class I molecules. FcRn is expressed as a heterodimer consisting of a soluble β or light chain (β2 microglobulin) complexed with a transmembrane a or heavy chain. Like MHC, the α chain of FcRn contains three extracellular domains (α1, α2, and α3), and its short cytoplasmic domain tethers them to the cell surface. The α1 and α2 domains interact with the FcRn-binding domain of the antibody Fc region. The polynucleotide and amino acid sequences of human FcRn may be derived, for example, from the precursors shown in NM_004107.4 and NP_004098.1 (containing the signal sequence), respectively.

The amino acid sequence of human FcRn (α chain) is set forth in SEQ ID NO: 81; and the amino acid sequence of human β2 microglobulin is set forth in SEQ ID NO: 82.

In one aspect, it is preferable that a variant Fc region of the invention does not have a substantially increased FcRn binding activity, especially at pH7.4, that is less than 1000 fold, less than 500 fold, less than 200 fold, less than 100 fold, less than 90 fold, less than 80 fold, less than 70 fold, less than 60 fold, less than 50 fold, less than 40 fold, less than 30 fold, less than 20 fold, less than 10 fold, less than 5 fold, less than 3 fold, or less than 2 fold compared to the FcRn binding activity for the parent Fc region. In one aspect, a variant Fc region of the invention does not have a substantially increased FcRn binding activity, especially at pH7.4, which means that the ratio of [the difference in the RU values of sensorgrams that changed before and after interaction of FcRn with the variant Fc region]/[the difference in the RU values of sensorgrams that changed before and after capturing FcRn to the sensor chips] is less than 0.5, less than 0.3, less than 0.2, less than 0.1, less than 0.08, less than 0.05, less than 0.03, less than 0.02, less than 0.01, less than 0.008, less than 0.005, less than 0.003, less than 0.002, or less than 0.001.

In another aspect, the variant Fc region of the invention comprises any of the amino acid alterations, singly or in combination, described in Table 4. In another aspect, the variant Fc region of the invention comprises at least any one of the amino acid alterations described in Table 4. In another aspect, the invention provides a polypeptide comprising the amino acid sequence of any one of SEQ ID NOs: 51-59.

In some embodiments, a polypeptide comprising a variant Fc region of the present invention is an antibody heavy chain constant region. In some embodiments, a polypeptide comprising a variant Fc region of the present invention further comprises an antigen-binding domain. In a further embodiment, the polypeptide is an antibody heavy chain. In a further embodiment, the polypeptide is an antibody. In certain embodiments, an antibody is a chimeric antibody, or a humanized antibody. The origin of an antibody is not particularly limited, but examples include a human antibody, a mouse antibody, a rat antibody, and a rabbit antibody. In a further embodiment, the polypeptide is an Fc fusion protein.

Two or more polypeptides comprising a variant Fc region described herein can be included in one molecule, wherein two polypeptides comprising variant Fc regions are associated, much like in an antibody. The type of antibody is not limited, and IgA (IgA1, IgA2), IgD, IgE, IgG (IgG1, IgG2, IgG3, IgG4), and IgM, or such can be used.

In some embodiments, a polypeptide comprising a variant Fc region of the present invention is an antibody. In further embodiments, a polypeptide comprising a variant Fe region of the present invention is an anti-virus antibody.

In further embodiments, a polypeptide comprising a variant Fc region of the present invention comprises an antibody variable region comprising:
- (a) (i) HVR-H3 comprising the amino acid sequence of SEQ ID NO: 16, (ii) HVR-L3 comprising the amino acid sequence of SEQ ID NO: 27, and (iii) HVR-H2 comprising the amino acid sequence of SEQ ID NO: 13;
- (b) (i) HVR-H1 comprising the amino acid sequence of SEQ ID NO: 11, (ii) HVR-H2 comprising the amino acid sequence of SEQ ID NO: 13, and (iii) HVR-H3 comprising the amino acid sequence of SEQ ID NO: 16;
- (c) (i) HVR-H1 comprising the amino acid sequence of SEQ ID NO: 11, (ii) HVR-H2 comprising the amino acid sequence of SEQ ID NO: 13, (iii) HVR-H3 comprising the amino acid sequence of SEQ ID NO: 16, (iv) HVR-L1 comprising the amino acid sequence of SEQ ID NO: 21; (v) HVR-L2 comprising the amino acid sequence of SEQ ID NO: 24; and (vi) HVR-L3 comprising the amino acid sequence of SEQ ID NO: 27; or
- (d) (i) HVR-L1 comprising the amino acid sequence of SEQ ID NO: 21; (ii) HVR-L2 comprising the amino acid sequence of SEQ ID NO: 24; and (iii) HVR-L3 comprising the amino acid sequence of SEQ ID NO: 27.

In further embodiments, a polypeptide comprising a variant Fc region of the present invention comprises an antibody variable region comprising:
- (a) (i) HVR-H3 from the VH sequence of SEQ ID NO: 6, (ii) HVR-L3 from the VL sequence of SEQ ID NO: 10, and (iii) HVR-H2 from the VH sequence of SEQ ID NO: 6;
- (b) (i) HVR-H1 from the VH sequence of SEQ ID NO: 6, (ii) HVR-H2 from the VH sequence of SEQ ID NO: 6, and (iii) HVR-H3 from the VH sequence of SEQ ID NO: 6;
- (c) (i) HVR-H1 from the VH sequence of SEQ ID NO: 6, (ii) HVR-H2 from the VH sequence of SEQ ID NO: 6, (iii) HVR-H3 from the VH sequence of SEQ ID NO: 6, (iv) HVR-L1 from the VL sequence of SEQ ID NO: 10;
(v) HVR-L2 from the VL sequence of SEQ ID NO: 10;
and (vi) HVR-L3 from the VL sequence of SEQ ID NO: 10;
(d) (i) HVR-L1 from the VL sequence of SEQ ID NO: 10;
(ii) HVR-L2 from the VL sequence of SEQ ID NO: 10;
and (iii) HVR-L3 from the VL sequence of SEQ ID NO: 10; or
(e) (i) HVR-H1 from the VH sequence of SEQ ID NO: 6,
(ii) HVR-H2 from the VH sequence of SEQ ID NO: 6,
(iii) HVR-H3 from the VH sequence of SEQ ID NO: 6,
(iv) HVR-L1 from the VL sequence of SEQ ID NO: 7;
(v) HVR-L2 from the VL sequence of SEQ ID NO: 7;
and (vi) HVR-L3 from the VL sequence of SEQ ID NO: 7.

In further embodiments, a polypeptide comprising a variant Fc region of the present invention comprises VH region comprising the amino acid sequence of SEQ ID NO: 1 and VL region comprising the amino acid sequence of SEQ ID NO: 7. In further embodiments, the invention provides an antibody comprising VH region comprising the amino acid sequence of SEQ ID NO: 1 and a variant Fc region comprising the amino acid sequence of SEQ ID NO: 54 in the heavy chain, and VL region comprising the amino acid sequence of SEQ ID NO: 7 in the light chain. In further embodiments, the invention provides an antibody comprising VH region comprising the amino acid sequence of SEQ ID NO: 1 and a variant Fc region comprising the amino acid sequence of SEQ ID NO: 58 in the heavy chain, and VL region comprising the amino acid sequence of SEQ ID NO: 7 in the light chain. In further embodiments, the invention provides an antibody comprising VH region comprising the amino acid sequence of SEQ ID NO: 1 and a variant Fc region comprising the amino acid sequence of SEQ ID NO: 59 in the heavy chain, and VL region comprising the amino acid sequence of SEQ ID NO: 7 in the light chain.

The invention also provides an anti-DENV antibody described herein, further comprising a polypeptide comprising a variant Fc region of the present invention. In some embodiments, an anti-DENV antibody of the invention comprises VH region comprising the amino acid sequence of SEQ ID NO: 6 and a variant Fc region comprising the amino acid sequence of SEQ ID NO: 54 in the heavy chain, and VL region comprising the amino acid sequence of SEQ ID NO: 10 in the light chain. In some embodiments, an anti-DENV antibody of the invention comprises VH region comprising the amino acid sequence of SEQ ID NO: 6 and a variant Fc region comprising the amino acid sequence of SEQ ID NO: 58 in the heavy chain, and VL region comprising the amino acid sequence of SEQ ID NO: 10 in the light chain. In some embodiments, an anti-DENV antibody of the invention comprises VH region comprising the amino acid sequence of SEQ ID NO: 6 and a variant Fc region comprising the amino acid sequence of SEQ ID NO: 59 in the heavy chain, and VL region comprising the amino acid sequence of SEQ ID NO: 10 in the light chain. In some embodiments, an anti-DENV antibody of the invention comprises VH region comprising the amino acid sequence of SEQ ID NO: 6 and a variant Fc region comprising the amino acid sequence of SEQ ID NO: 59 in the heavy chain, and VL region comprising the amino acid sequence of SEQ ID NO: 7 in the light chain.

A "parent Fc region" as used herein refers to an Fc region prior to introduction of an amino acid alteration(s) described herein. Preferred examples of the parent Fc region include Fc regions derived from native antibodies. Antibodies include, for example, IgA (IgA1, IgA2), IgD, IgE, IgG (IgG1, IgG2, IgG3, IgG4), and IgM, or such. Antibodies may be derived from human or monkey (e.g., cynomolgus, rhesus macaque, marmoset, chimpanzee, or baboon). Native antibodies may also include naturally-occurring mutations. A plurality of allotype sequences of IgGs due to genetic polymorphism are described in "Sequences of proteins of immunological interest", NIH Publication No. 91-3242, and any of them may be used in the present invention. In particular, for human IgG1, the amino acid sequence at positions 356 to 358 (EU numbering) may be either DEL or EEM. Preferred examples of the parent Fc region include Fc regions derived from a heavy chain constant region of human IgG1 (SEQ ID NO: 83), human IgG2 (SEQ ID NO: 84), human IgG3 (SEQ ID NO: 85), and human IgG4 (SEQ ID NO: 86). Another preferred example of the parent Fc region is an Fc region derived from a heavy chain constant region SG1 (SEQ ID NO: 87). Another preferred example of the parent Fc region is an Fc region derived from a heavy chain constant region SG182 (SEQ ID NO: 46). Furthermore, the parent Fc region may be an Fc region produced by adding an amino acid alteration(s) other than the amino acid alteration(s) described herein to an Fc region derived from a native antibody.

In addition, amino acid alterations performed for other purpose(s) can be combined in a variant Fc region described herein. For example, amino acid substitutions that improve FcRn-binding activity (Hinton et al., *J. Immunol.* 176(1): 346-356 (2006); Dall'Acqua et al., *J. Biol. Chem.* 281(33): 23514-23524 (2006); Petkova et al., *Intl. Immunol.* 18(12): 1759-1769 (2006); Zalevsky et al., *Nat. Biotechnol.* 28(2): 157-159 (2010); WO 2006/019447; WO 2006/053301; and WO 2009/086320), and amino acid substitutions for improving antibody heterogeneity or stability (WO 2009/041613) may be added. Alternatively, polypeptides with the property of promoting antigen clearance, which are described in WO 2011/122011, WO 2012/132067, WO 2013/046704 or WO 2013/180201, polypeptides with the property of specific binding to a target tissue, which are described in WO 2013/180200, polypeptides with the property for repeated binding to a plurality of antigen molecules, which are described in WO 2009/125825, WO 2012/073992 or WO 2013/047752, can be combined with a variant Fc region described herein. Alternatively, with the objective of conferring binding ability to other antigens, the amino acid alterations disclosed in EP1752471 and EP1772465 may be combined in CH3 of a variant Fc region described herein. Alternatively, with the objective of increasing plasma retention, amino acid alterations that decrease the pI of the constant region (WO 2012/016227) may be combined in a variant Fc region described herein. Alternatively, with the objective of promoting uptake into cells, amino acid alterations that increase the pI of the constant region (WO 2014/145159) may be combined in a variant Fc region described herein. Alternatively, with the objective of promoting elimination of a target molecule from plasma, amino acid alterations that increase the pI of the constant region (WO2016/125495 and WO2016/098357) may be combined in a variant Fc region described herein.

Amino acid alterations of enhancing human FcRn-binding activity under acidic pH can also be combined in a variant Fc region described herein. Specifically, such alterations may include, for example, substitution of Leu for Met at position 428 and substitution of Ser for Asn at position 434, according to EU numbering (Nat Biotechnol, 2010, 28: 157-159); substitution of Ala for Asn at position 434 (Drug Metab Dispos, 2010 April; 38(4): 600-605); substitution of Tyr for Met at position 252, substitution of Thr for Ser at position 254 and substitution of Glu for Thr at position 256 (J Biol Chem, 2006, 281: 23514-23524); substitution of Gln for Thr at position 250 and substitution of Leu for Met at position 428 (J Immunol, 2006, 176(1): 346-356); substitution of His for Asn at position 434 (Clin Pharmacol Ther, 2011, 89(2): 283-290), and alterations described in WO2010/106180, WO2010/045193, WO2009/058492, WO2008/022152, WO2006/050166, WO2006/053301, WO2006/031370, WO2005/123780, WO2005/047327, WO2005/037867, WO2004/035752, WO2002/060919, or such. In another embodiment, such alterations may include, for example, at least one alteration selected from the group consisting of substitution of Leu for Met at position 428, substitution of Ala for Asn at position 434 and substitution of Thr for Tyr at position 436. Those alterations may further include substitution of Arg for Gln at position 438 and/or substitution of Glu for Ser at position 440 (WO2016/125495).

In the present invention, amino acid alteration means any of substitution, deletion, addition, insertion, and modification, or a combination thereof. In the present invention, amino acid alteration may be rephrased as amino acid mutation.

Amino acid alterations are produced by various methods known to those skilled in the art. Such methods include the site-directed mutagenesis method (Hashimoto-Gotoh et al., Gene 152:271-275 (1995); Zoller, Meth. Enzymol. 100:468-500 (1983); Kramer et al., Nucleic Acids Res. 12: 9441-9456 (1984)); Kramer and Fritz, Methods Enzymol. 154: 350-367 (1987); and Kunkel, Proc. Natl. Acad. Sci. USA 82:488-492 (1985)), the PCR mutation method, and the cassette mutation method, but are not limited thereto.

The number of amino acid alterations introduced into an Fc region is not limited. In certain embodiments, it can be 1, 2 or less, 3 or less, 4 or less, 5 or less, 6 or less, 8 or less, 10 or less, 12 or less, 14 or less, 16 or less, 18 or less, or 20 or less.

Furthermore, a polypeptide comprising a variant Fc region of the present invention may be chemically modified with various molecules such as polyethylene glycol (PEG) and cytotoxic substances. Methods for such chemical modification of a polypeptide are established in the art.

In some embodiments, a polypeptide comprising a variant Fc region of the present invention is an antibody or an Fc fusion protein comprising a domain(s) which can bind to any antigen. Examples of antigens that can be bound by such antibodies and Fc fusion proteins include, but are not limited to ligands (cytokines, chemokines, and such), receptors, cancer antigens, viral antigens, MHC antigens, differentiation antigens, immunoglobulins, and immune complexes partly containing immunoglobulins.

B. Recombinant Methods and Compositions

In one example, it is referred to a process for preparing an antibody as described herein, wherein the process comprising the steps of:
(a) combining a VH variant sequence as described herein with a human IgG1 CH sequence as described herein;
(b) combining a VL variant sequence as described herein, with a human CL sequence SK1;
(c) cloning each one of the combinations in an expression vector;
(d) expressing the resulting expression vectors in co-transfected cells (host cell); and
(e) purifying the resulting antibody from step (d). In certain examples, a host cell is CHO-DXB11, CHO-K1 or CHO-DG44. Such host cell may be a cell expressing taurine transporter, obtained by introducing DNA encoding taurine transporter (WO2007/119774). Vectors that can be used for the manufacture of such antibodies are known in the art. Generally, antibodies may be produced using recombinant methods and compositions, e.g., as described in U.S. Pat. No. 4,816,567. In one embodiment, isolated nucleic acid encoding an anti-DENV antibody described herein is provided. In another embodiment, isolated nucleic acid encoding a polypeptide comprising a variant Fc region or a parent Fc region described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an anti-DENV antibody is provided, wherein the method comprises culturing a host cell comprising a nucleic acid encoding the antibody, as provided above, under conditions suitable for expression of the antibody, and optionally recovering the antibody from the host cell (or host cell culture medium). In another embodiment, a method of making a polypeptide comprising a variant Fc region or a parent Fc region is provided, wherein the method comprises culturing a host cell comprising the nucleic acid(s) encoding a polypeptide such as, an antibody, Fc region, or variant Fc region, as provided above, under conditions suitable for expression of the polypeptide, and optionally recovering the polypeptide from the host cell (or host cell culture medium).

For recombinant production of an anti-DENV antibody, nucleic acid encoding an antibody, e.g., as described above, is isolated and inserted into one or more vectors for further cloning and/or expression in a host cell. For recombinant production of an Fc region, nucleic acid encoding an Fc region is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N J, 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals (usually non-human mammals) are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature* 256(5517):495-497 (1975). In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro.

The immunizing agent will typically include the antigenic protein or a fusion variant thereof. Generally either peripheral blood lymphocytes (PBLs) are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press (1986), pp. 59-103).

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, California USA, and SP-2 cells (and derivatives thereof, e.g., X63-Ag8-653) available from the American Type Culture Collection, Manassas, Virginia USA. Human myeloma and mouse-human heteromyeloma cell lines also have been described for the production of human monoclonal antibodies (Kozbor et al. *J. Immunol.* 133(6):3001-3005 (1984); Brodeur et al., *Monoclonal Antibody Production Techniques and Applications*, Marcel Dekker, Inc., New York, pp. 51-63 (1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). Such techniques and assays are known in the art. For example, binding affinity may be determined by the Scatchard analysis of Munson, *Anal. Biochem.* 107(1):220-239 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

An Fc region may be obtained by re-eluting the fraction adsorbed onto protein A column after partially digesting IgG1, IgG2, IgG3, IgG4 monoclonal antibodies or such using a protease such as pepsin. The protease is not particularly limited as long as it can digest a full-length antibody so that Fab and F(ab')2 will be produced in a restrictive manner by appropriately setting the enzyme reaction conditions such as pH, and examples include pepsin and papain.

Furthermore, the present invention provides a method for producing a polypeptide comprising a variant Fc region with a substantially decreased FcγR-binding activity and without a substantially decreased C1q-binding activity in comparison with a polypeptide comprising a parent Fc region, which comprises introducing at least one amino acid alteration to the parent Fc region. In some aspects, the produced polypeptide is an antibody. In certain embodiments, an antibody is a chimeric antibody, or a humanized antibody. In some aspects, the produced polypeptide is an Fc fusion protein.

In one aspect, at least one amino acid is altered in the above-mentioned method for producing a polypeptide comprising a variant Fc region with a substantially decreased FcγR-binding activity and without a substantially decreased C1q-binding activity, of at least one position selected from the group consisting of: 234, 235, 236, 267, 268, 324, 326, 332, and 333, according to EU numbering.

In another aspect, two amino acids are altered in the above-mentioned method for producing a polypeptide comprising a variant Fc region with a substantially decreased FcγR-binding activity and without a substantially decreased C1q-binding activity, at positions 234 and 235.

In another aspect, amino acids are altered in the above-mentioned method for producing a polypeptide comprising a variant Fc region with a substantially decreased FcγR-binding activity and without a substantially decreased C1q-binding activity, the alterations comprising: (a) two amino acid alterations at positions 234 and 235, and (b) at least one amino acid alteration of at least one position selected from the group consisting of: 236, 267, 268, 324, 326, 332, and 333, according to EU numbering.

In another aspect, amino acids are altered in the above-mentioned method for producing a polypeptide comprising a variant Fc region with a substantially decreased FcγR-binding activity and without a substantially decreased C1q-binding activity, the alterations comprising: (a) two amino acid alterations at positions 234 and 235, and (b) at least one amino acid alterations of any one of the following (i)-(iii): (i) positions 267, 268, and 324; (ii) positions 236, 267, 268, 324, and 332; and (iii) positions 326 and 333, according to EU numbering.

In a further aspect, an amino acid alteration in the above-mentioned method for producing a polypeptide comprising a variant Fc region with a substantially decreased FcγR-binding activity and without a substantially decreased C1q-binding activity, is selected at each position from the group consisting of: (a) Ala at position 234; (b) Ala at position 235; (c) Glu at position 267; (d) Phe at position 268; (e) Thr at position 324; (f) Ala at position 236; (g) Glu at position 332; (h) Ala, Asp, Glu, Met, Trp at position 326; and (i) Ser at position 333, according to EU numbering.

In a further aspect, amino acid alterations in the above-mentioned method for producing a polypeptide comprising a variant Fc region with a substantially decreased FcγR-binding activity and without a substantially decreased C1q-binding activity, are: Ala at position 234, Ala at position 235, Ala at position 326, and Ser at position 333; according to EU numbering. In a further aspect, amino acid alterations in the above-mentioned method for producing a polypeptide comprising a variant Fc region with a substantially decreased FcγR-binding activity and without a substantially decreased C1q-binding activity, are: Ala at position 234, Ala at position 235, Asp at position 326, and Ser at position 333; according to EU numbering. In a further aspect, amino acid alterations in the above-mentioned method for producing a polypeptide comprising a variant Fc region with a substantially decreased FcγR-binding activity, and without a substantially decreased C1q-binding activity, are: Ala at position 234, Ala at position 235, Glu at position 326, and Ser at position 333; according to EU numbering. In a further aspect, amino acid alterations in the above-mentioned method for producing a polypeptide comprising a variant Fc region with a substantially decreased FcγR-binding activity, and without a substantially decreased C1q-binding activity, are: Ala at position 234, Ala at position 235, Met at position 326, and Ser at position 333; according to EU numbering. In a further aspect, amino acid alterations in the above-mentioned method for producing a polypeptide comprising a variant Fc region with a substantially decreased FcγR-binding activity, and without a substantially decreased C1q-binding activity, are: Ala at position 234, Ala at position 235, Trp at position 326, and Ser at position 333; according to EU numbering.

In another aspect, at least one amino acid is further altered in the above-mentioned method, of at least one position selected from the group consisting of: 428, 434, 436, 438, and 440, according to EU numbering.

In a further aspect, an amino acid alteration in the above-mentioned method is further selected from the following (a)-(d): (a) Ala at position 434; (b) Ala at position 434, Thr at position 436, Arg at position 438, and Glu at position 440; (c) Leu at position 428, Ala at position 434, Thr at position 436, Arg at position 438, and Glu at position 440; and (d) Leu at position 428, Ala at position 434, Arg at position 438, and Glu at position 440, according to EU numbering (see also WO2016/125495 describing a relationship between amino acid alterations and FcRn-binding activity of a variant Fc region).

In a further aspect, amino acid alterations in the above-mentioned method are: Ala at position 234, Ala at position 235, Ala at position 326, Ser at position 333, Leu at position 428, Ala at position 434, Thr at position 436, Arg at position 438, and Glu at position 440, according to EU numbering. In a further aspect, amino acid alterations in the above-mentioned method are: Ala at position 234, Ala at position 235, Ala at position 326, Ser at position 333, Leu at position 428, Ala at position 434, Arg at position 438, and Glu at position 440, according to EU numbering.

In one aspect, it is preferable that a variant Fc region of the invention does not have a substantially increased FcRn binding activity, especially at pH7.4, compared to the parent Fc region.

In a further aspect, the amino acid alterations in the above-mentioned production methods are selected from any single alteration, combination of single alterations, or combination alterations described in Table 4.

Polypeptides comprising a variant Fc region produced by any of the above-mentioned methods or other methods know in the art are included in the present invention.

C. Assays

Anti-DENV antibodies provided herein may be identified, screened for, or characterized for their physical/chemical properties and/or biological activities by various assays known in the art.

Variant Fc regions provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc. In one aspect, a polypeptide comprising a variant Fc region of the invention is tested for its antigen binding activity, e.g., by known methods such as ELISA, Western blot, etc.

In another aspect, competition assays may be used to identify an antibody that competes for binding to DENV and/or DENV E protein with any anti-DENV antibody described herein. In certain embodiments, when such a competing antibody is present in excess, it blocks (e.g., reduces) the binding of a reference antibody to DENV and/or DENV E protein by at least 10%, 15%, 20%, 25%, 30%, 35%, 40%, 45%, 50%, 55%, 60%, 65%, 70%, 75% or more. In some instances, binding is inhibited by at least 80%, 85%, 90%, 95%, or more. In certain embodiments, such a competing antibody binds to the same epitope (e.g., a linear or a conformational epitope) that is bound by an anti-DENV antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized DENV or DENV E protein is incubated in a solution comprising a first labeled antibody that binds to DENV and/or DENV E protein and a second unlabeled antibody that is being tested for its ability to compete with the first antibody for binding to DENV or DENV E protein. The second antibody may be present in a hybridoma supernatant. As a control, immobilized DENV or DENV E protein is incubated in a solution comprising the first labeled antibody but not the second unlabeled antibody. After incubation under conditions permissive for binding of the first antibody to DENV or DENV E protein, excess unbound antibody is removed, and the amount of label associated with immobilized DENV or DENV E protein is measured. If the amount of label associated with immobilized DENV or DENV E protein is substantially reduced in the test sample relative to the control sample, then that indicates that the second antibody is competing with the first antibody for binding to DENV or DENV E protein. See Harlow and Lane (1988) *Antibodies: A Laboratory Manual* ch.14 (Cold Spring Harbor Laboratory, Cold Spring Harbor, NY).

Assays for determining the binding activity of a polypeptide containing a variant Fc region towards one or more FcR family members are described herein or otherwise known in the art. Such binding assays include but are not limited to BIACORE® analysis, which utilizes the surface plasmon resonance (SPR) phenomena, Amplified Luminescent Proximity Homogeneous Assay (ALPHA) screening, ELISA, and fluorescence activated cell sorting (FACS) (Lazar et al., *Proc. Natl. Acad. Sci. USA* (2006) 103(11): 4005-4010).

In one embodiment, BIACORE® analysis can be used to evaluate whether the binding activity of a polypeptide comprising a variant Fc region is enhanced, or maintained or decreased with respect to a particular FcR family member. For example, by observing whether there is a decrease or an increase in the dissociation constant (Kd) value obtained from sensorgram analysis, where various FcRs are subjected to interaction as an analyte with polypeptides comprising a variant Fc region immobilized or captured onto the sensor chip using known methods and reagents such as Protein A, Protein L, Protein A/G, Protein G, anti-lamda chain antibodies, anti-kappa chain antibodies, antigenic peptides, antigenic proteins). Alterations in binding activity can also be determined by comparing changes in the resonance unit (RU) value on the sensorgram before and after the one or more types of FcRs are subjected to interaction as analytes with the captured polypeptides comprising the variant Fc region. Alternatively, FcR can be immobilized or captured onto the sensor chips, and the polypeptides comprising the variant Fc region are used as an analyte.

In BIACORE® analysis, one of the substances (the ligand) in observation of an interaction is immobilized onto a gold thin film on a sensor chip, and by shining light from the reverse side of the sensor chip so that total reflection takes place at the interface between the gold thin film and glass, a portion of reduced reflection intensity is formed in part of the reflected light (SPR signal). When the other one of the substances (the analyte) in observation of an interaction is made to flow on the sensor chip surface and the ligand binds to the analyte, the mass of the immobilized ligand molecule increases and the refractive index of the solvent on the sensor chip surface changes. The position of the SPR signal shifts as a result of this change in refractive index (on the other hand, the signal position returns when this binding dissociates). The BIACORE® system indicates the amount of shift mentioned above, or more specifically the time variable of mass by plotting the change in mass on the sensor chip surface on the ordinate as the measurement data (sensorgram). The amount of analyte bound to the ligand trapped on the sensor chip surface is determined from the sensorgram. Kinetic parameters such as association rate constants (ka) and dissociation rate constants (kd) are determined from the curves of the sensorgram, and the dissociation constants (Kd) are determined from the ratio of these constants. In the BIACORE® method, a method for measuring inhibition is preferably used. An example of the method for measuring inhibition is described in Lazar et al., *Proc. Natl. Acad. Sci. USA* 103(11):4005-4010 (2006).

ALPHA screening is performed by ALPHA technology which uses two beads, a donor and an acceptor, based on the following principles. Luminescent signals are detected only when molecules bound to donor beads physically interact with molecules bound to the acceptor beads, and the two beads are in close proximity to each other. Laser-excited photosensitizer in the donor beads converts ambient oxygen to excited-state singlet oxygen. Singlet oxygen is dispersed around the donor beads, and when it reaches the adjacent acceptor beads, chemiluminescent reaction is induced in the beads, and light is ultimately emitted. When the molecules bound to the donor beads do not interact with the molecules bound to the acceptor beads, the chemiluminescent reaction does not take place because singlet oxygen produced by the donor beads does not reach the acceptor beads.

For example, a biotinylated polypeptide complex is bound to the donor beads, and Fc receptor tagged with glutathione S transferase (GST) is linked to the acceptor beads. In the absence of a competing polypeptide complex comprising a variant Fc region, the polypeptide complex comprising a parent Fc region interacts with the Fc receptor and produces 520-620 nm signals. The polypeptide complex comprising an untagged variant Fc region competes with the polypeptide complex comprising a parent Fc region for interaction with the Fc receptor. Relative binding activities can be determined by quantifying the decrease in fluorescence observed as a result of the competition. Biotinylation of polypeptide complexes such as antibodies using Sulfo-NHS-biotin and such is well known. The method of expressing the Fc receptor and GST in a cell carrying a fusion gene produced by fusing a polynucleotide encoding the Fc receptor in frame with a polynucleotide encoding GST in an expressible vector, and performing purification using a glutathione column is appropriately adopted as a method for tagging an Fc receptor with GST. The obtained signals are preferably analyzed, for example, by fitting them to a one-site competition model which uses a non-linear regression analysis using software such as GRAPHPAD PRISM (GraphPad, San Diego).

A variant Fc region with decreased FcR-binding activity refers to an Fc region which binds to FcR with essentially weaker binding activity than a parent Fc region when assays are performed using substantially the same amount of a corresponding parent Fc region and a variant Fc region. Furthermore, a variant Fc region with increased FcR-binding activity refers to an Fc region which binds to FcR with essentially stronger binding activity than a corresponding parent Fc region when assays are performed using substantially the same amount of a parent Fc region and a variant Fc region. A variant Fc region with maintained FcR-binding activity refers to an Fc region that binds to FcR with binding activity equivalent to or essentially not different from that of a parent Fc region when assays are performed using substantially the same amount of the corresponding parent Fc region and the polypeptide containing the variant Fc region.

Whether the binding activities of an Fc region towards various FcRs were increased or decreased can be determined from the increase or decrease in the amount of binding of the various FcRs to the Fc region, which were determined according to the above-mentioned measurement method. Here, the amount of binding of the various FcRs to the Fc region can be evaluated as a value obtained by dividing the difference in the RU values of sensorgrams that changed before and after interaction of various FcRs as the analyte with the Fc region, by the difference in the RU values of sensorgrams that changed before and after capturing the Fc regions to the sensor chips. The binding activity of an Fc region for an FcγR or an FcRn can be determined by a method described in Example 5 herein.

In the present invention, a substantially decreased FcγR-binding activity preferably means, for example, that the binding activity of a variant Fc region for an FcγR is less than 50%, less than 45%, less than 40%, less than 35%, less than 30%, less than 25%, less than 20%, less than 15%, less than 10%, less than 5%, less than 2%, less than 1%, less than 0.5%, less than 0.2%, or less than 0.1% as a function of the FcγR-binding activity for the parent Fc region. It also preferably means, for example, that the ratio of [the difference in the RU values of sensorgrams that changed before and after interaction of FcγR with the variant Fc region]/[the difference in the RU values of sensorgrams that changed before and after capturing FcγR to the sensor chips] is less than 1, less than 0.8, less than 0.5, less than 0.3, less than 0.2, less than 0.1, less than 0.08, less than 0.05, less than 0.03, less than 0.02, less than 0.01, less than 0.008, less than 0.005, less than 0.003, less than 0.002, or less than 0.001.

In the present invention, not a substantially increased FcRn-binding activity, especially at pH7.4, preferably means, for example, that the binding activity of a variant Fc region for an FcRn is less than 1000 fold, less than 500 fold, less than 200 fold, less than 100 fold, less than 90 fold, less than 80 fold, less than 70 fold, less than 60 fold, less than 50 fold, less than 40 fold, less than 30 fold, less than 20 fold, less than 10 fold, less than 5 fold, less than 3 fold, or less than 2 fold compared to the FcRn-binding activity of the parent Fc region. It also preferably means, for example, that the ratio of [the difference in the RU values of sensorgrams that changed before and after interaction of FcRn with the variant Fc region]/[the difference in the RU values of sensorgrams that changed before and after capturing FcRn to the sensor chips] is less than 0.5, less than 0.3, less than 0.2, less than 0.1, less than 0.08, less than 0.05, less than 0.03, less than 0.02, less than 0.01, less than 0.008, less than 0.005, less than 0.003, less than 0.002, or less than 0.001.

To determine the binding activity of a polypeptide containing a variant Fc region towards C1q, a C1q binding ELISA may be performed. Briefly, assay plates may be coated overnight at 4° C. with a polypeptide containing a variant Fc region or a polypeptide containing a parent Fc region (control) in coating buffer. The plates may then be washed and blocked. Following washing, an aliquot of human C1q may be added to each well and incubated for 2 hours at room temperature. Following a further wash, 100 μl of a sheep anti-complement C1q peroxidase conjugated antibody may be added to each well and incubated for 1 hour at room temperature. The plate may again be washed with wash buffer and 100 μl of substrate buffer containing OPD (o-phenylenediamine dihydrochloride (Sigma)) may be added to each well. The oxidation reaction, observed by the appearance of a yellow color, may be allowed to proceed for 30 minutes and stopped by the addition of 100 μl of 4.5 N $H_2SO_4$. The absorbance may then read at (492-405) nm. The binding of an Fc region for C1q can be determined by a method described in Example 4 herein.

In one aspect, the difference of C1q binding activities between a variant Fc region and a parent Fc region of the invention is less than 50%, less than 45%, less than 40%, less than 35%, less than 30%, less than 25%, less than 20%, less than 15%, less than 10%, or less than 5% as a function of the C1q-binding activity for the parent Fc region.

2. Activity Assays

In one aspect, assays are provided for identifying anti-DENV antibodies having biological activity. Biological activity may include, e.g., blocking binding of DENV E protein to a host cell, inhibiting DENV entry into a host cell, inhibiting and/or preventing DENV infection of a host cell, etc. Antibodies having such biological activity in vivo and/or in vitro are also provided.

In certain embodiments, an antibody of the invention is tested for such biological activity. In certain embodiments, plaque reduction neutralization test (PRNT) assay may be utilized for measuring activity or neutralizing potency of a test antibody. In some embodiments, animal host may be used for measuring anti-DENV activity in vivo.

In certain embodiments, cells may be directly assayed for binding between DENV and a test antibody. Immunohistochemical techniques, confocal techniques, and/or other techniques to assess binding are well known to those of skill in the art. Various cell lines may be utilized for such screening assays, including cells specifically engineered for this purpose. Examples of cells used in the screening assays include mammalian cells, fungal cells, bacterial cells, or viral cells. A cell may be a stimulated cell, such as a cell stimulated with a growth factor. One of skill in the art would understand that the invention disclosed herein contemplates a wide variety of assays for measuring the ability of a test antibody to bind to DENV.

Depending on the assay, cell and/or tissue culture may be required. A cell may be examined using any of a number of different physiologic assays. Alternatively or additionally, molecular analysis may be performed, including, but not limited to, western blotting to monitor protein expression and/or test for protein-protein interactions; mass spectrometry to monitor other chemical modifications; etc.

In some embodiments, such methods utilize an animal host. For example, animal hosts suitable for the invention can be any mammalian hosts, including primates, ferrets, cats, dogs, cows, horses, and rodents such as mice, hamsters, rabbits, and rats. In some embodiments, the animal host is inoculated with, infected with, or otherwise exposed to virus prior to or concurrent with administration of a test antibody. Naive and/or inoculated animals may be used for any of a variety of studies. For example, such animal models may be used for virus transmission studies as is known in the art. A test antibody may be administered to a suitable animal host before, during or after virus transmission studies in order to determine the efficacy of the test antibody in blocking virus binding and/or infectivity in the animal host.

In one aspect, assays are provided for identifying polypeptides comprising variant Fc regions having biological activity. Biological activity may include, e.g., ADCC activity and CDC activity. Polypeptides comprising variant Fc regions having such biological activity in vivo and/or in vitro are also provided.

In certain embodiments, a polypeptide comprising a variant Fc region of the invention is tested for such biological activity. In a certain aspects, a polypeptide comprising a variant Fc region of the invention modulate an effector function as compared to the polypeptide comprising a parent Fc region. In a certain aspect, this modulation is a modulation of ADCC and/or CDC.

In vitro and/or in vivo cytotoxicity assays can be conducted to confirm the CDC and/or ADCC activities. For example, Fc receptor (FcR) binding assays can be conducted to ensure that the antibody has FcγR binding (hence likely having ADCC activity), and retains FcRn binding ability. The primary cells for mediating ADCC, NK cells express FcγRIII only, whereas monocytes express FcγRI, FcγRII and FcγRIII. FcR expression on hematopoietic cells is summarized in Table 3 on page 464 of Ravetch and Kinet, Annu Rev Immunol (1991) 9, 457-492. Non-limiting examples of in vitro assays to assess ADCC activity of a molecule of interest is described in U.S. Pat. No. 5,500,362 (see, e.g. Hellstrom et al, Proc Natl Acad Sci USA (1986) 83, 7059-7063) and Hellstrom et al, Proc Natl Acad Sci USA (1985) 82, 1499-1502; U.S. Pat. No. 5,821,337 (see Bruggemann et al, J Exp Med (1987) 166, 1351-1361). Alternatively, non-radioactive assay methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al, Proc Natl Acad Sci USA (1998) 95, 652-656. C1q binding assays may also be carried out to confirm whether the antibody binds C1q and hence has CDC activity. See, e.g., C1q and C3c binding ELISA in WO 2006/029879 and WO 2005/100402. To assess complement activation, a CDC assay may be performed (see, for example, Gazzano-Santoro et al, J Immunol Methods (1997) 202, 163-171; Cragg et al, Blood (2003) 101, 1045-1052; and Cragg and Glennie, Blood (2004) 103, 2738-2743). FcRn binding and in vivo clearance/half life determinations can also be performed using methods known in the art (see, e.g., Petkova et al, Int Immunol (2006) 18, 1759-1769).

D. Immunoconjugates

In some embodiments, the invention also provides immunoconjugates comprising an anti-DENV antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes. In some embodiments, the invention also provides immunoconjugates comprising a polypeptide comprising a variant Fc region herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example Tc-99m or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

E. Methods and Compositions for Diagnostics and Detection

In certain embodiments, any of the anti-DENV antibodies provided herein is useful for detecting the presence of DENV and/or DENV E protein in a biological sample. The term "detecting" as used herein encompasses quantitative or qualitative detection. In certain embodiments, a biological sample comprises a cell or tissue, such as serum, whole blood, plasma, biopsy sample, tissue sample, cell suspension, saliva, sputum, oral fluid, cerebrospinal fluid, amniotic fluid, ascites fluid, milk, colostrum, mammary gland secretion, lymph, urine, sweat, lacrimal fluid, gastric fluid, synovial fluid, peritoneal fluid, ocular lens fluid or mucus.

In one embodiment, an anti-DENV antibody for use in a method of diagnosis or detection is provided. In a further aspect, a method of detecting the presence of DENV in a biological sample is provided. In certain embodiments, the method comprises contacting the biological sample with an anti-DENV antibody as described herein under conditions permissive for binding of the anti-DENV antibody to DENV, and detecting whether a complex is formed between the anti-DENV antibody and DENV. Such method may be an in vitro or in vivo method. In a further aspect, a method of detecting the presence of DENV E protein in a biological sample is provided. In certain embodiments, the method comprises contacting the biological sample with an anti-DENV antibody as described herein under conditions permissive for binding of the anti-DENV antibody to DENV E protein, and detecting whether a complex is formed between the anti-DENV antibody and DENV E protein. Such method may be an in vitro or in vivo method. In one embodiment, an anti-DENV antibody is used to select subjects eligible for therapy with an anti-DENV antibody, e.g. where DENV or DENV E protein is a biomarker for selection of patients.

Exemplary disorders that may be diagnosed using an antibody of the invention include DENV infection and diseases and/or symptoms caused by or associated with DENV infection such as dengue fever, dengue hemorrhagic fever (DHF), and dengue shock syndrome (DSS).

In certain embodiments, labeled anti-DENV antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, those coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In one embodiment, an antibody comprising a variant Fc region of the invention may be used as an affinity purification agent. In this process, the antibody variant is immobilized on a solid phase such a Sephadex resin or filter paper, using methods well known in the art. The immobilized antibody variant is contacted with a sample containing the antigen to be purified, and thereafter the support is washed with a suitable solvent that will remove substantially all the material in the sample except the antigen to be purified, which is bound to the immobilized antibody variant. Finally, the support is washed with another suitable solvent, such as glycine buffer, pH 5.0, that will release the antigen from the antibody variant.

The antibody variant may also be useful in diagnostic assays, e.g., for detecting expression of an antigen of interest in specific cells, tissues, or serum.

The antibody variant may be employed in any known assay method, such as competitive binding assays, direct and indirect sandwich assays, and immunoprecipitation assays. Zola, Monoclonal Antibodies: A Manual of Techniques, (1987) pp. 147-158, CRC Press, Inc.

F. Pharmaceutical Formulations

Pharmaceutical formulations of an anti-DENV antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions.

Pharmaceutical formulations of a polypeptide comprising a variant Fc region as described herein are prepared by mixing such polypeptide having the desired degree of purity with one or more optional pharmaceutically acceptable carriers in the form of lyophilized formulations or aqueous solutions.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an antiviral agent, such as, but not limited to, interferons (e.g., interferon α-2b, interferon-γ, etc.), anti-DENV monoclonal antibodies, anti-DENV polyclonal antibodies, RNA polymerase inhibitors, protease inhibitors, helicase inhibitors, immunomodulators, antisense compounds, short interfering RNAs, short hairpin RNAs, micro RNAs, RNA aptamers, ribozymes, and combinations thereof. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-DENV antibodies provided herein may be used in therapeutic methods.

In one aspect, an anti-DENV antibody for use as a medicament is provided. In further aspects, an anti-DENV antibody for use in treating DENV infection is provided. In certain embodiments, an anti-DENV antibody for use in a method of treatment is provided. In certain embodiments, the invention provides an anti-DENV antibody for use in a method of treating an individual having DENV infection comprising administering to the individual an effective amount of the anti-DENV antibody. In one such embodiment, the method further comprises administering to the individual an effective amount of at least one additional therapeutic agent, e.g., as described below. In further embodiments, the invention provides an anti-DENV antibody for use in blocking binding of DENV E protein to and/or DENV entry into a host cell. In certain embodiments, the invention provides an anti-DENV antibody for use in a method of blocking binding of DENV E protein to and/or DENV entry into a host cell in an individual comprising administering to the individual an effective of the anti-DENV antibody to block binding of DENV E protein to and/or DENV entry into a host cell. An "individual" according to any of the above embodiments is preferably a human.

In a further aspect, the invention provides for the use of an anti-DENV antibody in the manufacture or preparation of a medicament. In one embodiment, the medicament is for treatment of DENV infection. In a further embodiment, the medicament is for use in a method of treating DENV infection comprising administering to an individual having DENV infection an effective amount of the medicament. In one such embodiment, the method further comprises administering to the individual an effective amount of at least one additional therapeutic agent, e.g., as described below. In a further embodiment, the medicament is for blocking binding of DENV E protein to and/or DENV entry into a host cell. In a further embodiment, the medicament is for use in a method of blocking binding of DENV E protein to and/or DENV entry into a host cell in an individual comprising administering to the individual an amount effective of the medicament to block binding of DENV E protein to and/or DENV entry into a host cell. An "individual" according to any of the above embodiments may be a human.

In a further aspect, the invention provides a method for treating a DENV infection. In one embodiment, the method comprises administering to an individual having such DENV infection an effective amount of an anti-DENV antibody. In one such embodiment, the method further comprises administering to the individual an effective amount of at least one additional therapeutic agent, as described below. An "individual" according to any of the above embodiments may be a human.

In a further aspect, the invention provides a method for blocking binding of DENV E protein to and/or DENV entry into a host cell in an individual. In one embodiment, the method comprises administering to the individual an effective amount of an anti-DENV antibody to block binding of DENV E protein to and/or DENV entry into a host cell. In one embodiment, an "individual" is a human.

In a further aspect, the invention provides pharmaceutical formulations comprising any of the anti-DENV antibodies provided herein, e.g., for use in any of the above therapeutic methods. In one embodiment, a pharmaceutical formulation comprises any of the anti-DENV antibodies provided herein and a pharmaceutically acceptable carrier. In another embodiment, a pharmaceutical formulation comprises any of the anti-DENV antibodies provided herein and at least one additional therapeutic agent, e.g., as described below.

In a further aspect, the pharmaceutical formulation is for treatment of DENV infection. In a further embodiment, the pharmaceutical formulation is for blocking binding of DENV E protein to and/or DENV entry into a host cell. In one embodiment, the pharmaceutical formulation is administered to an individual having DENV infection. An "individual" according to any of the above embodiments is preferably a human.

In certain embodiments, DENV infection may include diseases and/or symptoms caused by or associated with DENV infection such as dengue fever, dengue hemorrhagic fever (DHF), and dengue shock syndrome (DSS).

Any of the polypeptides comprising a variant Fc region provided herein may be used in therapeutic methods.

In one aspect, a polypeptide comprising a variant Fc region for use as a medicament is provided. In certain embodiments, a polypeptide comprising a variant Fc region for use in a method of treatment is provided. In certain embodiments, the invention provides a polypeptide comprising a variant Fc region for use in a method of treating an individual having a disorder comprising administering to the individual an effective amount of the polypeptide comprising a variant Fc region. In one such embodiment, the method further comprises administering to the individual an effective amount of at least one additional therapeutic agent. In one embodiment, the disorder is a viral infection. In one embodiment, the "individual" is a human.

In a further aspect, the invention provides for the use of a polypeptide comprising a variant Fc region in the manufacture or preparation of a medicament. In one embodiment, the medicament is for treatment of a disorder. In some aspects, the polypeptide is an antibody. In some aspects, the polypeptide is an Fc fusion protein. In a further embodiment, the medicament is for use in a method of treating a disorder comprising administering to an individual having the disorder to be treated an effective amount of the medicament. In one such embodiment, the method further comprises administering to the individual an effective amount of at least one additional therapeutic agent. In one embodiment, the disorder is a viral infection. In one embodiment, the "individual" is a human.

In a further aspect, the invention provides a method for treating a disorder. In one embodiment, the method comprises administering to an individual having such a disorder an effective amount of a polypeptide comprising a variant Fc region. In one such embodiment, the method further comprises administering to the individual an effective amount of at least one additional therapeutic agent. In one embodiment, the disorder is a viral infection. In one embodiment, the "individual" is a human.

In a further aspect, the invention provides pharmaceutical formulations comprising a polypeptide comprising a variant Fc region provided herein, for use in a therapeutic method such as any of the therapeutic methods described herein. In one embodiment, a pharmaceutical formulation comprises a polypeptide comprising a variant Fc region provided herein and a pharmaceutically acceptable carrier. In another embodiment, a pharmaceutical formulation comprises a polypeptide comprising a variant Fc region provided herein and at least one additional therapeutic agent.

In a further aspect, the pharmaceutical formulation is for treatment of a disorder. In one embodiment, the pharmaceutical formulation is administered to an individual having a disorder. In one embodiment, the disorder is a viral infection. In one embodiment, the "individual" is a human.

Anti-virus antibodies that comprise a variant Fc region of the present invention can suppress antibody-dependent enhancement (ADE) observed with conventional anti-virus antibodies. ADE is a phenomenon where a virus bound to an antibody is phagocytosed via activating FcγRs so that infection of the virus to a cell is enhanced. Fc modifications that reduce interaction with activating FcγRs could alleviate the risk of ADE. Mutations at positions 234 and 235 from leucine to alanine to form LALA mutants have been shown to reduce the risk of ADE of dengue infection in vivo (Cell Host Microbe (2010) 8, 271-283). Such modifications, however, reduce the other effector immune functions mediated by antibodies, such as ADCC and CDC. Especially, CDC can be expected to play an important role in inhibiting ADE, therefore complement component C1q binding of Fc regions should not be reduced for therapeutic efficacy. Furthermore, antibody half-life can be extended by engineering Fc regions that change binding affinity to its salvage receptor, FcRn, which might lead to prophylactic use of antibodies for protecting viral infection.

The virus is preferably selected from an adenovirus, an astrovirus, a hepadnavirus, a herpesvirus, a papovavirus, a poxvirus, an arenavirus, a bunyavirus, a calcivirus, a coronavirus, a filovirus, a flavivirus, an orthomyxovirus, a paramyxovirus, a picornavirus, a reovirus, a retrovirus, a rhabdovirus, or a togavirus.

In preferred embodiments, the adenovirus includes, but is not limited to, a human adenovirus. In preferred embodiments, the astrovirus includes, but is not limited to, a mamastrovirus. In preferred embodiments, the hepadnavirus includes, but is not limited to, the hepatitis B virus. In preferred embodiments, the herpesvirus includes, but is not limited to, a herpes simplex virus type I, a herpes simplex virus type 2, a human cytomegalovirus, an Epstein-Barr virus, a varicella zoster virus, a roseolovirus, and a Kaposi's sarcoma-associated herpesvirus. In preferred embodiments, the papovavirus includes, but is not limited to, human papilloma virus and a human polyoma virus. In preferred embodiments, the poxvirus includes, but is not limited to, a variola virus, a vaccinia virus, a cowpox virus, a monkeypox virus, a smallpox virus, a pseudocowpox virus, a papular stomatitis virus, a tanapox virus, a yaba monkey tumor virus, and a molluscum contagiosum virus. In preferred embodiments, the arenavirus includes, but is not limited to lymphocytic choriomeningitis virus, a lassa virus, a machupo virus, and a junin virus. In preferred embodiments, the bunyavirus includes, but is not limited to, a hanta virus, a nairovirus, an orthobunyavirus, and a phlebovirus. In preferred embodiments, the calcivirus includes, but is not limited to, a vesivirus, a norovirus, such as the Norwalk virus and a sapovirus. In preferred embodiments, the coronavirus includes, but is not limited to, a human coronavirus (etiologic agent of severe acute respiratory syndrome (SARS)). In preferred embodiments, the filovirus includes, but is not limited to, an Ebola virus and a Marburg virus. In preferred embodiments, the flavivirus includes, but is not limited to, a yellow fever virus, a West Nile virus, a dengue virus (DENV-1, DENV-2, DENV-3 and DENV-4), a hepatitis C virus, a tick borne encephalitis virus, a Japanese encephalitis virus, a Murray Valley encephalitis virus, a St. Louis encephalitis virus, a Russian spring-summer encephalitis virus, a Omsk hemorrhagic fever virus, a bovine viral diarrhea virus, a Kyasanus Forest disease virus, and a Powassan encephalitis virus. In preferred embodiments, the orthomyxovirus includes, but is not limited to, influenza virus type A, influenza virus type B, and influenza virus type C. In preferred embodiments, the paramyxovirus includes, but is not limited to, a parainfluenza virus, a rubula virus (mumps), a morbillivirus (measles), a pneumovirus, such as a human respiratory syncytial virus, and a subacute sclerosing panencephalitis virus. In preferred embodiments, the picornavirus includes, but is not limited to, a poliovirus, a rhinovirus, a coxsackievirus A, a coxsackievirus B, a hepatitis A virus, an echovirus, and an eneterovirus. In preferred embodiments, the reovirus includes, but is not limited to, a Colorado tick fever virus and a rotavirus. In preferred embodiments, the retrovirus includes, but is not limited to, a lentivirus, such as a human immunodeficiency virus, and a human T-lymphotrophic virus (HTLV). In preferred embodiments, the rhabdovirus includes, but is not limited to, a lyssavirus, such as the rabies virus, the vesicular stomatitis virus and the infectious hematopoietic necrosis virus. In preferred embodiments, the togavirus includes, but is not limited to, an alphavirus, such as a Ross river virus, an O'nyong'nyong virus, a Sindbis virus, a Venezuelan equine encephalitis virus, an Eastern equine encephalitis virus, and a Western equine encephalitis virus, and a rubella virus.

In a further aspect, the invention provides methods for preparing a medicament or a pharmaceutical formulation, comprising mixing any of the anti-DENV antibodies provided herein with a pharmaceutically acceptable carrier, e.g., for use in any of the above therapeutic methods. In one embodiment, the methods for preparing a medicament or a pharmaceutical formulation further comprise adding at least one additional therapeutic agent to the medicament or pharmaceutical formulation.

Antibodies of the invention can be used either alone or in combination with other agents in a therapy. For instance, an antibody of the invention may be co-administered with at least one additional therapeutic agent. In certain embodiments, an additional therapeutic agent is an antiviral agent, such as, but not limited to, interferons (e.g., interferon α-2b, interferon-γ, etc.), anti-DENV monoclonal antibodies, anti-DENV polyclonal antibodies, RNA polymerase inhibitors, protease inhibitors, helicase inhibitors, immunomodulators, antisense compounds, short interfering RNAs, short hairpin RNAs, micro RNAs, RNA aptamers, ribozymes, and combinations thereof.

In a further aspect, the invention provides methods for preparing a medicament or a pharmaceutical formulation, comprising mixing any of the polypeptides comprising a variant Fc region provided herein with a pharmaceutically acceptable carrier, e.g., for use in any of the above therapeutic methods. In one embodiment, the methods for preparing a medicament or a pharmaceutical formulation further comprise adding at least one additional therapeutic agent to the medicament or pharmaceutical formulation.

Polypeptides comprising a variant Fc region of the invention can be used either alone or in combination with other agents in a therapy. For instance, a polypeptide comprising a variant Fc region of the invention may be co-administered with at least one additional therapeutic agent. In certain embodiments, an additional therapeutic agent is an antiviral agent, such as, but not limited to, interferons (e.g., interferon α-2b, interferon-γ, etc.), anti-virus monoclonal antibodies, anti-virus polyclonal antibodies, RNA polymerase inhibitors, protease inhibitors, helicase inhibitors, immunomodulators, antisense compounds, short interfering RNAs, short hairpin RNAs, micro RNAs, RNA aptamers, ribozymes, and combinations thereof.

Such combination therapies noted above encompass combined administration (where two or more therapeutic agents are included in the same or separate formulations), and separate administration, in which case, administration of the antibody or polypeptide comprising a variant Fc region of the invention can occur prior to, simultaneously, and/or following, administration of the additional therapeutic agent or agents. In one embodiment, administration of the anti-DENV antibody and administration of an additional therapeutic agent occur within about one month, or within about one, two or three weeks, or within about one, two, three, four, five, or six days, of each other. In another embodiment, the administration of the polypeptide comprising the variant Fc region and the administration of an additional therapeutic agent occur within about one month, or within about one, two or three weeks, or within about one, two, three, four, five, or six days, of each other.

An antibody or a polypeptide comprising a variant Fc region of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies or polypeptides comprising a variant Fc region of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The agent need not be, but is optionally formulated with one or more agents currently used to prevent or treat the disorder in question. The effective amount of such other agents depends on the amount of agent present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or a polypeptide comprising a variant Fc region of the invention (when used alone or in combination with one or more other additional therapeutic agents) will depend on the type of disease to be treated, the type of antibody, the type of polypeptide comprising the variant Fc region, the severity and course of the disease, whether the antibody or polypeptide comprising the variant Fc region is administered for preventive or therapeutic purposes, previous therapy, the patient's clinical history and response to the antibody or polypeptide comprising the variant Fc region, and the discretion of the attending physician. The antibody or polypeptide comprising a variant Fc region is suitably administered to the patient at one time or over a series of treatments. Depending on the type and severity of the disease, about 1 micro g/kg to 15 mg/kg (e.g. 0.1 mg/kg-10 mg/kg) of antibody or polypeptide comprising a variant Fc region can be an initial candidate dosage for administration to the patient, whether, for example, by one or more separate administrations, or by continuous infusion. One typical daily dosage might range from about 1 micro g/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or polypeptide comprising the variant Fc regio would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody or polypeptide comprising the variant Fc region). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-DENV antibody. It is likewise understood that any of the above formulations or therapeutic methods may be carried out using an immunoconjugate of the invention in place of or in addition to a polypeptide comprising a variant Fc region provided herein.

H. Articles of Manufacture

In another aspect of the invention, an article of manufacture containing materials useful for the treatment, prevention and/or diagnosis of the disorders described above is provided. The article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active ingredient in the composition is an antibody or a polypeptide comprising a variant Fc region of the invention. The label or package insert indicates that the composition is used for treating the condition of choice. Moreover, the article of manufacture may comprise (a) a first container with a composition contained therein, wherein the composition comprises an antibody or a polypeptide comprising a variant Fc region of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-DENV antibody. It is likely understood that any of the above articles of manufacture may include an immunoconjugate of the invention in place of or in addition to a polypeptide comprising a variant Fc region.

III. EXAMPLES

The following are examples of methods and compositions of the invention. It is understood that various other embodiments may be practiced, given the general description provided above.

Example 1: Preparation of Antigens and Antibodies

Expression and Purification of Recombinant Soluble E Protein from DENV-1, DENV-2, DENV-3, and DENV-4

Recombinant soluble E proteins (0.8E-His) from DENV-1, DENV-2, DENV-3, and DENV-4 with carboxy terminal 8× Histidine tag (SEQ ID NOs: 65-68, respectively) were expressed transiently using FreeStyle293-F cell line or Expi293 cell line (Thermo Fisher, Carlsbad, CA, USA). By expressing prM0.8E-His from DENV-1, DENV-2, DENV-3, and DENV-4 (SEQ ID NOs: 61-64, respectively), prM0.8E-His was expressed as a single polypeptide in the cells, which is then intracellularly processed to be cleaved between prM and 0.8E-His. As a result, 0.8E-His was secreted into the cell culture media. Conditioned media containing 0.8E-His was applied to a column packed with an immobilized metal affinity chromatography (IMAC) resin charged with nickel or cobalt, followed by elution with imidazole. Fractions containing 0.8E-His were pooled and applied to a Superdex 200 gel filtration column (GE healthcare, Uppsala, Sweden). Fractions containing 0.8E-His was pooled and stored at −80° C.

Expression and Purification of Recombinant Human FcγRs

Extracellular domains of human FcγRs were prepared by the following method. First, a gene of the extracellular domain of FcγR was synthesized by a method well known to those skilled in the art. At that time, the sequence of each FcγR was produced based on the information registered at NCBI. Specifically, FcγRIa was produced based on the sequence of NCBI Accession No. NM_000566 (Version No. NM_000566.3), FcγRIIa was produced based on the sequence of NCBI Accession No. NM_001136219 (Version No. NM_001136219.1), FcγRIIb was produced based on the sequence of NCBI Accession No. NM_004001 (Version No. NM_004001.3), FcγRIIIa was produced based on the sequence of NCBI Accession No. NM_001127593 (Version No. NM_001127593.1), and FcγRIIIb was produced based on the sequence of NCBI Accession No. NM_000570 (Version No. NM_000570.3), and a His tag was attached to the C terminus of each FcγR construct. Furthermore, the presence of polymorphism is known for FcγRIIa, FcγRIIIa, and FcγRIIIb, and the polymorphic sites were produced by referring to Warmerdam et al. (J Exp Med (1990) 172, 19-25) for FcγRIIa; Wu et al. (J Clin Invest (1997) 100, 1059-1070) for FcγRIIIa; and Ory et al. (J Clin Invest (1989) 84, 1688-1691) for FcγRIIIb.

Expression vectors were constructed by inserting into animal cell expression vectors the obtained gene fragments. The constructed expression vectors were transiently introduced into human embryonic kidney cancer cell-derived FreeStyle293 cells (Invitrogen) to express the proteins of interest. The liquids prepared by filtering through a 0.22-μm filter the culture supernatants obtained from the culture media of the above cells subjected to transient introduction, were purified, in principle, by the following four steps: (i)

cation-exchange column chromatography (SP Sepharose FF); (ii) affinity column chromatography for His-tag (His-Trap HP); (iii) gel filtration column chromatography (Superdex200); and (iv) sterile filtration. To purify FcγRI, anion-exchange column chromatography with Q sepharose FF was used for step (i). The absorbance of the purified protein was measured at 280 nm using a spectrophotometer. Based on the measured values, the concentrations of purified proteins were calculated using the extinction coefficient determined by a method such as PACE (Protein Science (1995) 4, 2411-2423).

Expression and Purification of Recombinant Mouse FcγRs

The extracellular domain of mouse FcγRs (mFcγRs) were prepared by the following method: first, the gene of the FcγR extracellular domain was synthesized by a method generally known to those skilled in the art. For this synthesis, the sequence of each FcγR was prepared on the basis of the information registered in NCBI. Specifically, mFcγRI was prepared on the basis of the sequence of NCBI Reference Sequence: NP_034316.1; mFcγRIIb was prepared on the basis of the sequence of NCBI Reference Sequence: NP_034317.1; mFcγRIII was prepared on the basis of the sequence of NCBI Reference Sequence: NP_034318.2; and mFcγRIV was prepared on the basis of the sequence of NCBI Reference Sequence: NP_653142.2. Each of these sequences was C-terminally tagged with a His tag.

Each obtained gene fragment was inserted into vectors for expression in animal cells to prepare expression vectors. The prepared expression vectors were transiently transferred to human embryonic kidney cancer cell-derived FreeStyle 293 cells (Invitrogen) to express the protein of interest. The obtained culture supernatant was recovered and then passed through a 0.22-μm filter to obtain a culture supernatant. The obtained culture supernatant was purified, as a rule, by the following four steps: (i) ion-exchanged column chromatography, (ii) affinity column chromatography for His tag (HisTrap HP), (iii) gel filtration column chromatography (Superdex 200), and (iv) sterile filtration. The ion-exchanged column chromatography of step (i) was carried out using Q Sepharose HP for mFcγRI, SP Sepharose FF for mFcγRIIb and mFcγRIV, and SP Sepharose HP for mFcγRIII. D-PBS(-) was used as a solvent in step (iii) or later, while D-PBS(-) containing 0.1 M arginine was used for mFcγRIII. The absorbance was measured for each purified protein at 280 nm using a spectrophotometer, and the concentration of the purified protein was calculated by use of an extinction coefficient calculated from the obtained value by a method such as PACE (Protein Science (1995) 4, 2411-2423).

Expression and Purification of Recombinant Human FcRn

FcRn is a heterodimer of FcRn alpha chain and beta2-microglobulin. Oligo-DNA primers were prepared based on the published human FcRn gene sequence (J Exp Med (1994) 180, 2377-2381). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the extracellular domain containing the signal region (Met1-Leu290) was amplified by PCR, and inserted into a mammalian cell expression vector. Likewise, oligo-DNA primers were prepared based on the published human beta2-microglobulin gene sequence (Proc Natl Acad Sci USA (2002) 99, 16899-16903). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the whole protein containing a signal region (Met1-Met119) was amplified by PCR and inserted into a mammalian cell expression vector.

Soluble human FcRn was expressed by the following procedure. The plasmids constructed for expressing human FcRn alpha chain (SEQ ID NO: 81) and beta2-microglobulin (SEQ ID NO: 82) were introduced into cells of the human embryonic kidney cancer-derived cell line HEK293H (Invitrogen) by the lipofection method using PEI (Polyscience). The resulting culture supernatant was collected, and FcRn was purified using IgG Sepharose 6 Fast Flow (Amersham Biosciences), followed by further purification using HiTrap Q HP (GE Healthcare) (J Immunol (2002) 169, 5171-5180).

Expression and Purification of Recombinant Antibodies

Recombinant antibodies were expressed transiently using either FreeStyle293-F cell line or Expi293 cell line (Thermo Fisher, Carlsbad, CA, USA). Purification from the conditioned media expressing antibodies was done with conventional method using protein A. Gel filtration was further conducted if necessary.

Expression and Purification of Recombinant Soluble Human CD154

The human CD154 gene was synthesized based on the published protein sequence (NP_000065.1). A DNA fragment encoding the soluble form of human CD154 (shCD154) with a FLAG tag was prepared by PCR, using the synthesized DNA as template, and the resulting DNA fragments were inserted into a mammalian cell expression vector, thereby producing an FLAG-shCD154 (SEQ ID NO: 106) expression vector. The nucleotide sequences of the obtained expression vectors were determined using conventional methodologies known to persons skilled in the art. The FLAG-shCD154 was expressed using the FreeStyle 293 cell line (Invitrogen) as described by the protocol provided by the manufacturer. After transfection, the cells were grown for an appropriate time before the conditioned medium was harvested. The conditioned medium was subjected to a cation exchange chromatography using 25 mM MES (pH6.0), and FLAG-shCD154 was eluted with continuous gradient 25 mM MES, 1M NaCl (pH6.0). The peak fractions were pooled, concentrated using AmiconUltra Ultracel and subjected to a gel-filtration chromatography using phosphate buffered saline (Wako). The peak fractions were again pooled and concentrated using AmiconUltra Ultracel, then sterilized by filtration with 0.22 micrometer PVDF membrane filter. To determine the concentration of the purified FLAG-shCD154, absorbance was measured at 280 nm using a spectrophotometer. The protein concentrations were calculated from the determined values using an absorbance coefficient calculated by the method described in Protein Science (1995) 4: 2411-2423.

Example 2: Generation of Antibody Variants with Improved Affinity to DENV E Protein The genes encoding the VH (3CH, SEQ ID NO: 1) and VL (3CL, SEQ ID NO: 7) of an anti-DENV E protein antibody were synthesized and combined with a human IgG1 CH (SG182, SEQ ID NO: 46) and a human CL (SK1, SEQ ID NO: 60), respectively, and both constructs were cloned into a single expression vector. The antibody is referred to herein as DG_3CH-SG182/3CL-SK1, or as 3C.

A number of mutations and their combinations were examined to identify mutations and combinations that improved the binding properties of 3C. Multiple mutations were then introduced to the variable regions to enhance the binding affinity to E protein. Optimized VH variants, 3CH912 (SEQ ID NIO: 2), 3CH953 (SEQ ID NO: 3), 3CH954 (SEQ ID NO: 4), 3CH955 (SEQ ID NO: 5), 3CH1047 (SEQ ID NO: 6), 3CH987 (SEQ ID NO: 90), 3CH989 (SEQ ID NO: 91), 3CH992 (SEQ ID NO: 92), 3CH1000 (SEQ ID NO: 93), 3CH1046 (SEQ ID NO: 94), 3CH1049 (SEQ ID NO: 95), and optimized VL variants, 3CL499 (SEQ ID NO: 8), 3CL563 (SEQ ID NO: 9), 3CL658 (SEQ ID NO: 10), 3CL012 (SEQ ID NO: 96), 3CL119 (SEQ ID NO: 97), 3CL633 (SEQ ID NO: 98), 3CL666 (SEQ ID NO: 99), 3CL668 (SEQ ID NO: 100), were thus generated. The genes encoding VH were combined with a human IgG1 CH (any one of SG182, SEQ ID NO: 46; SG1095, SEQ ID NO: 54; or SG1106, SEQ ID NO: 59), and the genes encoding VL were combined with a human CL (SK1, SEQ ID NO: 60). Each of them was cloned into an expression vector. The amino acid sequences of the antibody variants are summarized in Table 2. One of the variants, DG_3CH1047-SG182/3CL658-SK1, is also referred to herein as 3Cam and another variant, DG_3CH1047-SG182/3CL-SK1, is referred to herein as 3Cam2.

Antibodies were expressed in HEK293 cells co-transfected with mixture of heavy and light chain expression vectors, and were purified by protein A.

TABLE 2

Amino acid sequences of 3C and 3C variants

| Antibody | VH | HL | HVR-H1 | HVR-H2 | HVR-H3 | HVR-L1 | HVR-L2 | HVR-L3 | CH | CL |
|---|---|---|---|---|---|---|---|---|---|---|
| DG_3CH-SG182 3CL-SK1 | 1 | 7 | 11 | 13 | 16 | 21 | 24 | 27 | 46 | 60 |
| DG_3CH912-SG182 3CL-SK1 | 2 | 7 | 11 | 14 | 17 | 21 | 24 | 27 | 46 | 60 |
| DG_3CH953-SG182 3CL-SK1 | 3 | 7 | 11 | 15 | 17 | 21 | 24 | 27 | 46 | 60 |
| DG_3CH954-SG182/3CL-SK1 | 4 | 7 | 11 | 15 | 18 | 21 | 24 | 27 | 46 | 60 |
| DG_3CH955-SG182 3CL-SK1 | 5 | 7 | 11 | 15 | 19 | 21 | 24 | 27 | 46 | 60 |
| DG_3CH-SG182 3CL499-SK1 | 1 | 8 | 11 | 13 | 16 | 21 | 25 | 28 | 46 | 60 |
| DG_3CH-SG182 3CL563-SK1 | 1 | 9 | 11 | 13 | 16 | 22 | 25 | 29 | 46 | 60 |
| DG_3CH953-SG182/3CL499-SK1 | 3 | 8 | 11 | 15 | 17 | 21 | 25 | 28 | 46 | 60 |
| DG_3CH953-SG182/3CL563-SK1 | 3 | 9 | 11 | 15 | 17 | 22 | 25 | 29 | 46 | 60 |
| DG_3CH955-SG182 3CL499-SK1 | 5 | 8 | 11 | 15 | 19 | 21 | 25 | 28 | 46 | 60 |
| DG_3CH955-SG182/3CL563-SK1 | 5 | 9 | 11 | 15 | 19 | 22 | 25 | 29 | 46 | 60 |
| DG_3CH1047-SG182/3CL658-SK1 | 6 | 10 | 12 | 15 | 20 | 23 | 26 | 30 | 46 | 60 |
| DG_3CH1000-SG182 3CL-SK1 | 93 | 7 | 12 | 15 | 17 | 21 | 24 | 27 | 46 | 60 |
| DG_3CH1047-SG182 3CL-SK1 | 6 | 7 | 12 | 15 | 20 | 21 | 24 | 27 | 46 | 60 |
| DG_3CH953-SG1095 3CL-SK1 | 3 | 7 | 11 | 15 | 17 | 21 | 24 | 27 | 54 | 60 |
| DG_3CH1000-SG1095/3CL-SK1 | 93 | 7 | 12 | 15 | 17 | 21 | 24 | 27 | 54 | 60 |
| DG_3CH1047-SG1095/3CL-SK1 | 6 | 7 | 12 | 15 | 20 | 21 | 24 | 27 | 54 | 60 |
| DG_3CH953-SG1106 3CL-SK1 | 3 | 7 | 11 | 15 | 17 | 21 | 24 | 27 | 59 | 60 |
| DG_3CH1000-SG1106 3CL-SK1 | 93 | 7 | 12 | 15 | 17 | 21 | 24 | 27 | 59 | 60 |
| DG_3CH1047-SG1106/3CL-SK1 | 6 | 7 | 12 | 15 | 20 | 21 | 24 | 27 | 59 | 60 |
| DG_3CH953-SG1095/3CL012-SK1 | 3 | 96 | 11 | 15 | 17 | 21 | 24 | 30 | 54 | 60 |
| DG_3CH1000-SG1095 3CL012-SK1 | 93 | 96 | 12 | 15 | 17 | 21 | 24 | 30 | 54 | 60 |
| DG_3CH1047-SG1095 3CL012-SK1 | 6 | 96 | 12 | 15 | 20 | 21 | 24 | 30 | 54 | 60 |
| DG_3CH953-SG1106/3CL012-SK1 | 3 | 96 | 11 | 15 | 17 | 21 | 24 | 30 | 59 | 60 |
| DG_3CH1000-SG1106 3CL012-SK1 | 93 | 96 | 12 | 15 | 17 | 21 | 24 | 30 | 59 | 60 |
| DG_3CH1047-SG1106 3CL012-SK1 | 6 | 96 | 12 | 15 | 20 | 21 | 24 | 30 | 59 | 60 |
| DG_3CH953-SG1095 3CL119-SK1 | 3 | 97 | 11 | 15 | 17 | 21 | 23 | 24 | 27 | 54 | 60 |
| DG_3CH1000-SG1095 3CL119-SK1 | 93 | 97 | 12 | 15 | 17 | 23 | 24 | 27 | 54 | 60 |
| DG_3CH1047-SG1095 3CL119-SK1 | 6 | 97 | 12 | 15 | 20 | 23 | 24 | 27 | 54 | 60 |
| DG_3CH953-SG1106 3CL119-SK1 | 3 | 97 | 11 | 15 | 17 | 23 | 24 | 27 | 59 | 60 |
| DG_3CH1000-SG1106 3CU19-SK1 | 93 | 97 | 12 | 15 | 17 | 23 | 24 | 27 | 59 | 60 |
| DG_3CH1047-SG1106/3CL119-SK1 | 6 | 97 | 12 | 15 | 20 | 23 | 24 | 27 | 59 | 60 |
| DG_3CH1049-SG182/3CL-SK1 | 95 | 7 | 12 | 15 | 20 | 21 | 24 | 27 | 46 | 60 |
| DG_3CH1046-SG182/3CL-SK1 | 94 | 7 | 12 | 15 | 17 | 21 | 24 | 27 | 46 | 60 |
| DG_3CH989-SG182/3CL-SK1 | 91 | 7 | 11 | 15 | 17 | 21 | 24 | 27 | 46 | 60 |
| DG_3CH992-SG182/3CL-SK1 | 92 | 7 | 101 | 15 | 17 | 21 | 24 | 27 | 46 | 60 |
| DG_3CH987-SG182/3Cl-SK1 | 90 | 7 | 101 | 15 | 17 | 21 | 24 | 27 | 46 | 60 |
| DG_3CH1049-SG182/3Cl012-SK1 | 95 | 96 | 12 | 15 | 20 | 21 | 24 | 30 | 46 | 60 |
| DG_3CH1046-SG182/3Cl012-SK1 | 94 | 96 | 12 | 15 | 17 | 21 | 24 | 30 | 46 | 60 |
| DG_3CH989-SG182/3Cl012-SK1 | 91 | 96 | 11 | 15 | 17 | 21 | 24 | 30 | 46 | 60 |
| DG_3CH992-SG182/3CL012-SK1 | 92 | 96 | 101 | 15 | 17 | 21 | 24 | 30 | 46 | 60 |
| DG_3CH987-SG182/3Cl012-SK1 | 90 | 96 | 101 | 15 | 17 | 21 | 24 | 30 | 46 | 60 |
| DG_3CH1049-SG182/3Cl119-SK1 | 95 | 97 | 12 | 15 | 20 | 23 | 24 | 27 | 46 | 60 |
| DG_3CH1046-SG182/3Cl119-SK1 | 94 | 97 | 12 | 15 | 17 | 23 | 24 | 27 | 46 | 60 |
| DG_3CH989-SG182/3CU19-SK1 | 91 | 97 | 11 | 15 | 17 | 23 | 24 | 27 | 46 | 60 |
| DG_3CH992-SG182/3Cl119-SK1 | 92 | 97 | 101 | 15 | 17 | 23 | 24 | 27 | 46 | 60 |
| DG_3CH987-SG182/3Cl119-SK1 | 90 | 97 | 101 | 15 | 17 | 23 | 24 | 27 | 46 | 60 |
| DG_3CH1049-SG182/3Cl668-SK1 | 95 | 100 | 12 | 15 | 20 | 21 | 24 | 30 | 46 | 60 |
| DG_3CH1046-SG182/3Cl668-SK1 | 94 | 100 | 12 | 15 | 17 | 21 | 24 | 30 | 46 | 60 |
| DG_3CH989-SG182/3Cl668-SK1 | 91 | 100 | 11 | 15 | 17 | 21 | 24 | 30 | 46 | 60 |
| DG_3CH1049-SG182/3Cl666-SK1 | 95 | 99 | 12 | 15 | 20 | 23 | 24 | 27 | 46 | 60 |
| DG_3CH1046-SG182/3Cl666-SK1 | 94 | 99 | 12 | 15 | 17 | 23 | 24 | 27 | 46 | 60 |
| DG_3CH989-SG182/3Cl666-SK1 | 91 | 99 | 11 | 15 | 17 | 23 | 24 | 27 | 46 | 60 |
| DG_3CH1049-SG182/3Cl633-SK1 | 95 | 98 | 12 | 15 | 20 | 21 | 24 | 27 | 46 | 60 |
| DG_3CH1046-SG182/3Cl633-SK1 | 94 | 98 | 12 | 15 | 17 | 21 | 24 | 27 | 46 | 60 |
| DG_3CH989-SG182/3Cl633-SK1 | 91 | 98 | 11 | 15 | 17 | 21 | 24 | 27 | 46 | 60 |
| DG_3CH953-SG182/3Cl668-SK1 | 3 | 100 | 11 | 15 | 17 | 21 | 24 | 30 | 46 | 60 |
| DG_3CH1000-SG182/3Cl668-SK1 | 93 | 100 | 12 | 15 | 17 | 21 | 24 | 30 | 46 | 60 |

TABLE 2-continued

Amino acid sequences of 3C and 3C variants

| | SEQ ID NO: | | | | | | | | | |
|---|---|---|---|---|---|---|---|---|---|---|
| Antibody | VH | HL | HVR-H1 | HVR-H2 | HVR-H3 | HVR-L1 | HVR-L2 | HVR-L3 | CH | CL |
| DG_3CH953-SG182/3Cl666-SK1 | 3 | 99 | 11 | 15 | 17 | 23 | 24 | 27 | 46 | 60 |
| DG_3CH1000-SG182/3Cl666-SK1 | 93 | 99 | 12 | 15 | 17 | 23 | 24 | 27 | 46 | 60 |
| DG_3CH953-SG182/3Cl633-SK1 | 3 | 98 | 11 | 15 | 17 | 21 | 24 | 27 | 46 | 60 |
| DG_3CH1000-SG182/3Cl633-SK1 | 93 | 98 | 12 | 15 | 17 | 21 | 24 | 27 | 46 | 60 |
| DG_3CH1047-SG182/3Cl666-SK1 | 6 | 99 | 12 | 15 | 20 | 23 | 24 | 27 | 46 | 60 |
| DG_3CH992-SG182/3Cl666-SK1 | 92 | 99 | 101 | 15 | 17 | 23 | 24 | 27 | 46 | 60 |
| DG_3CH1047-SG182/3Cl633-SK1 | 6 | 98 | 12 | 15 | 20 | 21 | 24 | 27 | 46 | 60 |
| DG_3CH992-SG182/3Cl633-SK1 | 92 | 98 | 101 | 15 | 17 | 21 | 24 | 27 | 46 | 60 |

The affinity of anti-DENV E protein antibodies binding to E protein of DENV-1, DENV-2, DENV-3, and DENV-4 were determined at 25° C. using Biacore T200 instrument (GE Healthcare). Anti-histidine antibody (GE Healthcare) was immobilized onto all flow cells of a CM4 sensor chip using an amine coupling kit (GE Healthcare). All antibodies and analytes were prepared in PBS, pH 7.4, containing 20 mMV sodium phosphate, 150 mM NaCl, 0.05% Tween 20 and 0.005% NaN$_3$. E protein of DENV-1, DENV-2, DENV-3, and DENV-4 with C-terminal His-tag was captured onto flow cell 2 or 3, with flow cell 1 as reference flow cell. Capture level for E protein was aimed at 200 resonance unit (RU). Anti-DENV E protein antibodies were injected at 250 nM over the entire sensor surface for 180 seconds, followed by 300 seconds of dissociation. The sensor surface was regenerated after each cycle using 10 mM Gly-HCl pH1.5. Binding affinity was determined by processing and fitting the data to 1:1 binding model using Biacore T200 Evaluation software, version 2.0 (GE Healthcare).

Figure 10:
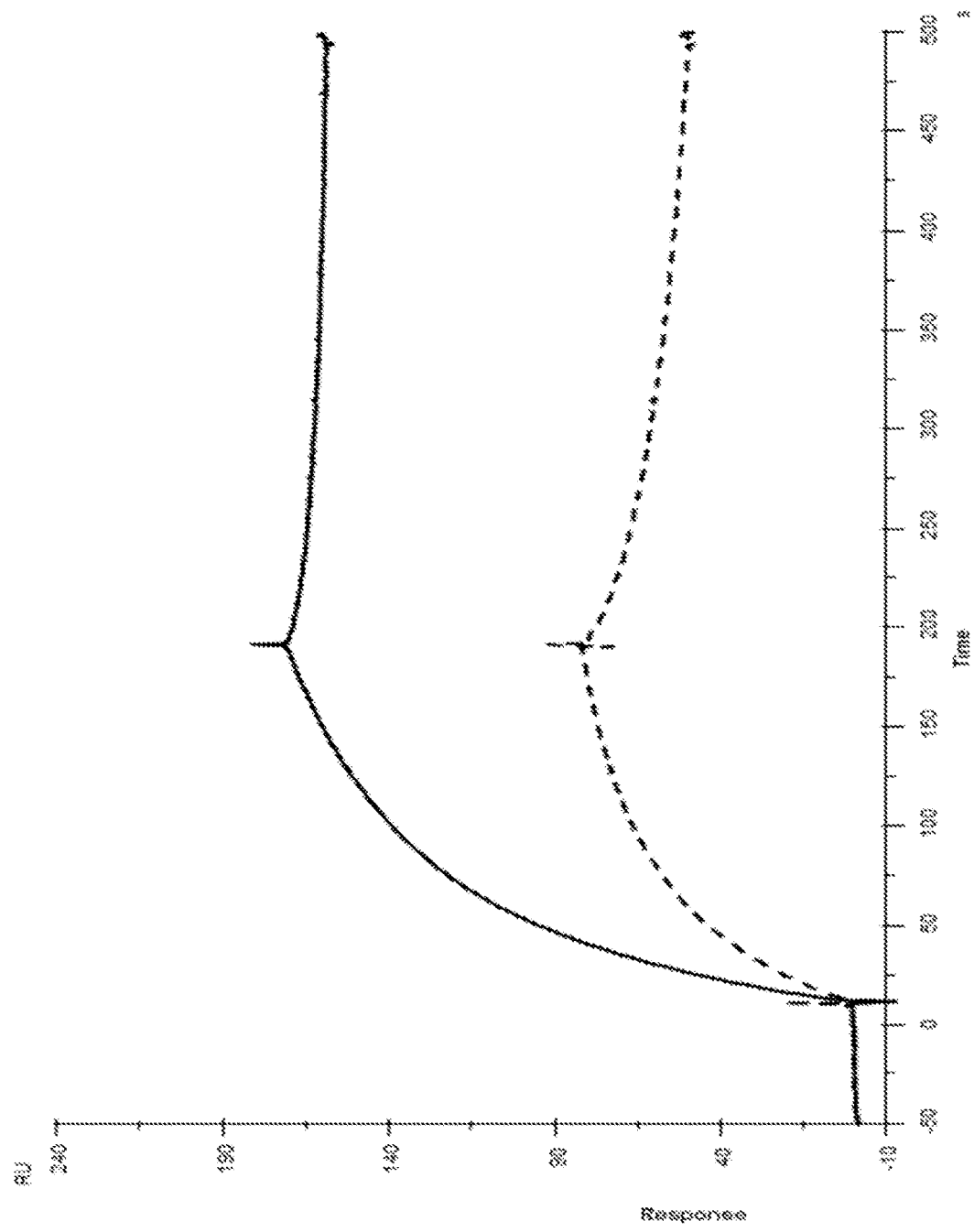
FIGS. 10 (A)-(D) illustrate BIACORE® sensorgrams of anti-DENV antibodies 3C and 3Cam2 towards DENV-1 E protein (A), DENV-2 E protein (B), DENV-3 E protein (C), and DENV-4 E protein (D), as described in Example 2.
Figure 10:
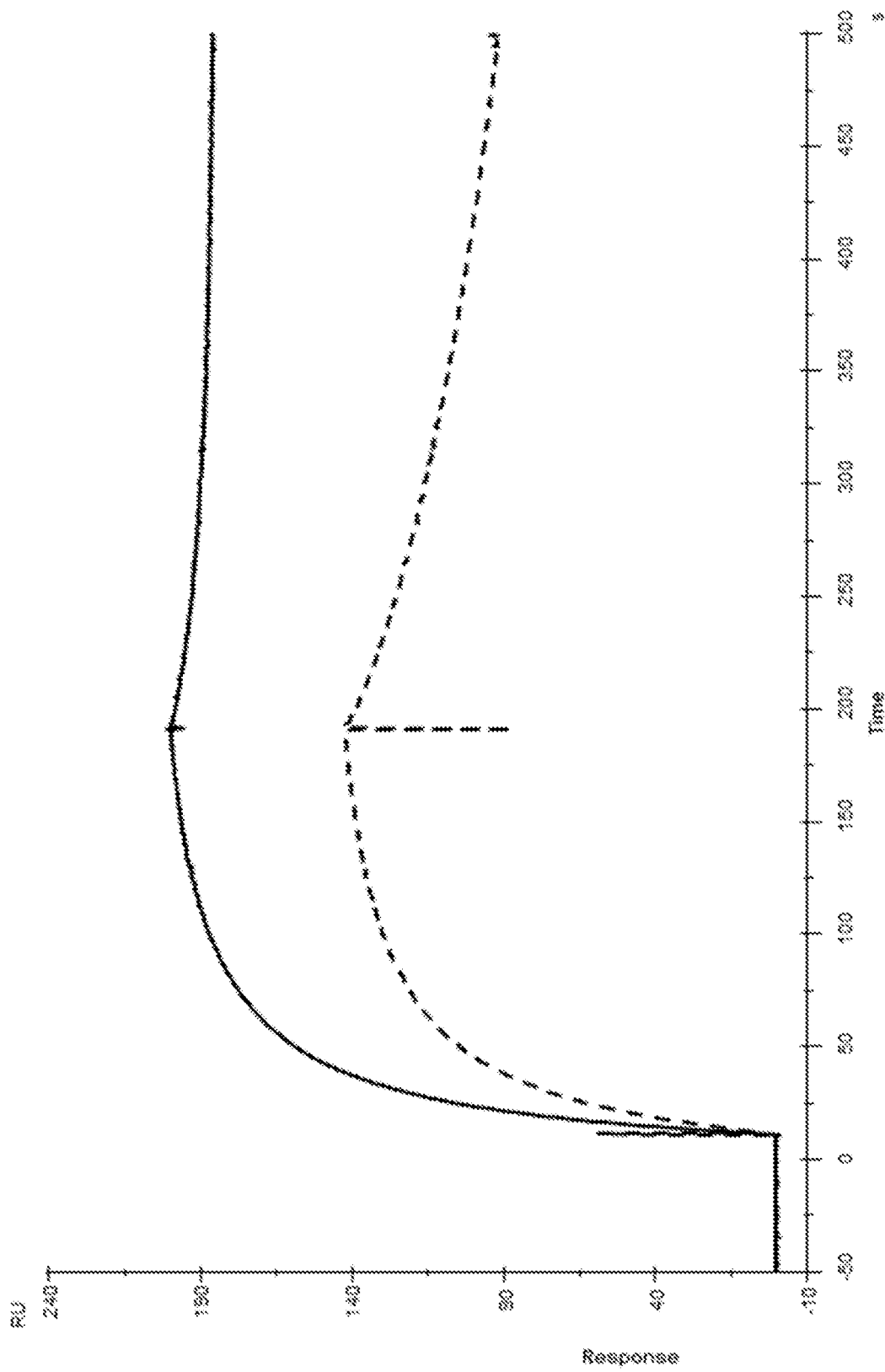
Figure 10:
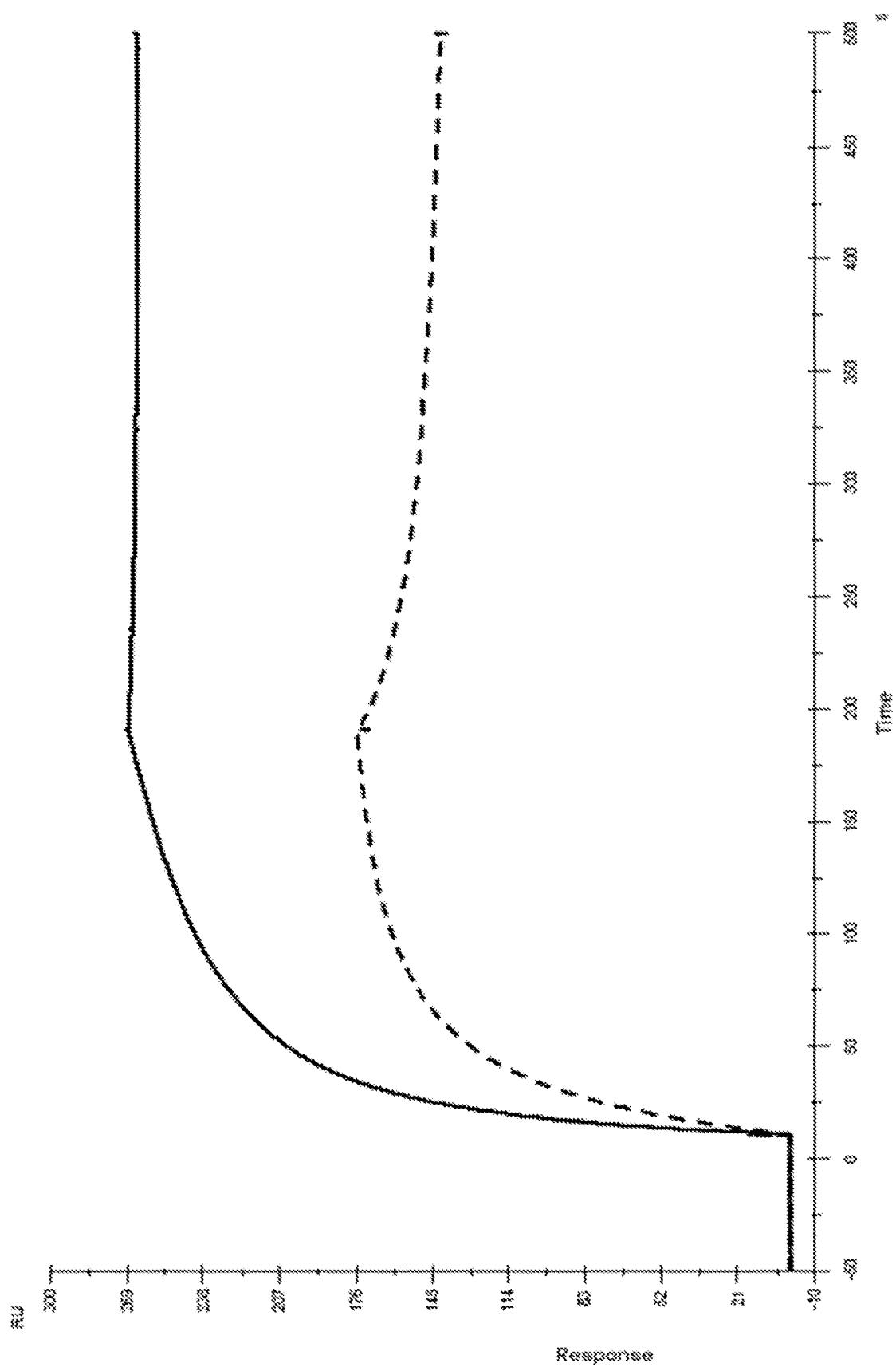
Figure 10:
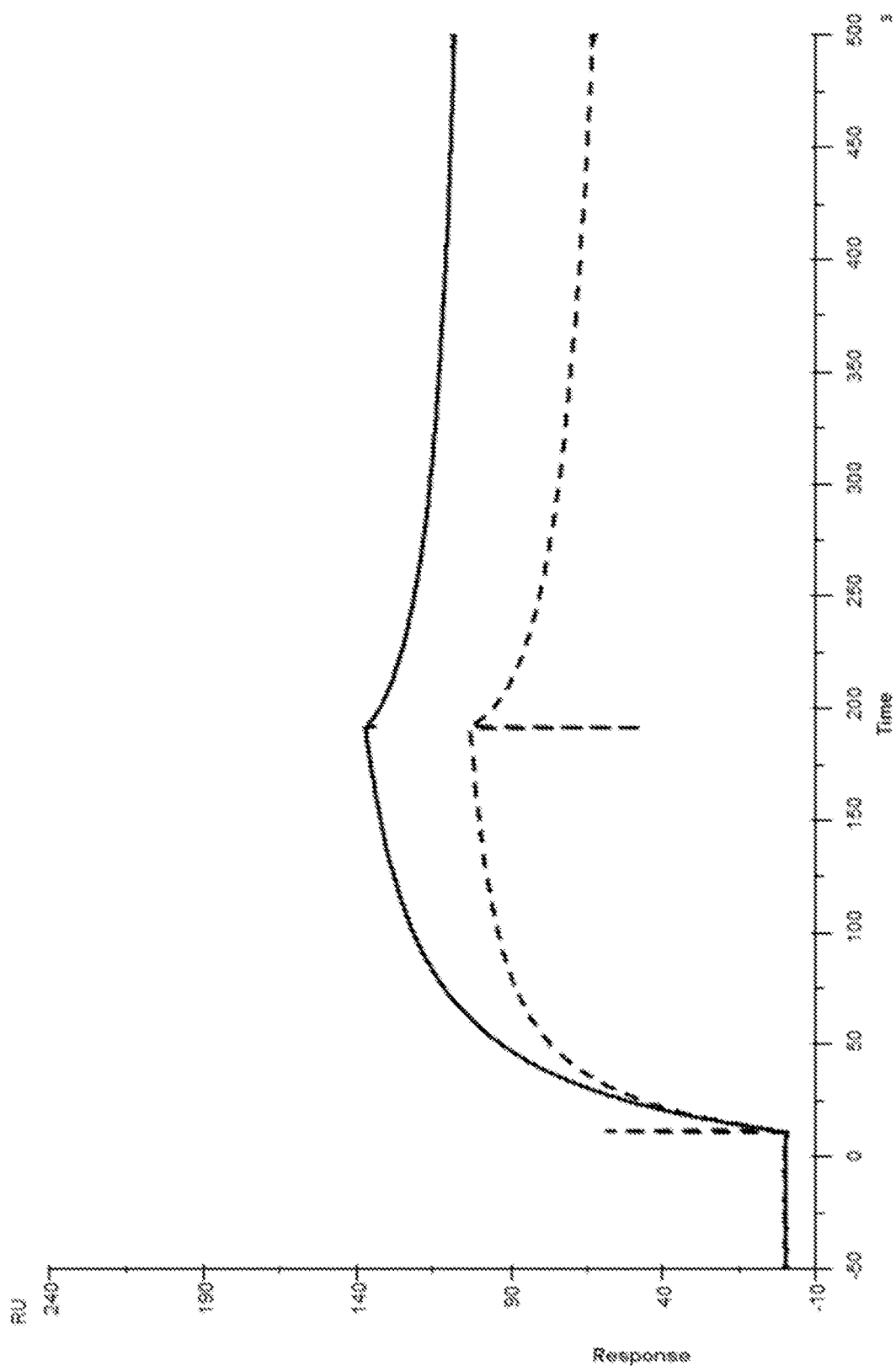

Tables 3a and 3b show the affinity (Kd) of anti-DENV E protein antibodies binding to E protein of DENV-1 (described as DV1 in the Table), DENV-2 (described as DV2 in the Table), DENV-3 (described as DV3 in the Table), and DENV-4 (described as DV4 in the Table). Each 3C variant showed increased binding affinity against all four DENV serotypes, compared to the parent 3C. As examples, the sensorgrams of the parent antibody 3C (DG_3CH-SG182/3CL-SK1) and one of the variant antibody 3Cam (DG_3CH1047-SG182/3CL658-SK1) are shown in FIG. 1. Also, the sensorgrams of the parent antibody 3C (DG_3CH-SG182/3CL-SK1) and one of the variant antibody 3Cam2 (DG_3CH1047-SG182/3CL-SK1) are shown in FIG. 10.

TABLE 3a

Kd values of 3C and 3C variants against four DENV serotypes

| | KD (M) | | | |
|---|---|---|---|---|
| Fv variant | DV1 | DV2 | DV3 | DV4 |
| DG_3CH-SG182/3CL-SK1 | 3.21E-08 | 1.40E-08 | 6.07E-09 | 1.69E-08 |
| DG_3CH912-SG182/3CL-SK1 | 1.85E-09 | 8.11E-10 | 2.44E-10 | 8.78E-09 |
| DG_3CH953-SG182/3CL-SK1 | 1.41E-09 | 7.76E-10 | 1.36E-10 | 6.20E-09 |
| DG_3CH954-SG182/3CL-SK1 | 8.87E-10 | 1.22E-10 | 1.24E-10 | 4.35E-09 |
| DG_3CH955-SG182/3CL-SK1 | 1.13E-09 | 7.94E-10 | 2.05E-10 | 7.80E-09 |
| DG_3CH-SG182/3CL499-SK1 | 1.11E-08 | 4.73E-09 | 4.03E-09 | 8.35E-09 |
| DG_3CH-SG182/3CL563-SK1 | 1.34E-08 | 4.43E-09 | 3.52E-09 | 1.18E-08 |
| DG_3CH953-SG182/3CL499-SK1 | 1.46E-09 | 9.05E-10 | 2.11E-10 | 5.99E-09 |
| DG_3CH953-SG182/3CL563-SK1 | 1.88E-09 | 9.22E-10 | 2.64E-10 | 8.21E-09 |
| DG_3CH955-SG182/3CL499-SK1 | 1.26E-09 | 1.03E-09 | 3.31E-10 | 8.26E-09 |
| DG_3CH955-SG182/3CL563-SK1 | 1.91E-09 | 1.04E-09 | 2.90E-10 | 1.22E-08 |
| DG_3CH1047-SG182/3CL658-SK1 | 3.51E-09 | 7.65E-10 | 3.82E-12* | 9.11E-09 |
| DG_3CH1047-SG182/3CL-SK1 | 2.14E-09 | 8.43E-10 | 2.31E-13* | 5.61E-09 |

Note:
*strong binders, slow off rate <1E-05, KD cannot be uniquely determined.

TABLE 3b

Kd values of 3C and 3C variants against DENV1 and DENV3 serotypes

| | KD (M) | |
|---|---|---|
| Fv variant | DV1 | DV3 |
| DG_3CH-SG182/3CL-SK1 | 2.25E-08 | 6.35E-09 |
| DG_3CH1047-SG182/3CL658-SK1 | 2.98E-09 | 5.01E-12 * |
| DG_3CH953-SG182/3CL-SK1 | 1.80E-09 | 9.85E-13 * |
| DG_3CH1000-SG182/3CL-SK1 | 1.79E-09 | 3.49E-12 * |
| DG_3CH1047-SG182/3CL-SK1 | 2.06E-09 | 7.22E-11 * |
| DG_3CH953-SG1095/3CL-SK1 | 1.79E-09 | 7.03E-12 * |
| DG_3CH1000-SG1095/3CL-SK1 | 1.80E-09 | 1.68E-11 * |
| DG_3CH1047-SG1095/3CL-SK1 | 2.09E-09 | 2.93E-12 * |
| DG_3CH963-SG1106/3CL-SK1 | 1.85E-09 | 7.08E-12 * |
| DG_3CH1000-SG1106/3CL-SK1 | 1.84E-09 | 2.99E-13 * |
| DG_3CH1047-SG1106/3CL-SK1 | 2.12E-09 | 4.71E-12 * |
| DG_3CH953-SG1095/3CL012-SK1 | 1.86E-09 | 5.53E-12 * |
| DG_3CH1000-SG1095/3CL012-SK1 | 1.83E-09 | 9.59E-13 * |
| DG_3CH1047-SG1095/3CL012-SK1 | 2.21E-09 | 3.17E-12 * |
| DG_3CH953-SG1106/3CL012-SK1 | 1.89E-09 | 1.06E-11 * |
| DG_3CH1000-SG1106/3CL012-SK1 | 1.91E-09 | 1.01E-13 * |
| DG_3CH1047-SG1106/3CL012-SK1 | 2.18E-09 | 2.36E-12 * |
| DG_3CH963-SG1095/3CL119-SK1 | 1.99E-09 | 7.18E-12 * |
| DG_3CH1000-SG1095/3CL119-SK1 | 1.92E-09 | 4.28E-14 * |
| DG_3CH1047-SG1095/3CL119-SK1 | 2.23E-09 | 3.79E-12 * |
| DG_3CH953-SG1106/3CL119-SK1 | 1.96E-09 | 2.17E-12 * |
| DG_3CH1000-SG1106/3CL119-SK1 | 1.91E-09 | 1.82E-12 * |
| DG_3CH1047-SG1106/3CL119-SK1 | 2.29E-09 | 4.36E-12 * |

TABLE 3b-continued

Kd values of 3C and 3C variants against DENV1 and DENV3 serotypes

| Fv variant | KD (M) DV1 | KD (M) DV3 |
|---|---|---|
| DG_3CH1049-SG182/3CL-SK1 | 2.14E−09 | 2.39E−12 * |
| DG_3CH1046-SG182/3CL-SK1 | 1.91E−09 | 2.13E−13 * |
| DG_3CH989-SG182/3CL-SK1 | 1.84E−09 | 4.48E−13 * |
| DG_3CH992-SG182/3CL-SK1 | 2.02E−09 | 4.03E−12 * |
| DG_3CH987-SG182/3CL-SK1 | 1.82E−09 | 9.86E−13 * |
| DG_3CH1049-SG182/3CL012-SK1 | 2.26E−09 | 1.05E−12 * |
| DG_3CH1046-SG182/3CL012-SK1 | 1.92E−09 | 1.45E−13 * |
| DG_3CH989-SG182/3CL012-SK1 | 1.52E−09 | 9.67E−14 * |
| DG_3CH992-SG182/3CL012-SK1 | 1.72E−09 | 1.07E−12 * |
| DG_3CH987-SG182/3CL012-SK1 | 1.42E−09 | 2.67E−12 * |
| DG_3CH1049-SG182/3CL119-SK1 | 1.72E−09 | 5.09E−12 * |
| DG_3CH1046-SG182/3CL119-SK1 | 1.53E−09 | 2.73E−12 * |
| DG_3CH989-SG182/3CL119-SK1 | 1.53E−09 | 6.83E−12 * |
| DG_3CH992-SG182/3CL119-SK1 | 1.87E−09 | 5.15E−13 * |
| DG_3CH987-SG182/3CL119-SK1 | 1.53E−09 | 7.15E−13 * |
| DG_3CH1049-SG182/3CL668-SK1 | 1.70E−09 | 1.55E−12 * |
| DG_3CH1046-SG182/3CL668-SK1 | 1.56E−09 | 5.59E−13 * |
| DG_3CH989-SG182/3CL668-SK1 | 1.50E−09 | 3.03E−12 * |
| DG_3CH1049-SG182/3CL666-SK1 | 1.72E−09 | 2.95E−12 * |
| DG_3CH1046-SG182/3CL666-SK1 | 1.52E−09 | 4.70E−13 * |
| DG_3CH989-SG182/3CL666-SK1 | 1.50E−09 | 1.96E−12 * |
| DG_3CH1049-SG182/3CL633-SK1 | 1.73E−09 | 4.10E−12 * |
| DG_3CH1046-SG182/3CL633-SK1 | 1.64E−09 | 2.01E−13 * |
| DG_3CH989-SG182/3CL633-SK1 | 1.54E−09 | 2.37E−12 * |
| DG_3CH953-SG182/3CL668-SK1 | 1.68E−09 | 2.36E−12 * |
| DG_3CH1000-SG182/3CL668-SK1 | 1.68E−09 | 8.00E−13 * |
| DG_3CH953-SG182/3CL666-SK1 | 1.69E−09 | 5.48E−12 * |
| DG_3CH1000-SG182/3CL666-SK1 | 1.66E−09 | 2.50E−12 * |
| DG_3CH953-SG182/3CL633-SK1 | 1.65E−09 | 4.96E−12 * |
| DG_3CH1000-SG182/3CL633-SK1 | 1.77E−09 | 4.25E−12 * |
| DG_3CH1047-SG182/3CL666-SK1 | 9.82E−10 | 4.20E−11 * |
| DG_3CH992-SG182/3CL666-SK1 | 1.39E−09 | 8.02E−13 * |
| DG_3CH1047-SG182/3CL633-SK1 | 9.56E−10 | 4.37E−13 * |
| DG_3CH992-SG182/3CL633-SK1 | 1.27E−09 | 2.95E−12 * |

Note:
* strong binders, slow off rate <1E−05, KD cannot be uniquely determined.

Example 3: Generation of Antibody CH Variants for Improved Properties

Multiple mutations were introduced to a human IgG1 heavy chain constant region CH (SG182, SEQ ID NO: 46), and as a result of that, human IgG1 CH variants, SG192 (SEQ ID NO: 47), SG1085 (SEQ ID NO: 48), SG1086 (SEQ ID NO: 49), SG1087 (SEQ ID NO: 50), SG1088 (SEQ ID NO: 51), SG1089 (SEQ ID NO: 52), SG1090 (SEQ ID NO: 53), SG1095 (SEQ ID NO: 54), SG1096 (SEQ ID NO: 55), SG1097 (SEQ ID NO: 56), SG1098 (SEQ ID NO: 57), SG1105 (SEQ ID NO: 58), SG1106 (SEQ ID NO: 59), SG1109 (SEQ ID NO: 107), SG1044 (SEQ ID NO: 108), and SG1045 (SEQ ID NO: 109), were generated. The genes encoding the CH variants were combined with VH of 3C (3CH, SEQ ID NO: 1), one of the 3C variants (3CH1047, SEQ ID NO: 6), or an anti-CD154 antibody (SLAPH0336a, SEQ ID NO: 88). The VL gene of the anti-CD154 antibody (SLAPL0336a, SEQ ID NO: 89) was combined with a human CL (SK1, SEQ ID NO: 60). Each of them was cloned into an expression vector. The details of the CH variants are summarized in Table 4. The variable region of an anti-CD154 antibody SLAPH0336a/SLAPL0366a, which can form a large immune complex in the presence of the trimeric antigen CD154, were used so as to evaluate avidity binding of the CH variants to each Fc receptor.

Antibodies were expressed in HEK293 cells co-transfected with mixture of heavy and light chain expression vectors, and were purified by protein A.

TABLE 4

Amino acid sequences of variant Fc regions

| Variant name | ID | Mutations | SEQ ID NO: |
|---|---|---|---|
| WT | SG182 | — | 46 |
| LALA | SG192 | L234A, L235A | 47 |
| KWES | SG1085 | K326W, E333S | 48 |
| EFT + AE | SG1086 | G236A, S267E, H268F, S324T, I332E | 49 |
| EFT | SG1087 | S267E, H268F, S324T | 50 |
| LALA + KWES | SG1088 | L234A, L235A, K326W, E333S | 51 |
| LALA + EFT + AE | SG1089 | L234A, L235A, G236A, S267E, H268F, S324T, I332E | 52 |
| LALA + EFT | SG1090 | L234A, L235A, S267E, H268F, S324T | 53 |
| LALA + KAES | SG1095 | L234A, L235A, K326A, E333S | 54 |
| LALA + KDES | SG1096 | L234A, L235A, K326D, E333S | 55 |
| LALA + KEES | SG1097 | L234A, L235A, K326E, E333S | 56 |
| LALA + KMES | SG1098 | L234A, L235A, K326M, E333S | 57 |
| LALA + ACT3 + KAES | SG1105 | L234A, L235A, K326A, E333S, M428L, N434A, Y436T, Q438R, S440E | 58 |
| LALA + ACT5 + KAES | SG1106 | L234A, L235A, K326A, E333S, M428L, N434A, Q438R, S440E | 59 |
| KAES | SG1109 | K326A, E333S | 107 |
| LALA + ACT3 | SG1044 | L234A, L235A, M428L, N434A, Y436T, Q438R, S440E | 108 |
| LALA + ACT5 | SG1045 | L234A, L235A, M428L, N434A, Q438R, S440E | 109 |

Example 4: Binding Affinities of an Antibody with Fc Variants to Complement C1q

Human C1q Binding Assay

Figure 2:
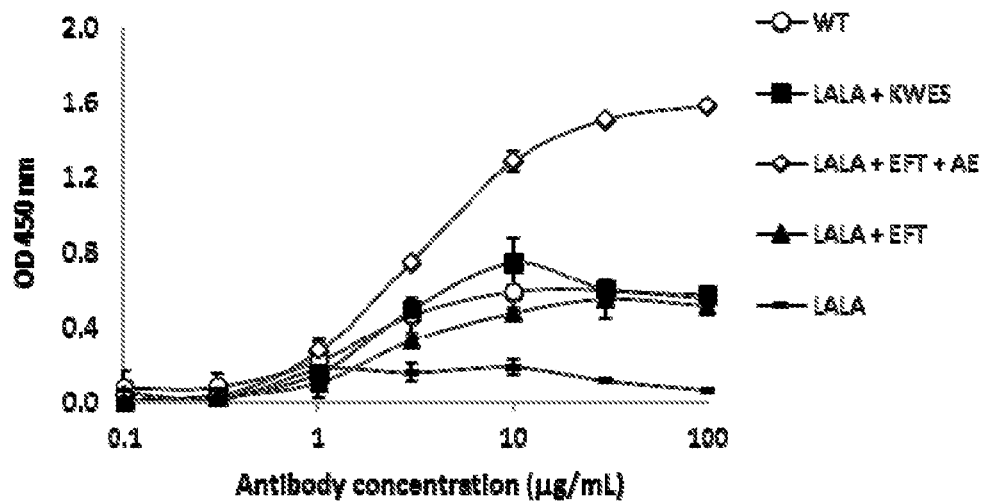
FIG. 2 illustrates binding affinities of antibodies with different Fc variants towards human C1q, as described in Example 4. The binding activities were measured by ELISA. The Fc variants tested are: WT, LALA+KWES, LALA+EFT+AE, LALA+EFT, and LALA.
Figure 3:
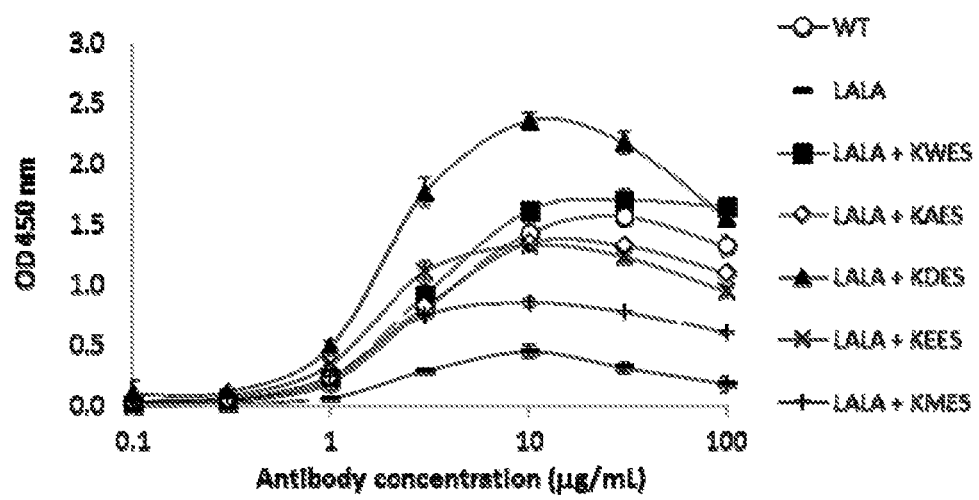
FIG. 3 illustrates binding affinities of antibodies with different Fc variants towards human C1q, as described in Example 4. The binding activities were measured by ELISA. The Fc variants tested are: WT, LALA, LALA+KWES, LALA+KAES, LALA+KDES, LALA+KEES, and LALA+KMES.
Figure 4:
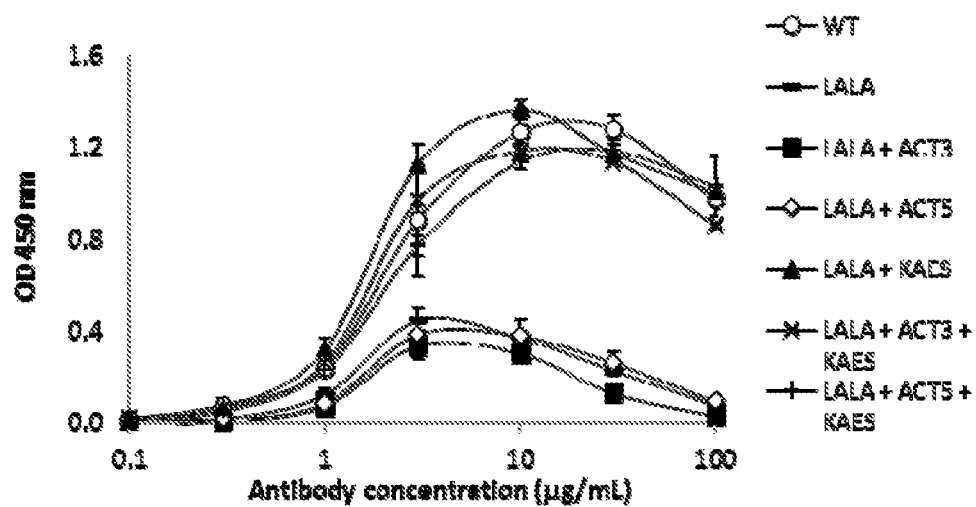
FIG. 4 illustrates binding affinities of antibodies with different Fc variants towards human C1q, as described in Example 4. The binding activities were measured by ELISA. The Fc variants tested are: WT, LALA, LALA+ACT3, LALA+ACT5, LALA+KAES, LALA+ACT3+KAES, and LALA+ACT5+KAES.

Anti-CD154 antibodies with Fc variants (in-house antibodies, which were generated using the method described in Example 3) were dispensed onto Nunc-ImmunoPlate MaxiSorp (Nalge Nunc International) and allowed to stand overnight at 4° C. After washing with PBST, the plate was blocked with TBST containing 0.5% BSA and 1× Block Ace: Blocking Reagent (DS Pharma) for 2 hours at room temperature. After washing the plate, human C1q (Calbiochem) was dispensed into the plate, and allowed to stand for 1 hour at room temperature. The plate was washed, and HRP-labelled anti-human C1q antibody (Bio Rad) was added to react for 1 hour at room temperature, and washing was performed. Subsequently, TMB Substrate (Invitrogen) was added. The signal was measured by a plate reader at a wavelength of 450 nm (test wave length) and 570 nm (reference wavelength). Binding affinity of the antibody having a wild type Fc region (WT) to human C1q was diminished by introducing LALA mutations into the Fc region, and the diminished binding affinity to human C1q was recovered by further introducing KWES, EFT, or EFT+ AE in addition to LALA mutations (FIG. 2). LALA+KMES mutations slightly increased the binding affinity, whereas LALA+KWES, LALA+KAES, and LALA+KEES mutants bound to C1q with comparable affinity to WT (FIG. 3). The binding property of LALA or LALA+KAES mutants described above was not affected by further introducing ACT3 or ACT5 mutations (FIG. 4).

Mouse C1q Binding Assay

Figure 5:
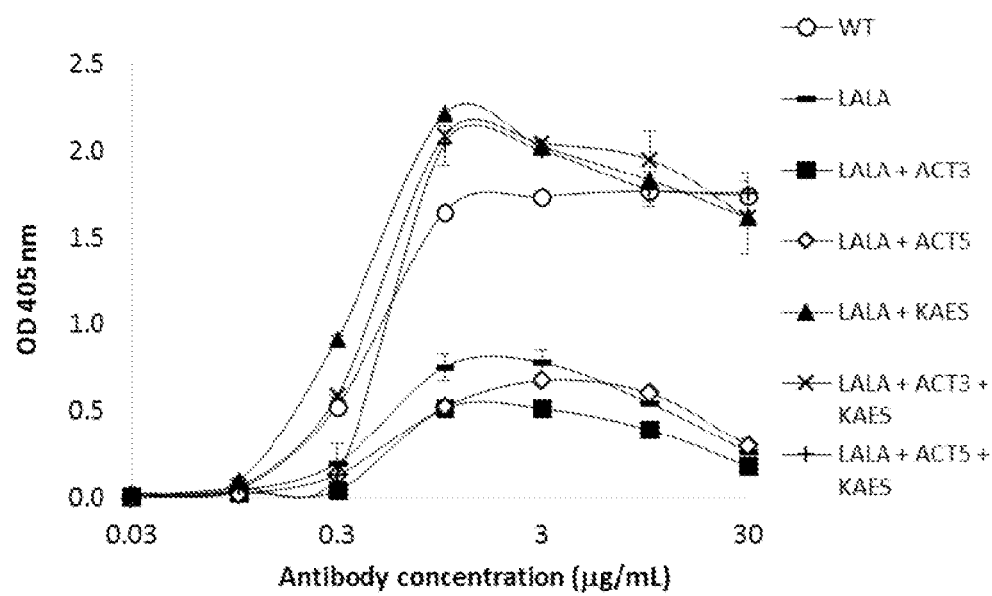
FIG. 5 illustrates binding affinities of antibodies with different Fc variants towards mouse C1q, as described in Example 4. The binding activities were measured by ELISA. The Fc variants tested are: WT, LALA, LALA+ACT3, LALA+ACT5, LALA+KAES, LALA+ACT3+KAES, and LALA+ACT5+KAES.

Anti-CD154 antibodies with Fc variants (in-house antibodies, which were generated using the method described in Example 3) were dispensed onto Nunc-ImmunoPlate MaxiSorp (Nalge Nunc International) and allowed to stand overnight at 4° C. After washing with PBST, the plate was blocked with TBST containing 0.5% BSA and 1× Block Ace: Blocking Reagent (DS Pharma) for 7 hours at 4° C. After washing the plate, 10% mouse plasma (Innovative Research) was dispensed into the plate, and allowed to stand overnight at 4° C. The plate was washed, and biotinylated anti-mouse C1q antibody (Hycult Biotech) was added to react for 1 hour at room temperature, and washing was performed. Streptavidin-HRP (Pierce) was added to react for 1 hour at room temperature, and washing was performed. Subsequently, ABTS ELISA HRP Substrate (KPL) was added. The signal was measured by a plate reader at a wavelength of 405 nm. Binding affinity of the antibody having a wild type Fc region (WT) to mouse C1q was diminished by introducing LALA mutations into the Fc region, and the diminished binding affinity to mouse C1q was recovered by further introducing KAES in addition to LALA mutations. The binding property of LALA or LALA+KAES mutants described above was not affected by further introducing ACT3 or ACT5 mutations (FIG. 5).

Example 5: Biacore Analysis for Fc Variants Binding to FcγRs and FcRn

The binding of Fc variants towards human or mouse FcγRs and human FcRn at pH 7.4 were determined at 25° C. using Biacore T200 instrument (GE Healthcare). All antibodies and FcγRs or FcRn were prepared in PBS-P pH 7.4 containing 50 mM Na-Phosphate, 150 mM NaCl, 0.05% Tween 20, 0.005% $NaN_3$. For the FcγRs binding assay, anti-Histidine antibody (GE Healthcare) was immobilized onto all flow cells of a CM4 sensor chip using amine coupling kit (GE Healthcare). Each of the FcγRs were captured on flow cell 2, 3, or 4 by anti-Histidine antibody, with flow cell 1 as reference flow cell. FcγRs capture levels were aimed at 400 resonance unit (RU). All antibodies were injected at 100 nM over all flow cells. Immune complex were prepared by mixing 1:1 molar ratio of antibody and trimeric CD154, and incubated at room temperature for one hour. Sensor surface was regenerated after each cycle using 10 mM Glycine-HCl, pH 1.5.

For the FcRn binding assay, Biotin CAPture Reagent (GE Healthcare) was immobilized onto both flow cells 1 and 2 of a CAP sensor chip using Biotin CAPture kit (GE Healthcare). Biotinylated-FcRn was captured onto flow cell 2 with flow cell 1 as reference flow cell. FcRn capture levels were aimed at 400 RU. All antibodies were injected at 100 nM over flow cells 1 and 2. Immune complexes were prepared by mixing 1:1 molar ratio of antibody and trimeric CD154, and incubated at room temperature for one hour. Sensor surface was regenerated after each cycle using 8M Guanidine-HCl, 1M NaOH (3:1 vol/vol).

Figure 6:
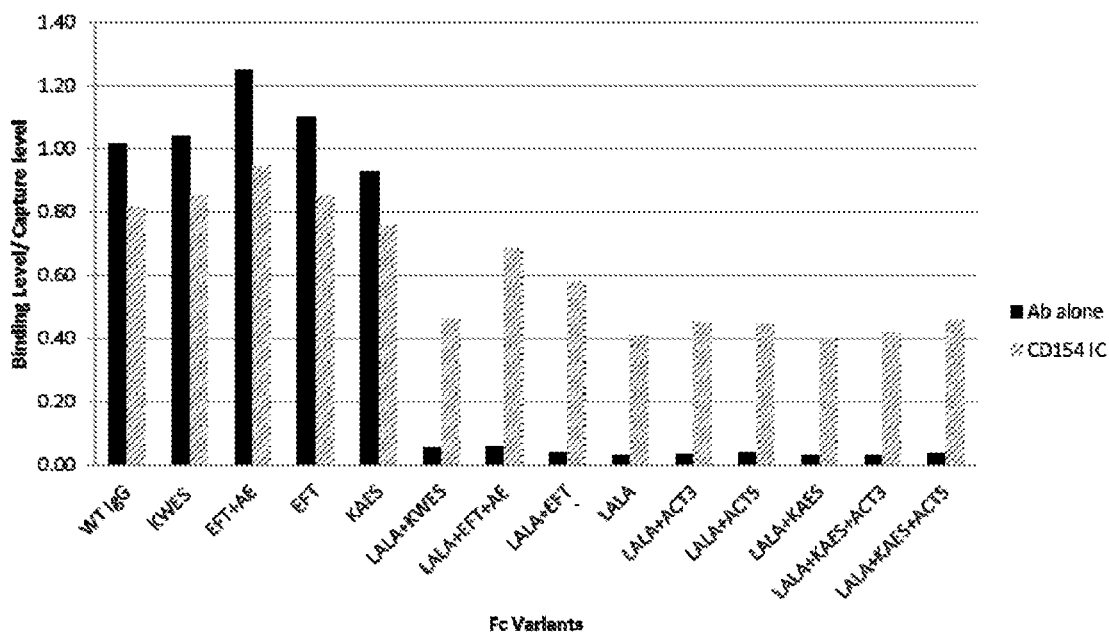
FIGS. 6 (a)-(h) illustrate Biacore analysis for Fc variants binding to human FcγRs, as described in Example 5. Fc variants tested are: WT (described as WT IgG in the figure), KWES, EFT+AE, EFT, KAES, LALA+KWES, LALA+EFT+AE, LALA+EFT, LALA, LALA+ACT3, LALA+ACT5, LALA+KAES, LALA+KAES+ACT3, and LALA+KAES+ACT5. These Fc variants were tested for binding to FcγRs including: (a) human FcγR1a, (b) human FcγR2a allelic variant 167H, (c) human FcγR2a allelic variant 167R, (d) human FcγR2b, (e) human FcγR3a allelic variant 158F, (f) human FcγR3a allelic variant 158V, (g) human FcγR3b allelic variant NA1, and (h) human FcγR3b allelic variant NA2. Each Fc variant was evaluated both in the form of an antibody alone with the Fc variant (described as Ab alone) and in the form of an immune complex formed with the antibody and a trimeric CD154 antigen (described as CD154 IC).
Figure 6:
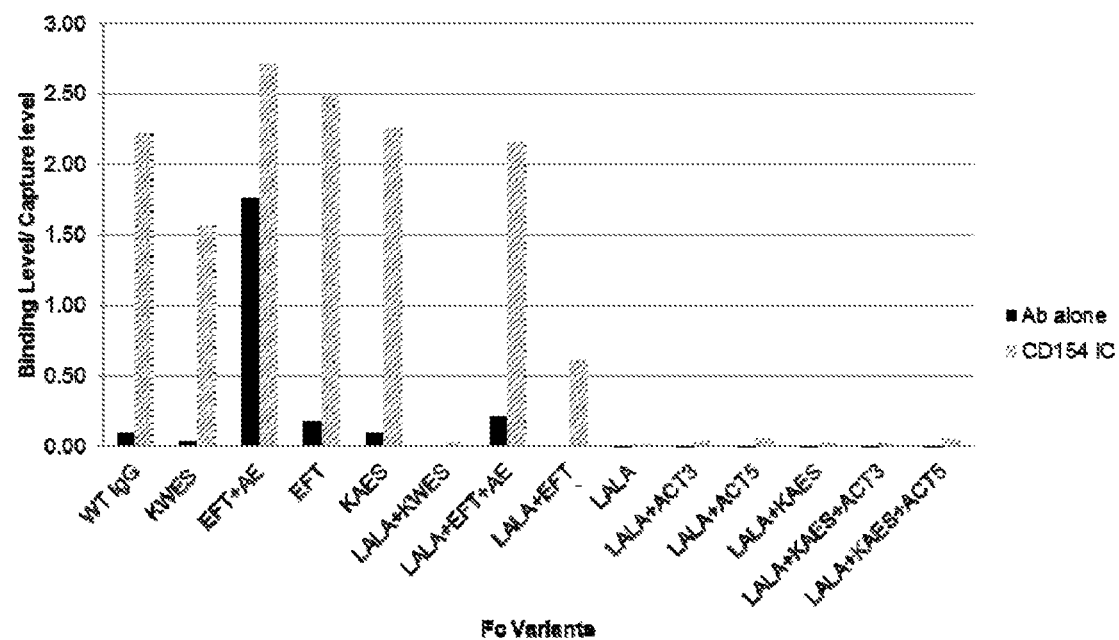
Figure 6:
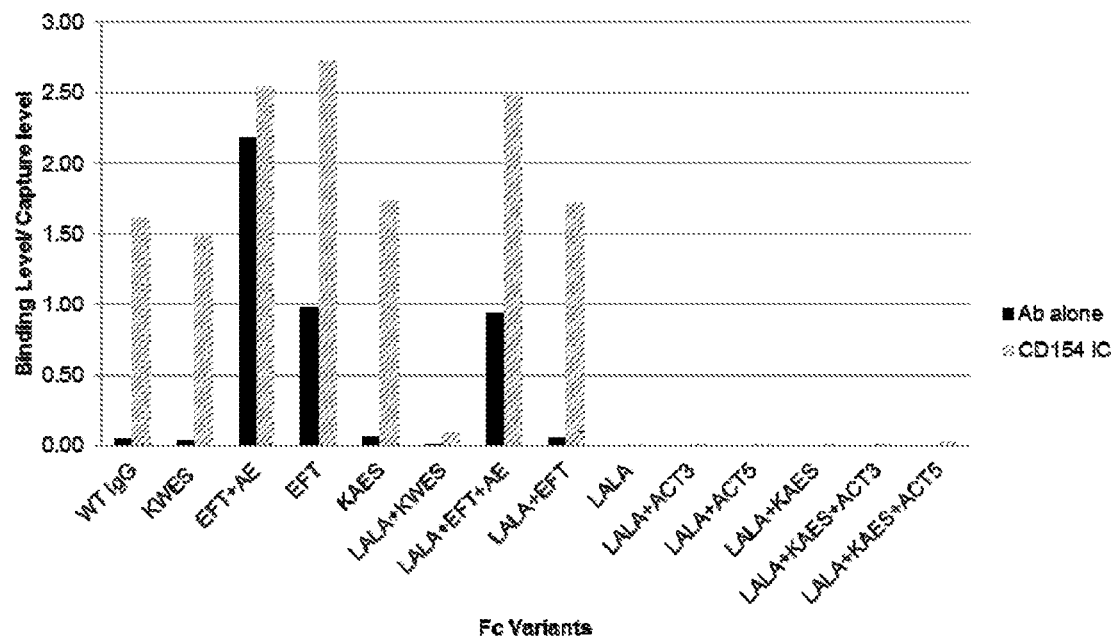
Figure 6:
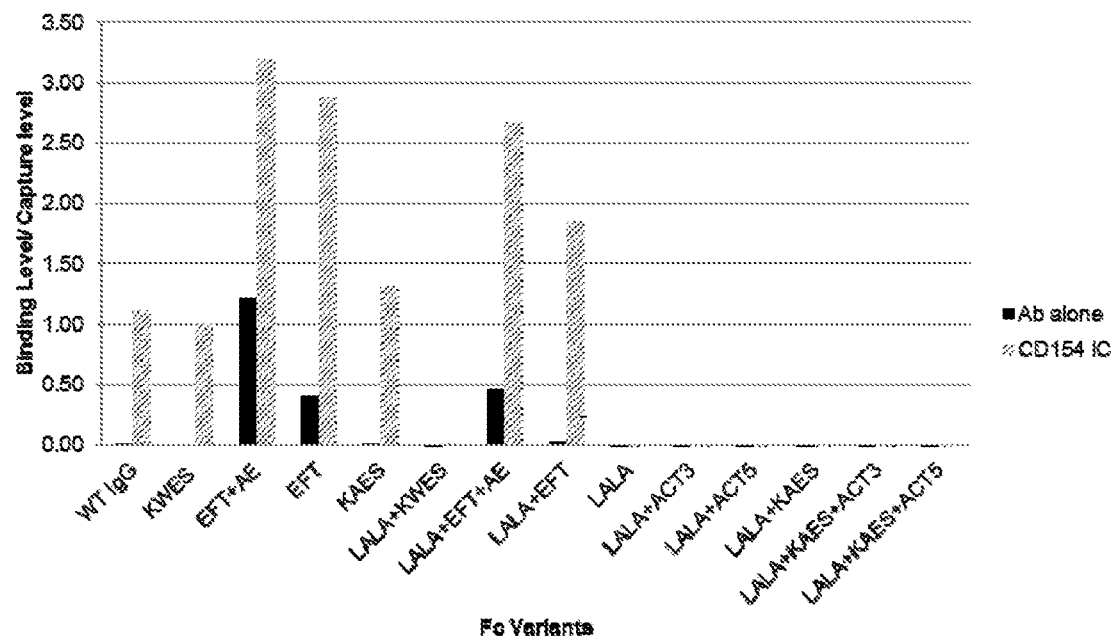
Figure 6:
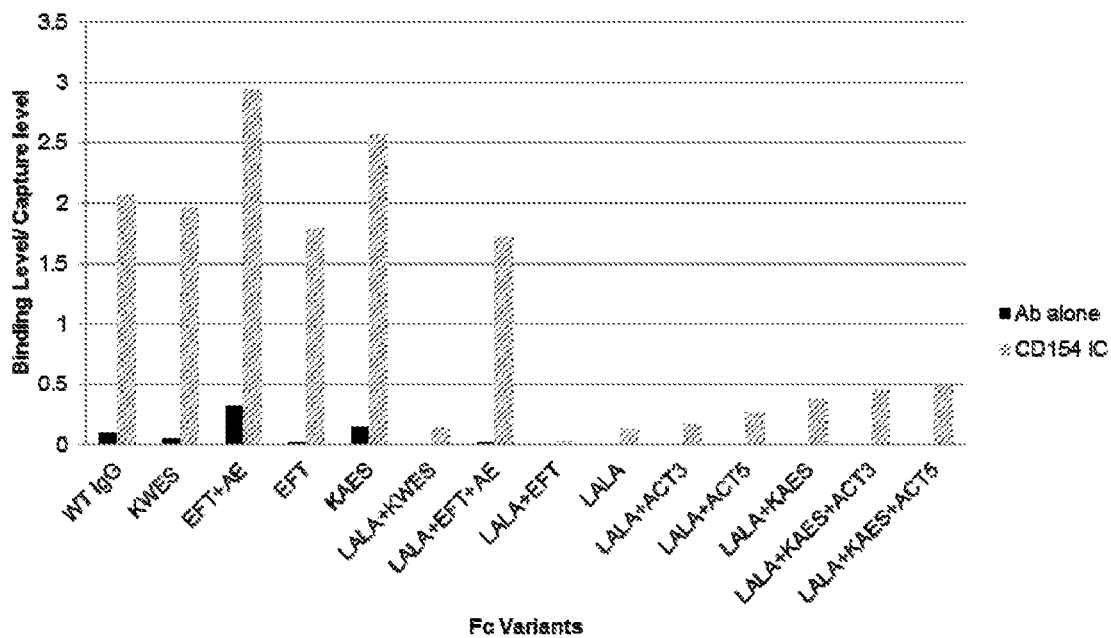
Figure 6:
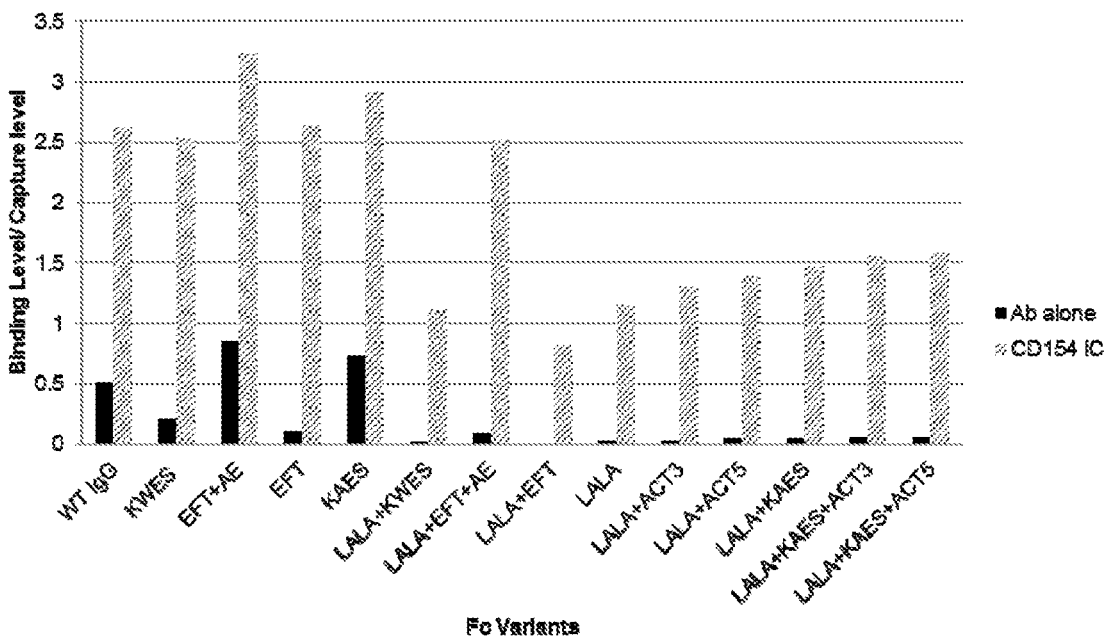
Figure 6:
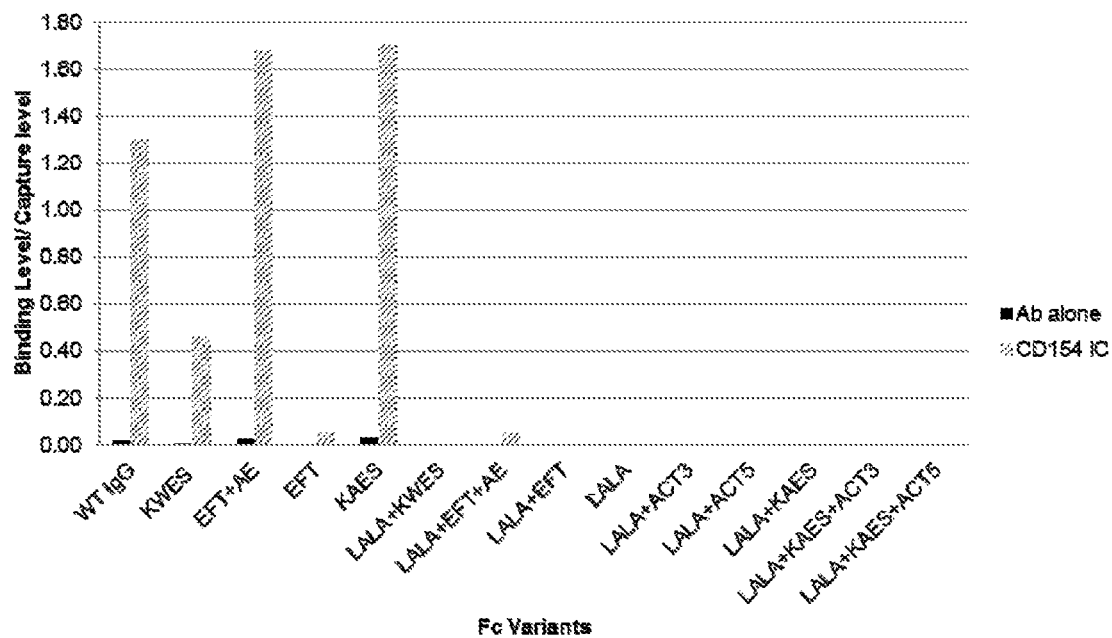
Figure 6:
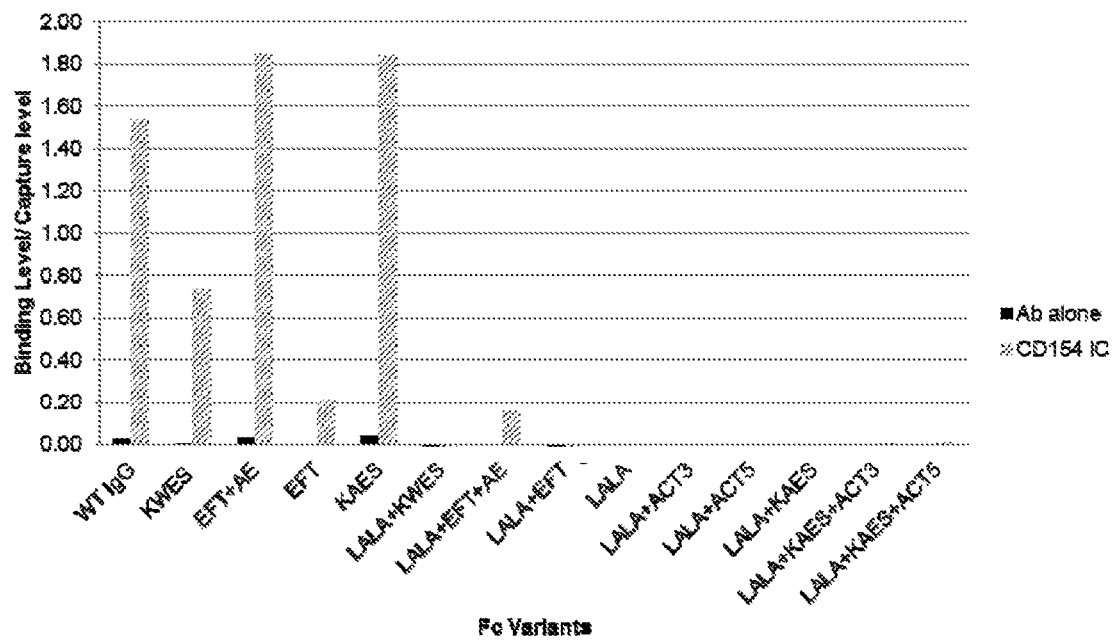
Figure 7:
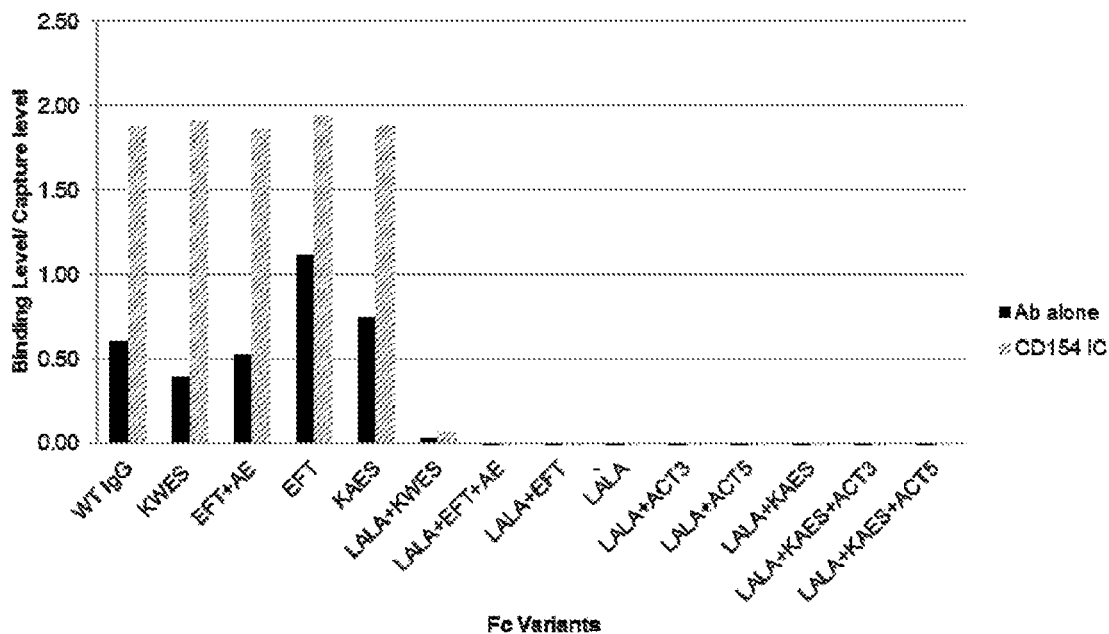
FIGS. 7 (a)-(d) illustrate Biacore analysis for Fc variants binding to mouse FcγRs, as described in Example 5. Fc variants tested are: WT (described as WT IgG in the figure), KWES, EFT+AE, EFT, KAES, LALA+KWES, LALA+EFT+AE, LALA+EFT, LALA, LALA+ACT3, LALA+ACT5, LALA+KAES, LALA+KAES+ACT3, and LALA+KAES+ACT5. These Fc variants were tested for binding to FcγRs including: (a) mouse FcγR1, (b) mouse FcγR2b, (c) mouse FcγR3, and (d) mouse FcγR4. Each Fc variant was evaluated both in the form of an antibody alone with the Fc variant (described as Ab alone) and in the form of an immune complex formed with the antibody and a trimeric CD154 antigen (described as CD154 IC).
Figure 7:
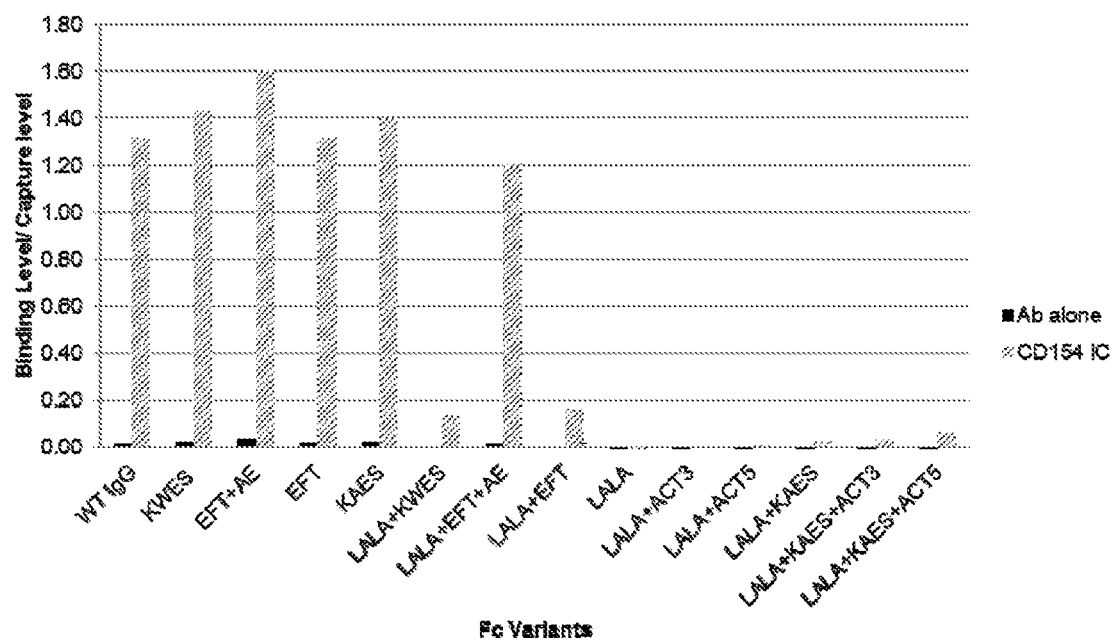
Figure 7:
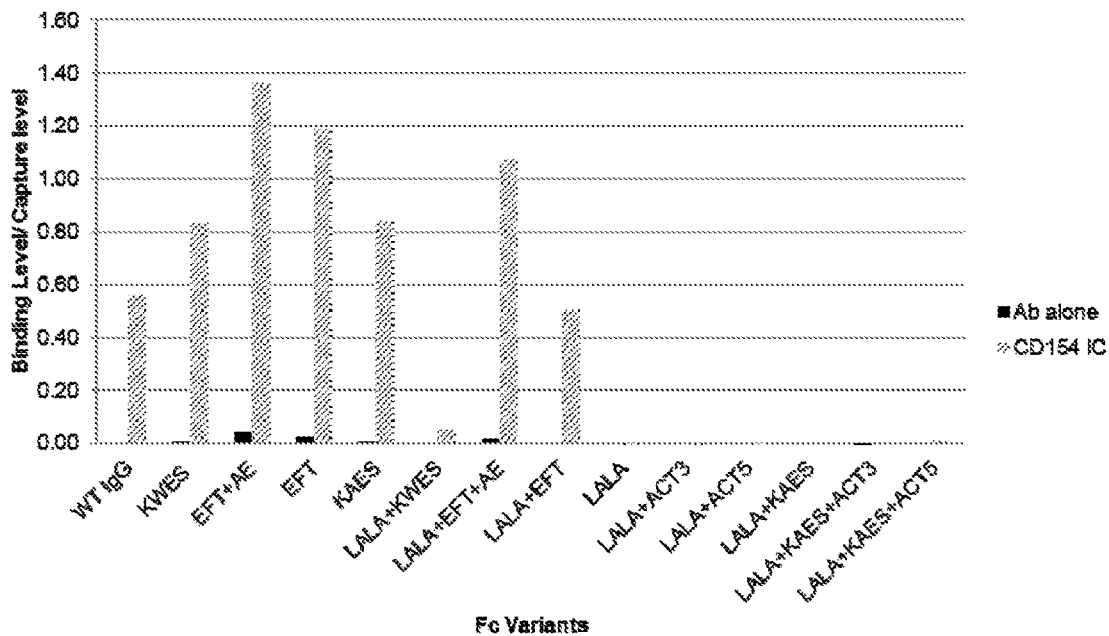
Figure 7:
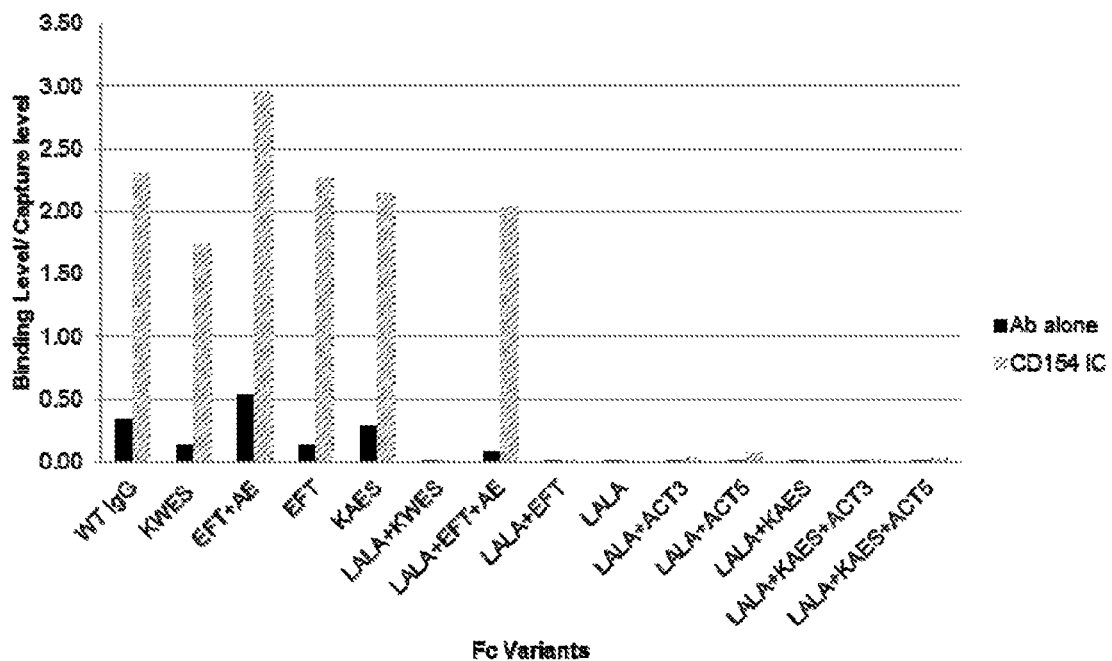
Figure 8:
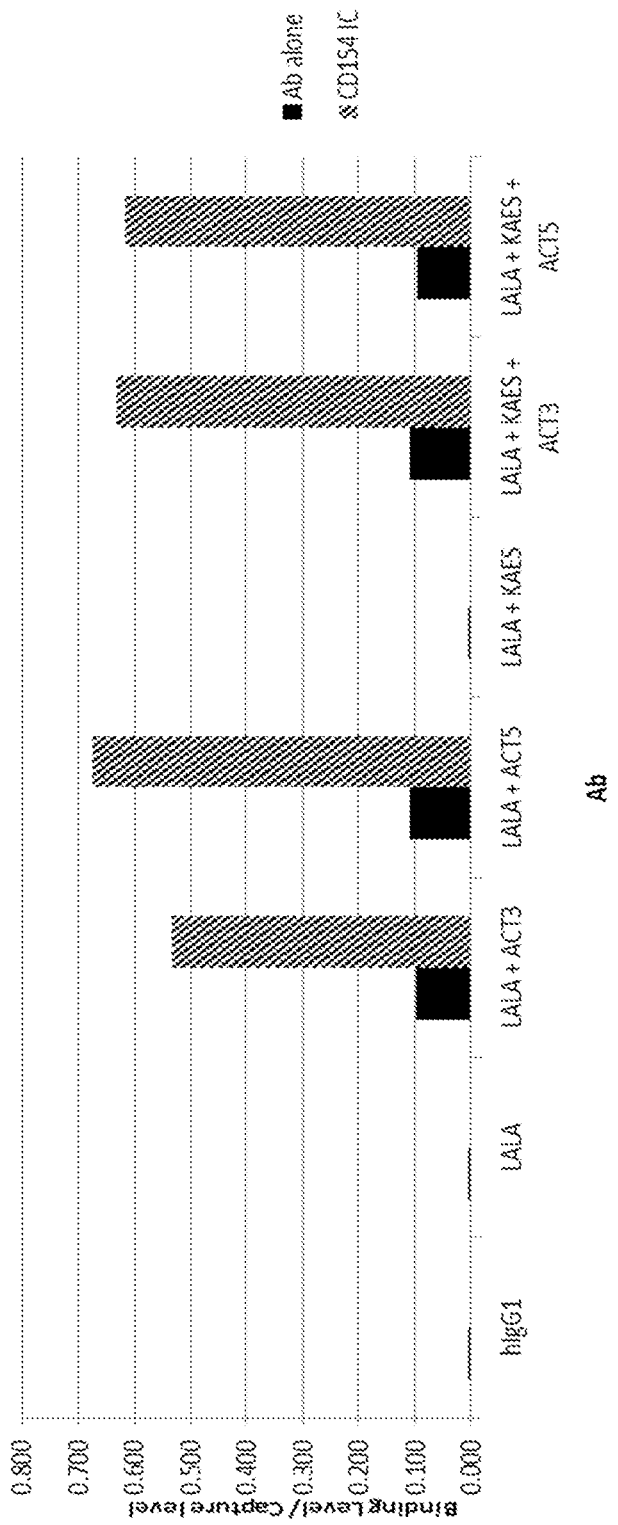
FIG. 8 illustrates Biacore analysis for Fc variants binding to human FcRn, as described in Example 5. Fc variants tested are: WT (described as hIgG1 in the figure), LALA, LALA+ACT3, LALA+ACT5, LALA+KAES, LALA+KAES+ACT3, and LALA+KAES+ACT5. Each Fc variant was evaluated both in the form of an antibody alone with the Fc variant (described as Ab alone) and in the form of an immune complex formed with the antibody and a trimeric CD154 antigen (described as CD154 IC).

Binding levels were normalized to the capture level of corresponding FcγRs or FcRn. The binding of an antibody alone or an immune complex (an antibody and a trimeric CD154 antigen) towards human or mouse FcγRs and human FcRn were monitored based on the binding response. The immune complex was used to evaluate the enhanced binding towards FcγRs or FcRn through avidity effects. The results for human FcγR1a, FcγR2a 167H and 167R, FcγR2b, FcγR3a 158F and 158V, FcγR3b NA1 and NA2 are shown in FIGS. 6 (a)-(h). The results for mouse FcγR1, FcγR2b, FcγR3, FcγR4 are shown in FIGS. 7 (a)-(d). The binding of a wild type Fc region (described as WT IgG) was significantly decreased by introducing LALA, LALA+KAES, or LALA+KWES mutations into the Fc region for each of the FcγRs tested. The tendency was roughly the same between the assays using the antibody alone (described as Ab alone) and the immune complex (described as CD154 IC). The binding of KAES or KWES mutants were not greatly reduced compared to that of WT IgG for most of the FcγRs tested. The results for human FcRn are shown in FIG. 8. The binding of a wild type Fc region (described as hIgG1) to human FcRn did not appear to be affected, even after introducing LALA or LALA+KAES mutations into the Fc region. The binding was slightly enhanced by further introducing ACT3 or ACT5 mutations but still remained comparatively low (FIG. 8).

Figure 9:
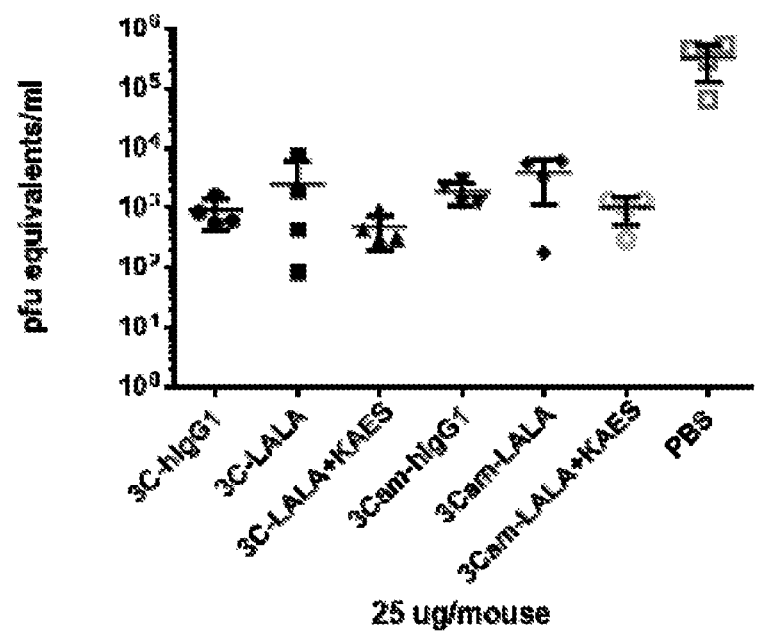
FIG. 9 illustrates viremia at day 3 after DENV-2 virus infection in AG129 mice, as described in Example 6. Anti-DENV antibodies 3C and 3Cam in combination with Fc variants of WT (described as hIgG1), LALA, and LALA+KAES, or PBS as a negative control were administered at day 2 after virus infection.

Example 6: In Vivo Efficacy of Anti-DENV Antibodies Against DENV Infection 6-8 weeks old AG129 mice were infected intraperitoneally with $10^6$ plaque-forming units (pfu) DENV-2 strain D2Y98P. 48 hours later, the mice were treated with 25 μg antibody in PBS. The antibody was injected intravenously via the retro-orbital route. Further 24 hours later, that is 72 hours after the initial infection, blood was collected. In previous studies (Zust et al, J Virol (2014) 88, 7276-7285; Tan et al, PLOS Negl Trop Dis (2010) 4, e672), it has been established that peak viremia after infection with D2Y98P is reached between day 3-4 after infection. Viral RNA was extracted from the plasma from each mouse and a quantitative PCR was performed and compared against a DENV-2 standard with known infectivity in a plaque assay. Both 3C and 3Cam antibodies greatly reduced viremia, compared to PBS control in this mice model, and the efficacy of both antibodies were comparable. The antibody having the LALA+KAES mutation in Fc region showed stronger efficacy compared to the antibody with only the LALA mutation. This was the case for both the 3C and the 3Cam antibodies (FIG. 9). This result indicates that recovery of C1q binding activity by adding KAES mutation to LALA mutation contributes to antiviral efficacy of the antibodies.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A process for preparing an antibody comprising: (a) HVR-H1 comprising the amino acid sequence of SEQ ID NO: 12, (b) HVR-H2 comprising the amino acid sequence of SEQ ID NO: 15, (c) HVR-H3 comprising the amino acid sequence of SEQ ID NO: 20, (d) HVR-L1 comprising the amino acid sequence of SEQ ID NO: 21, (e) HVR-L2 comprising the amino acid sequence of SEQ ID NO: 24 and (f) HVR-L3 comprising the amino acid sequence of SEQ ID NO: 27, the process comprising the steps of:

(a) combining a VH variant sequence selected from the group consisting of: 3CH1047 (SEQ ID NO: 6), and 3CH1049 (SEQ ID NO: 95) with a human IgG1 CH sequence selected from the group consisting of: SG182 (SEQ ID NO: 46), SG1095 (SEQ ID NO: 54) and SG1106 (SEQ ID NO: 59);

(b) combining a VL variant sequence selected from the group consisting of 3CL (SEQ ID NO: 7) and 3CL633 (SEQ ID NO: 98), with a human CL sequence SK1 (SEQ ID NO: 60);

(c) cloning each one of the combinations in an expression vector;

(d) expressing the resulting expression vectors in co-transfected cells; and (e) purifying the resulting antibody from step (d).

* * * * *